US011759461B2

(12) United States Patent
Lairson et al.

(10) Patent No.: US 11,759,461 B2
(45) Date of Patent: Sep. 19, 2023

(54) SMALL MOLECULE INHIBITORS OF CANCER STEM CELLS AND MESENCHYMAL CANCER TYPES

(71) Applicants: The Scripps Research Institute, La Jolla, CA (US); Board of Regents, The University of Texas System, Austin, TX (US)

(72) Inventors: Luke L. Lairson, San Diego, CA (US); Michael J. Bollong, San Diego, CA (US); Peter G. Schultz, La Jolla, CA (US); Sendurai A. Mani, Houston, TX (US)

(73) Assignees: THE SCRIPPS RESEARCH INSTITUTE, La Jolla, CA (US); THE UNIVERSTY OF TEXAS SYSTEM,BOARD OF REGENTS, Austin, TX (US)

( * ) Notice: Subject to any disclaimer, the term of this patent is extended or adjusted under 35 U.S.C. 154(b) by 216 days.

(21) Appl. No.: 15/733,051

(22) PCT Filed: Oct. 30, 2018

(86) PCT No.: PCT/US2018/058190
§ 371 (c)(1),
(2) Date: Apr. 30, 2020

(87) PCT Pub. No.: WO2019/089577
PCT Pub. Date: May 9, 2019

(65) Prior Publication Data
US 2021/0196713 A1 Jul. 1, 2021

Related U.S. Application Data
(60) Provisional application No. 62/578,897, filed on Oct. 30, 2017.

(51) Int. Cl.
| | | |
|---|---|---|
| *A61K 31/502* | (2006.01) | |
| *A61P 35/00* | (2006.01) | |
| *A61K 31/437* | (2006.01) | |
| *A61K 31/4704* | (2006.01) | |
| *A61K 31/4741* | (2006.01) | |
| *A61K 31/497* | (2006.01) | |
| *A61K 31/4985* | (2006.01) | |
| *A61K 31/551* | (2006.01) | |

(52) U.S. Cl.
CPC .......... *A61K 31/502* (2013.01); *A61K 31/437* (2013.01); *A61K 31/4704* (2013.01); *A61K 31/4741* (2013.01); *A61K 31/497* (2013.01); *A61K 31/4985* (2013.01); *A61K 31/551* (2013.01); *A61P 35/00* (2018.01)

(58) Field of Classification Search
CPC ................ A61K 31/502; A61K 31/498; A61K 31/4985; A61P 35/00
See application file for complete search history.

(56) References Cited

U.S. PATENT DOCUMENTS

| | | |
|---|---|---|
| 5,304,555 A | 4/1994 | Awaya et al. |
| 2004/0152690 A1 | 8/2004 | Balan et al. |
| 2014/0275201 A1 | 9/2014 | Mani et al. |
| 2015/0329497 A1 | 11/2015 | Pinkerton et al. |

FOREIGN PATENT DOCUMENTS

| | | |
|---|---|---|
| WO | WO-2016071293 A2 | 5/2016 |
| WO | WO-2019089577 A1 | 5/2019 |

OTHER PUBLICATIONS

"International Application Serial No. PCT US2018 057112, International Preliminary Report on Patentability dated May 7, 2020", 16 pages.
"European Application Serial No. 18801243.9, Response to Communication pursuant to Rules 161(1) and 162 EPC filed Dec. 16, 2020", 248 pages.
"International Application Serial No. PCT/US2018/058190, International Search Report dated Apr. 15, 2019", 9 pgs.
"International Application Serial No. PCT/US2018/058190, Invitation to Pay Additional Fees and Partial Search Report dated Feb. 25, 2019", 20 pgs.
"International Application Serial No. PCT/US2018/058190, Written Opinion dated Apr. 15, 2019", 17 pgs.
Bollong, J Michael, et al., "A vimentin binding small molecule leads to mitotic disruption in mesenchymal cancers", Proceedings of the National Academy of Sciences of the United States of America, vol. 114, No. 46, (Oct. 30, 2017), E9903-E9912.
Corzo, C A, et al., "Antiproliferation Activity of a Small Molecule Repressor of Liver Receptor Homolog 1", Molecular Pharmacology, vol. 87, No. 2, (Jan. 7, 2015), 296-304.
Hollier, B G, et al., "FOXC2 Expression Links Epithelial-Mesenchymal Transition and Stem Cell Properties in Breast Cancer", Cancer Research, vol. 73, No. 6, (Feb. 1, 2013), 1981-1992.
Jose, T Thaiparambil, et al., "Withaferin A inhibits breast cancer invasion and metastasis at sub-cytotoxic doses by inducing vimentin disassembly and serine 56 phosphorylation", International Journal of Cancer, vol. 129, No. 11, (May 2, 2011), 2744-2755.
Li, Q, et al., "3D Models of Epithelial-Mesenchymal Transition in Breast Cancer Metastasis: High-Throughput Screening Assay Development, Validation, and Pilot Screen", Journal of Biomolecular Screening, vol. 16, No. 2, (Feb. 1, 2011), 141-154.
Paranjape, A N, et al., "Inhibition of FOXC2 restores epithelial phenotype and drug sensitivity in prostate cancer cells with stem-cell properties", Oncogene, vol. 35, No. 46, (Jan. 25, 2016), 5963-5976.

(Continued)

*Primary Examiner* — James D. Anderson
(74) *Attorney, Agent, or Firm* — Schwegman Lundberg & Woessner, P.A.

(57) ABSTRACT

The present disclosure provides compounds, their pharmaceutical compositions, and methods of their use for treating mesenchymally-derived or mesenchymally transformed cancers, such as breast cancers and sarcomas, and for treating diseases or disorders that are characterized by the expression of vimentin.

1 Claim, 6 Drawing Sheets

(56) References Cited

OTHER PUBLICATIONS

Thuraya, Al-Harthy, et al., "Design, Synthesis, and Cytotoxicity of 5-Fluoro-2-methyl-6-(4-aryl-piperazin-l-yl) Benzoxazoles", Molecules Online, vol. 21, No. 10, (Oct. 1, 2016), 1290.

Zhang, Hu, et al., "Synthesis and biological evaluation of 1-cyano-2-amino-benzimidazole derivatives as a novel class of antitumor agents", Medicinal Chemistry Research., vol. 23, No. 6, (Dec. 21, 2013), 3029-3038.

Mani, Sendurai A., et al., "Mesenchyme Forkhead 1 (FOXC2) plays a key role in metastasis and is associated with aggressive basal-like breast cancers", PNAS, vol. 104, No. 24, 10069-10074; www.pnas.org/cgi/doi/10.1073/pnas.0703900104, (Jun. 12, 2007), 10069-10074.

Wang, Shuo, et al., "FOXF2 reprograms breast cancer cells into bone metastasis seeds", Nature Communications (2019) 10:2707; https://doi.org/10.1038/s41467-019-10379-7; www.nature.com/naturecommunications, (Jun. 20, 2019), 16 pgs.

SMALL MOLECULE INHIBITORS OF CANCER STEM CELLS AND MESENCHYMAL CANCER TYPES

This application is a U.S. national stage application filed under 35 U.S.C. 371 from International Application No, PCT/US2018/058190, filed on 30 Oct. 2018 and published as WO2019/089577 on 9 May 2019, which claims the benefit of priority to U.S. Provisional Patent Application No. 62/578,897, filed on Oct. 30, 2017, the benefit of priority of each of which is claimed herein, and wherein each application and publication is incorporated in its entirety as if fully set forth herein.

GOVERNMENT LICENSE RIGHTS

This invention was made with government support under grant number CA200970 awarded by the National Institutes of Health. The government has certain rights in the invention.

BACKGROUND

Cancer stem cells (CSCs) play critical roles in cancer progression and treatment resistance. A wealth of literature has demonstrated that epithelial-mesenchymal transition (EMT) processes are responsible for generating the CSC pool in multiple cancer types, including breast cancer, and for endowing cancer cells with metastatic competence.

Current breast cancer standards of care include hormonal treatments (e.g. tamoxifen, anastrozole, letrozole), HER-2 targeted therapies (trastuzumab, lapatinib), and conventional chemotherapeutic agents (e.g. docetaxel, doxorubicin, capecitabine). Yet, none of these therapies target the CSC population and, therefore, in addition to their respective side effects, the therapies have limited efficacy in promoting relapse free survival and inhibiting metastasis. In this context, resistance to chemotherapy and metastasis are the major causes for breast cancer-related mortality.

Soft tissue sarcomas (STS) are a rare and heterogeneous class of tumors, grouped solely by their mesenchymal origin (I. Zambo et al. *Cesk Patol* 50 (2014) 64-70). Current standards of care for STS patients are currently limited to surgical resection and treatment with typical DNA-damaging chemotherapies (e.g., doxorubicin, ifosfamide) or radiation, interventions which yield five-year median survival rates of only 50% for late stage STS patients (M. J. Nathenson et al. *Cancer Chemother. Pharmacol.* 78 (2016) 895-919). Additionally, only a handful of targeted therapies have been approved or are under investigation for STS indications (A. R. Dancsok et al. *Oncotarget* 8(4) (2017) 7068-7093).

Although a host of transcription factors and mitogens are capable of inducing EMT in breast cancer, the presence of transition factor Forkhead Box C2 (FOXC2) is reported for effective EMT via any stimulus studied to date (S. A. Mani et al., *Proc. Natl. Acad. Sci. USA* 104 (2007) 10069-10074; B. G. Hollier et al., *Cancer Res.* 73 (2013) 1981-1982). Additionally, exogenous expression of FOXC2 is reported to endow non-metastatic cancer cell lines with metastatic potential (Hollier (2013)).

SUMMARY

The present disclosure provides compounds that are useful as selectively cytotoxic agents against cells of the EMT-CSC phenotype. In addition, the compounds also inhibit the growth of mesenchymally-transformed cancer cells by binding to and interfering with the organization and phosphorylation of vimentin during mitosis. In contrast to the many naturally- and synthetically-derived compounds targeting microtubules, the compounds disclosed herein target the intermediate filament protein vimentin to promote mitotic catastrophe. Because vimentin expression is manifested in mesenchymal as well as endothelial and haemopoietic cell types, the compounds moreover constitute genotype-selective chemotherapeutics for the treatment of mesenchymal cancers and other disorders, such as those involving non-mesenchymal cell types, that involve vimentin expression. The disclosure thus provides in one embodiment a method for treating a patient suffering from a mesenchymally-derived or mesenchymally-transformed cancer, comprising administering to the subject a therapeutically effective amount of a compound, or a pharmaceutically acceptable salt there, according to any one of Formulae I-IV:

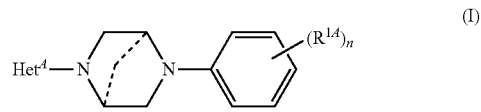

(I)

In Formula I compounds, $R^{1A}$ in each instance is independently selected from the group consisting of $C_1$-$C_6$-alkyl, $C_2$-$C_6$-alkenyl, and $C_1$-$C_6$-alkoxy, halo, CN, —S—$C_1$-$C_6$-alkyl, and —C(O)N($R^{2A}$)$_2$.

$R^{2A}$ in each instance is independently selected from H and $C_1$-$C_6$-alkyl;

Each ---, if present, represents a single bond, and n is 0, 1, 2, or 3.

$Het^A$ is 6-membered monocyclic or 9- to 10-membered bicyclic heteroaryl, wherein 1 to 3 ring members are N;

$Het^A$ and any alkyl, alkenyl, alkoxy, and aryl is optionally substituted with 1-3 substituents selected from the group consisting of $C_1$-$C_6$-alkyl, OH, halo, CN, $C_1$-$C_6$-alkoxy, —C(O)$C_1$-$C_6$-alkyl, and —C(O)O—$C_1$-$C_6$-alkyl.

Formula II compounds conform to the following structure:

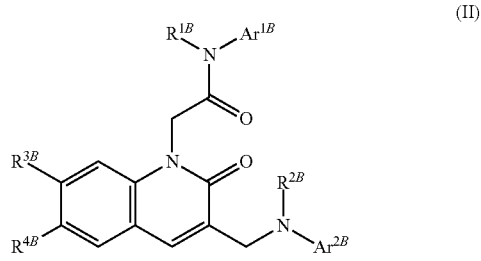

(II)

In Formula II, $R^{1B}$ and $R^{2B}$ are independently selected from the group consisting of H, $C_1$-$C_6$-alkyl, and $C_2$-$C_6$-alkenyl.

$R^{3B}$ and $R^{4B}$ are independently selected from the group consisting of H, $C_1$-$C_6$-alkyl, $C_2$-$C_6$-alkenyl, and $C_1$-$C_6$-alkoxy.

Alternatively, $R^{3A}$ and $R^{4A}$, together with the carbon atoms to which they are attached, represent a fused 5- to 6-membered heterocycle, wherein 1 to 2 ring members are selected from $NR^{1B}$, O, and S.

$Ar^{1B}$ and $Ar^{2B}$ are independently $C_6$-$C_{10}$-aryl.

Any alkyl, alkenyl, alkoxy, aryl, and heteroaryl is optionally substituted with one or more substituents selected from the group consisting of $C_1$-$C_6$-alkyl, OH, halo, CN, $C_1$-$C_6$-alkoxy, —C(O)$C_1$-$C_6$-alkyl, and —C(O)O—$C_1$-$C_6$-alkyl.

Formula III compounds conform to the following structure:

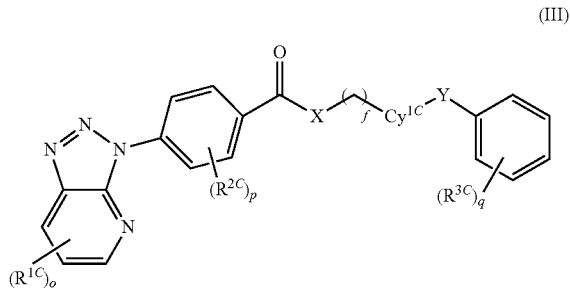

(III)

In Formula III, $R^{1C}$, $R^{2C}$, and $R^{3C}$ are independently selected from the group consisting of H, $C_1$-$C_6$-alkyl, $C_2$-$C_6$-alkenyl, halo, CN, $C_1$-$C_6$-alkoxy, —C(O)$C_1$-$C_6$-alkyl, and —C(O)O—$C_1$-$C_6$-alkyl.

Integer f is 0, 1, 2, or 3; and integers o, p, and q are independently selected from 0, 1, 2, 3, 4, and 5.

X and Y are independently selected from the group consisting of a bond, —NH—, and —CH$_2$—.

$Cy^{1C}$ is selected from the group consisting of $C_3$-$C_8$-cycloalkyl and 3- to 7-membered heterocyclo wherein 1-3 ring members are selected from N, O, and S.

Any alkyl, alkenyl, alkoxy, aryl, and heterocyclo is optionally substituted with 1-3 substituents selected from the group consisting of $C_1$-$C_6$-alkyl, OH, halo, CN, $C_1$-$C_6$-alkoxy, —C(O)$C_1$-$C_6$-alkyl, and —C(O)O—$C_1$-$C_6$-alkyl.

Formula IV compounds conform to the following structure:

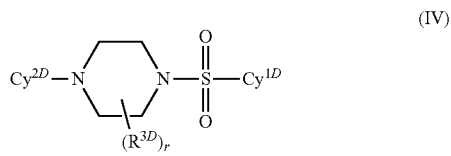

(IV)

In Formula IV, $Cy^{1D}$ is a 5- to 6-membered heteroaryl (wherein 1-3 ring members are N) or $C_6$-$C_{10}$-aryl, wherein $Cy^{1D}$ is optionally substituted by 1-3 $R^{1D}$.

$Cy^{2D}$ is a 5- to 6-membered heteroaryl (wherein 1-3 ring members are N) or $C_6$-$C_{10}$-aryl, wherein $Cy^{2D}$ is optionally substituted by 1-3 $R^{2D}$.

$R^{1D}$ in each instance is independently selected from the group consisting of $C_1$-$C_6$-alkyl, $C_2$-$C_6$-alkenyl, halo, $C_6$-$C_{10}$-aryl.

$R^{2D}$ in each instance is independently is selected from the group consisting of $C_1$-$C_6$-alkyl, $C_2$-$C_6$-alkenyl, halo, $C_6$-$C_{10}$-aryl.

$R^{1D}$ and $R^{2D}$ are not simultaneously $C_6$-$C_{10}$-aryl.

$R^{3D}$ in each instance is independently selected from the group consisting of $C_1$-$C_6$-alkyl, $C_2$-$C_6$-alkenyl, and halo.

Integer r is 0, 1, 2, or 3.

Any alkyl, alkenyl, alkoxy, heteroaryl, and aryl is optionally substituted with one or more substituents selected from the group consisting of $C_1$-$C_6$-alkyl, OH, halo, CN, $C_1$-$C_6$-alkoxy, —C(O)$C_1$-$C_6$-alkyl, and —C(O)O—$C_1$-$C_6$-alkyl.

Another embodiment of the disclosure is a compound according to any one of Formula I-IV for use treating a patient suffering from a mesenchymally-derived or mesenchymally-transformed cancer.

The disclosure further provides in another embodiment, optionally in combination with any other embodiment disclosed herein, a method of treating a subject suffering from a disease or condition that is characterized by the expression of vimentin. The method comprises administering to the subject a therapeutically effective amount of a compound, or a pharmaceutically acceptable salt thereof, according to any one of Formulae I-IV.

Still another embodiment, optionally in combination with any other embodiment disclosed herein, is a compound or a pharmaceutically acceptable salt thereof, according to any one of Formulae I-IV, for use in treating a patient suffering from a mesenchymally-derived or mesenchymally-transformed cancer, or from a disease or condition that is characterized by the expression of vimentin.

DETAILED DESCRIPTION

Definitions

Figure 1:
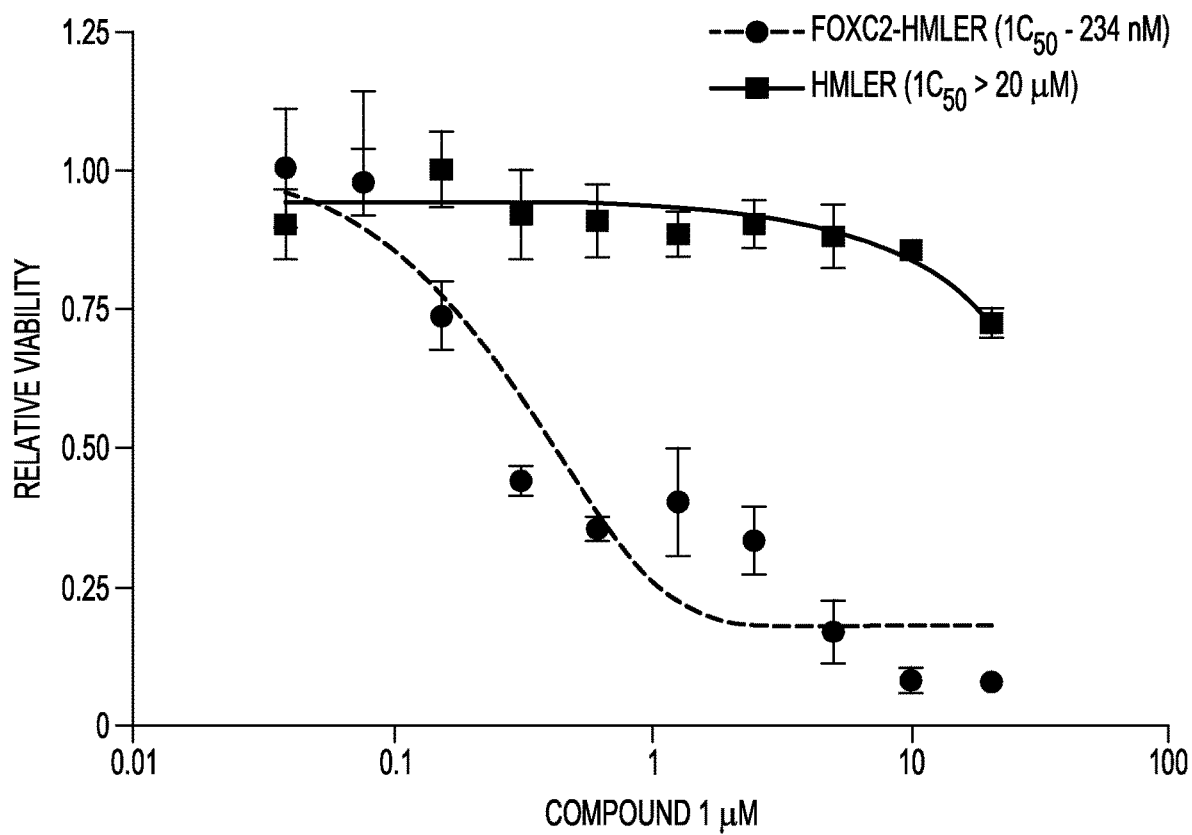
FIG. 1: Relative viability measurements of FOXC2 (lower trace) and control HMLER (upper trace) cells exposed to the indicated doses of Compound 1 for 72 hours (n=3, mean and s.e.m.).

"Alkyl" refers to straight, branched chain, or cyclic hydrocarbyl groups, e.g., "cycloalkyl," including from 1 to about 20 carbon atoms. For instance, an alkyl can have from 1 to 10 carbon atoms or 1 to 6 carbon atoms. Exemplary alkyl includes straight chain alkyl groups such as methyl, ethyl, propyl, butyl, pentyl, hexyl, heptyl, octyl, nonyl, decyl, undecyl, dodecyl, and the like, and also includes branched chain isomers of straight chain alkyl groups, for example without limitation, —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH (CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, and the like. Thus, alkyl groups include primary alkyl groups, secondary alkyl groups, and tertiary alkyl groups.

The phrase "substituted alkyl" refers to alkyl substituted at one or more positions, for example, 1, 2, 3, 4, 5, or even 6 positions, which substituents are attached at any available atom to produce a stable compound, with substitution as described herein. "Optionally substituted alkyl" refers to alkyl or substituted alkyl.

Each of the terms "halogen," "halide," and "halo" refers to —F, —Cl, —Br, or —I.

The term "alkenyl" refers to straight, branched chain, or cyclic hydrocarbyl groups, e.g., "cycloalkenyl," including from 2 to about 20 carbon atoms, such as 2 to carbon atoms, having 1-3, 1-2, or at least one carbon to carbon double bond. The term "cycloalkenyl" refers specifically to cyclic alkenyl, such as C$_3$-C$_6$-cycloalkenyl.

"Substituted alkenyl" refers to alkene substituted at 1 or more, e.g., 1, 2, 3, 4, 5, or even 6 positions, which substituents are attached at any available atom to produce a stable compound, with substitution as described herein. "Optionally substituted alkene" refers to alkene or substituted alkene.

The term "alkoxy" refers to an —O-alkyl group having the indicated number of carbon atoms. For example, a (C$_1$-C$_6$)alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

"Aryl" when used alone or as part of another term means a carbocyclic aromatic group whether or not fused having the number of carbon atoms designated or if no number is designated, up to 14 carbon atoms, such as a C$_6$-C$_{14}$-aryl. Particular aryl groups are phenyl, naphthyl, biphenyl, phenanthrenyl, naphthacenyl, and the like (see e.g. *Lang's Handbook of Chemistry* (Dean, J. A., ed) 13$^{th}$ ed. Table 7-2 [1985]). A particular aryl is phenyl. "Aryl" also includes aromatic ring systems that are optionally fused with a cycloalkyl ring, as herein defined.

A "substituted aryl" is an aryl that is independently substituted with one or more substituents attached at any available atom to produce a stable compound, wherein the substituents are as described herein. "Optionally substituted aryl" refers to aryl or substituted aryl.

The term "heteroatom" refers to N, O, and S. Inventive compounds that contain N or S atoms can be optionally oxidized to the corresponding N-oxide, sulfoxide, or sulfone compounds.

"Heteroaryl," alone or in combination with any other moiety described herein, refers to a monocyclic aromatic ring structure containing 5 to 10, such as 5 or 6 ring atoms, or a bicyclic aromatic group having 8 to 10 atoms, containing one or more, such as 1-4, 1-3, or 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or heteroatom is the point of attachment of the heteroaryl ring structure such that a stable compound is produced. Examples of heteroaryl groups include, but are not limited to, pyridinyl, pyridazinyl, pyrazinyl, quinoaxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl.

A "substituted heteroaryl" is a heteroaryl that is independently substituted, unless indicated otherwise, with one or more, e.g., 1, 2, 3, 4 or 5, also 1, 2, or 3 substituents, also 1 substituent, attached at any available atom to produce a stable compound, wherein the substituents are as described herein. "Optionally substituted heteroaryl" refers to heteroaryl or substituted heteroaryl.

"Heterocycloalkyl" or "heterocyclo" means a saturated or unsaturated non-aromatic monocyclic, bicyclic, tricyclic or polycyclic ring system that has from 3 to 14, such as 3 to 6, atoms in which from 1 to 3 carbon atoms in the ring are replaced by heteroatoms of O, S or N. A heterocycloalkyl is optionally fused with aryl or heteroaryl of 5-6 ring members, and includes oxidized S or N, such as sulfinyl, sulfonyl and N-oxide of a tertiary ring nitrogen. The point of attachment of the heterocycloalkyl ring is at a carbon or heteroatom such that a stable ring is retained. Examples of heterocycloalkyl groups include without limitation morpholino, tetrahydrofuranyl, dihydropyridinyl, piperidinyl, pyrrolidinyl, piperazinyl, dihydrobenzofuryl, and dihydroindolyl.

"Optionally substituted heterocycloalkyl" denotes heterocycloalkyl that is substituted with 1 to 3 substituents, e.g., 1, 2 or 3 substituents, attached at any available atom to produce a stable compound, wherein the substituents are as described herein.

The term "nitrile" or "cyano" can be used interchangeably and refer to a —CN group which is bound to a carbon atom of a heteroaryl ring, aryl ring and a heterocycloalkyl ring.

The substituent —CO$_2$H may be replaced with bioisosteric replacements such as:

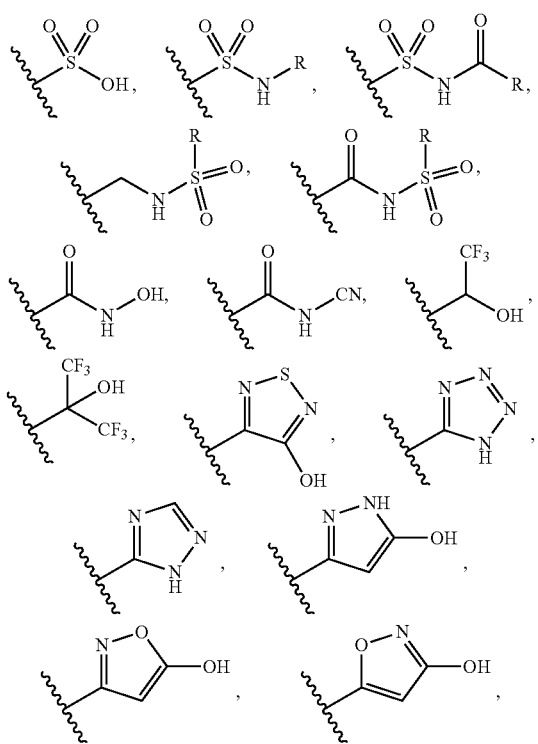

-continued

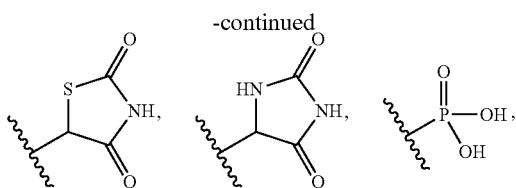

and the like, wherein R has the same definition as $R^A$ as defined herein. See, e.g., THE PRACTICE OF MEDICINAL CHEMISTRY (Academic Press: New York, 1996), at page 203.

Compounds described herein can exist in various isomeric forms, including configurational, geometric, and conformational isomers, including, for example, cis- or trans-conformations. The compounds may also exist in one or more tautomeric forms, including both single tautomers and mixtures of tautomers. The term "isomer" is intended to encompass all isomeric forms of a compound of this disclosure, including tautomeric forms of the compound. The compounds of the present disclosure may also exist in open-chain or cyclized forms. In some cases one or more of the cyclized forms may result from the loss of water. The specific composition of the open-chain and cyclized forms may be dependent on how the compound is isolated, stored or administered. For example, the compound may exist primarily in an open-chained form under acidic conditions but cyclize under neutral conditions. All forms are included in the disclosure.

Some compounds described herein can have asymmetric centers and therefore exist in different enantiomeric and diastereomeric forms. A compound of the disclosure can be in the form of an optical isomer or a diastereomer. Accordingly, the disclosure encompasses compounds and their uses as described herein in the form of their optical isomers, diastereoisomers and mixtures thereof, including a racemic mixture. Optical isomers of the compounds of the disclosure can be obtained by known techniques such as asymmetric synthesis, chiral chromatography, simulated moving bed technology or via chemical separation of stereoisomers through the employment of optically active resolving agents.

Unless otherwise indicated, the term "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

In this description, a "pharmaceutically acceptable salt" is a pharmaceutically acceptable, organic or inorganic acid or base salt of a compound of the disclosure. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease.

The terms "prevent," "preventing," and "prevention" refer to the prevention of the onset, recurrence, or spread of the disease in a patient resulting from the administration of a prophylactic or therapeutic agent.

The term "effective amount" refers to an amount of a compound of the disclosure or other active ingredient sufficient to provide a therapeutic or prophylactic benefit in the treatment or prevention of a disease or to delay or minimize symptoms associated with a disease. Further, a therapeutically effective amount with respect to a compound of the disclosure means that amount of therapeutic agent alone, or in combination with other therapies, that provides a therapeutic benefit in the treatment or prevention of a disease. Used in connection with a compound of the disclosure, the term can encompass an amount that improves overall therapy, reduces or avoids symptoms or causes of disease, or enhances the therapeutic efficacy of or synergies with another therapeutic agent.

A "patient" or subject" includes an animal, such as a human, cow, horse, sheep, lamb, pig, chicken, turkey, quail, cat, dog, mouse, rat, rabbit or guinea pig. The animal can be a mammal such as a non-primate and a primate (e.g., monkey and human). In one embodiment, a patient is a human, such as a human infant, child, adolescent or adult.

Compounds

As described generally above, the present disclosure provides in some embodiments compounds and pharmaceutically acceptable salts thereof, wherein the compounds conform to Formula (I):

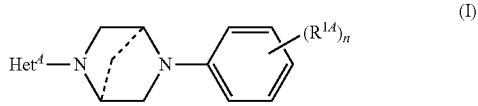

(I)

$R^{1A}$ in each instance is independently selected from the group consisting of $C_1$-$C_6$-alkyl, $C_2$-$C_6$-alkenyl, and $C_1$-$C_6$-alkoxy, halo, CN, —S—$C_1$-$C_6$-alkyl, —C(O)N($R^{2A}$)$_2$.

$R^{2A}$ in each instance is independently selected from H and $C_1$-$C_6$-alkyl;

Each ---, if present, represent single bonds; and n is 0, 1, 2, or 3.

$Het^4$ is 6-membered monocyclic or 9- to 10-membered bicyclic heteroaryl, wherein 1 to 3 ring members are N.

$Het^4$ and any alkyl, alkenyl, alkoxy, and aryl is optionally substituted with 1-3 substituents selected from the group consisting of $C_1$-$C_6$-alkyl, halo, OH, CN, $C_1$-$C_6$-alkoxy, —C(O)$C_1$-$C_6$-alkyl, and —C(O)O—$C_1$-$C_6$-alkyl.

In some embodiments, each --- is absent and $Het^4$ is a 9- to 10-membered bicyclic heteroaryl. Exemplary bicyclic heteroaryl groups include but are not limited to indole, isoindole, indolizine, quinolone, isoquinoline, quinolizine, indazole, quinazoline, cinnoline, quinoxaline, and phthalazine.

Other embodiments provide for substitution of $Het^4$. For example, $Het^4$ is substituted by 1-3 halogens, such as Cl and F.

In other embodiments, optionally in combination with any other embodiment, $R^{1A}$ is a halogen, and n is 1, 2, or 3.

Specific examples of Formula I compounds are presented in Table 1 as set forth below.

Formula II compounds are represented by the structure:

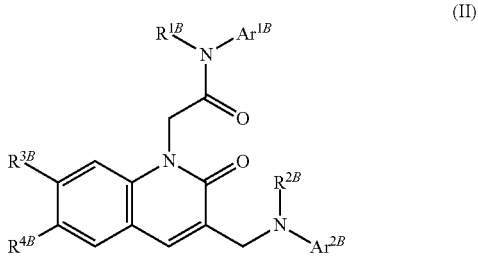

(II)

$R^{1B}$ and $R^{2B}$ are independently selected from the group consisting of H, $C_1$-$C_6$-alkyl, and $C_2$-$C_6$-alkenyl.

$R^{3B}$ and $R^{4B}$ are independently selected from the group consisting of H, $C_1$-$C_6$-alkyl, $C_2$-$C_6$-alkenyl, and $C_1$-$C_6$-alkoxy.

Alternatively, $R^{3A}$ and $R^{4A}$, together with the carbon atoms to which they are attached, represent a fused 5- to 6-membered heterocycle, wherein 1 to 2 ring members are selected from $NR^{1B}$, O, and S.

$Ar^{1B}$ and $Ar^{2B}$ are independently $C_6$-$C_{10}$-aryl.

Any alkyl, alkenyl, alkoxy, aryl, and heteroaryl is optionally substituted with one or more substituents selected from the group consisting of $C_1$-$C_6$-alkyl, OH, halo, CN, $C_1$-$C_6$-alkoxy, —C(O)$C_1$-$C_6$-alkyl, and —C(O)O—$C_1$-$C_6$-alkyl.

In some embodiments, $Ar^{1B}$ and $Ar^{2B}$ are independently and optionally substituted phenyl. Exemplary substituents in this context include $C_1$-$C_6$-alkyl and $C_1$-$C_6$-alkoxy.

Optionally in combination with other embodiments, another embodiment provides for each of $R^{1B}$ and $R^{2B}$ as H.

Specific examples of Formula II compounds are presented in Table 2 as set forth below.

Formula III compounds are represented by the structure:

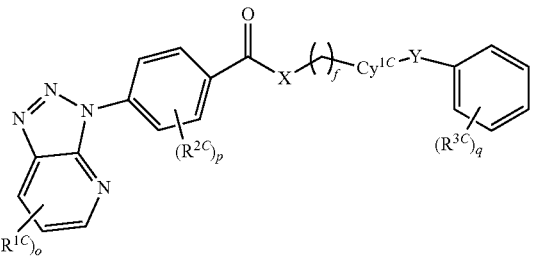

(III)

$R^{1C}$, $R^{2C}$, and $R^{3C}$ are independently selected from the group consisting of H, $C_1$-$C_6$-alkyl, $C_2$-$C_6$-alkenyl, halo, CN, $C_1$-$C_6$-alkoxy, —C(O)$C_1$-$C_6$-alkyl, and —C(O)O—$C_1$-$C_6$-alkyl.

The integer f is 0, 1, 2, or 3; o, p, and q are independently selected from 0, 1, 2, 3, 4, and 5.

X and Y are independently selected from the group consisting of a bond, —NH—, and —CH$_2$—.

$Cy^{1C}$ is selected from the group consisting of $C_3$-$C_8$-cycloalkyl and 3- to 7-membered hetercyclo wherein 1-3 ring members are selected from N, O, and S.

Any alkyl, alkenyl, alkoxy, aryl, and heterocyclo is optionally substituted with 1-3 substituents selected from the group consisting of $C_1$-$C_6$-alkyl, OH, halo, CN, $C_1$-$C_6$-alkoxy, —C(O)$C_1$-$C_6$-alkyl, and —C(O)O—$C_1$-$C_6$-alkyl;

According to some embodiments, X and Y each is a bond; f is 0; and $Cy^{1C}$ is an optionally substituted 3- to 7-membered hetercyclo wherein 1-3 ring members are N.

Other Formula III compounds, according to various embodiments, feature $Cy^{1C}$ as a 6-membered hetercyclo wherein 1-2 ring members are N. Examples of such a heterocyclo include piperidine, hexahydro-pyrimidine, and piperazine.

Specific examples of Formula III compounds are presented in Table 3 as set forth below.

Formula IV compounds are represented by the structure:

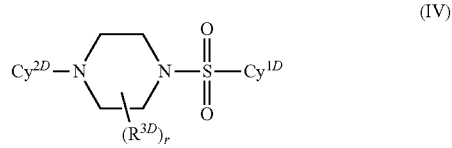

(IV)

$Cy^{1D}$ is a 5- to 6-membered heteroaryl (wherein 1-3 ring members are N) or $C_6$-$C_{10}$-aryl, wherein $Cy^{1D}$ is optionally substituted by 1-3 $R^{1D}$.

$Cy^{2D}$ is a 5- to 6-membered heteroaryl (wherein 1-3 ring members are N) or $C_6$-$C_{10}$-aryl, wherein $Cy^{2D}$ is optionally substituted by 1-3 $R^{2D}$.

$R^{1D}$ in each instance is independently selected from the group consisting of $C_1$-$C_6$-alkyl, $C_2$-$C_6$-alkenyl, halo, $C_6$-$C_{10}$-aryl.

$R^{2D}$ in each instance is independently is selected from the group consisting of $C_1$-$C_6$-alkyl, $C_2$-$C_6$-alkenyl, halo, $C_6$-$C_{10}$-aryl.

$R^{1D}$ and $R^{2D}$ are not simultaneously $C_6$-$C_{10}$-aryl.

$R^{3D}$ in each instance is independently is selected from the group consisting of $C_1$-$C_6$-alkyl, $C_2$-$C_6$-alkenyl, and halo.

Integer r is 0, 1, 2, or 3.

Any alkyl, alkenyl, alkoxy, heteroaryl, and aryl is optionally substituted with one or more substituents selected from the group consisting of $C_1$-$C_6$-alkyl, OH, halo, CN, $C_1$-$C_6$-alkoxy, —C(O)$C_1$-$C_6$-alkyl, and —C(O)O—$C_1$-$C_6$-alkyl.

In some embodiments, $Cy^{1D}$ is an optionally substituted 5- to 6-membered heteroaryl (wherein 1-3 ring members are N); and $Cy^{2D}$ is an optionally substituted 5- to 6-membered heteroaryl (wherein 1-3 ring members are N). Examples of 6-membered heteroaryl are described above. Examples of 5-membered heteroaryl include pyrrole, imidazole, and pyrazole.

In other embodiments, optionally in combination with any other embodiment, $Cy^{1D}$ is substituted by one $R^{1D}$ that itself is optionally substituted $C_6$-$C_{10}$-aryl. Alternatively, $Cy^{2D}$ is substituted by one $R^{2D}$ that is optionally substituted $C_6$-$C_{10}$-aryl. Exemplary aryl groups include phenyl and naphthyl.

Specific examples of Formula IV compounds are presented in Table 4 as set forth below.

Pharmaceutical Composition

The disclosure also provides a pharmaceutical composition comprising a therapeutically effective amount of one or more compounds according to any of Formula I-VI or a pharmaceutically acceptable salt, solvate, stereoisomer, tautomer, or prodrug, in admixture with a pharmaceutically acceptable carrier. In some embodiments, the composition further contains, in accordance with accepted practices of pharmaceutical compounding, one or more additional therapeutic agents, pharmaceutically acceptable excipients, diluents, adjuvants, stabilizers, emulsifiers, preservatives, colorants, buffers, flavor imparting agents.

In one embodiment, the pharmaceutical composition comprises a compound selected from those illustrated in Tables 1-4 or a pharmaceutically acceptable salt, solvate, stereoisomer, tautomer, or prodrug thereof, and a pharmaceutically acceptable carrier.

The pharmaceutical composition of the present disclosure is formulated, dosed, and administered in a fashion consistent with good medical practice. Factors for consideration in this context include the particular disorder being treated, the particular subject being treated, the clinical condition of the subject, the cause of the disorder, the site of delivery of the agent, the method of administration, the scheduling of administration, and other factors known to medical practitioners.

The "therapeutically effective amount" of the compound that is administered is governed by such considerations, and is the minimum amount necessary to exert a cytotoxic effect on a mesenchymally-derived or mesenchymally-transformed cancer. Such amount may be below the amount that is toxic to normal cells, or the subject as a whole. Generally, the initial therapeutically effective amount of the compound of the present disclosure that is administered parenterally per dose is in the range of about 0.01-2000 mg/kg, for example about 0.01 to about 200 mg/kg, about 0.1 to 20 mg/kg of patient body weight per day, with the typical initial range of compound used being 0.3 to 15 mg/kg/day. Oral unit dosage forms, such as tablets and capsules, may contain from about 25 to about 200 mg of the compound of the present disclosure.

The inventive compositions can be administered orally, topically, parenterally, by inhalation or spray or rectally in dosage unit formulations. The term parenteral as used herein includes subcutaneous injections, intravenous, intramuscular, intrasternal injection, or infusion techniques.

Suitable oral compositions in accordance with the disclosure include without limitation tablets, troches, lozenges, aqueous or oily suspensions, dispersible powders or granules, emulsion, hard or soft capsules, syrups or elixirs.

Encompassed within the scope of the disclosure are pharmaceutical compositions suitable for single unit dosages that comprise a compound of the disclosure or its pharmaceutically acceptable stereoisomer, prodrug, salt, solvate, hydrate, or tautomer and a pharmaceutically acceptable carrier.

Inventive compositions suitable for oral use may be prepared according to any method known to the art for the manufacture of pharmaceutical compositions. For instance, liquid formulations of the present compounds contain one or more agents selected from the group consisting of sweetening agents, flavoring agents, coloring agents and preserving agents in order to provide pharmaceutically elegant and palatable preparations of the arginase inhibitor.

For tablet compositions, the compound in admixture with non-toxic pharmaceutically acceptable excipients is used for the manufacture of tablets. Examples of such excipients include without limitation inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

For aqueous suspensions the inventive compound is admixed with excipients suitable for maintaining a stable suspension. Examples of such excipients include without limitation are sodium carboxymethylcellulose, methylcellulose, hydropropylmethylcellulose, sodium alginate, polyvinylpyrrolidone, gum tragacanth and gum acacia.

Oral suspensions can also contain dispersing or wetting agents, such as naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the disclosure may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and conden-saturatedion products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable, an aqueous suspension or an oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formulae I-VI may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compositions for parenteral administrations are administered in a sterile medium. Depending on the vehicle used and concentration the concentration of the drug in the formulation, the parenteral formulation can either be a suspension or a solution containing dissolved drug. Adjuvants such as local anesthetics, preservatives and buffering agents can also be added to parenteral compositions.

Methods of Use

Cancer cells that are derived from mesenchymal tissues or that are induced to adopt a cancer stem cell-like mesenchymal state have been demonstrated to be largely resistant to standard chemotherapies, necessitating the identification of new effective treatment strategies. Demonstrated by the appended examples, the Formula I-IV compounds irreversibly inhibit the growth of mesenchymally transformed cancer cells.

Accordingly, in an embodiment of present disclosure there is provided a method for treating a patient cancer suffering from a mesenchymally-derived or mesenchymally-transformed cancer. The method comprises administering to the subject a therapeutically effective amount of a compound, or a pharmaceutically acceptable salt thereof, according to any one of Formulae I-IV as described herein.

In some embodiments, the cancer is a breast cancer. Various breast cancers include ductal carcinoma in situ, invasive ductal carcinoma, lobular carcinoma. For example, the present methods are particularly effective inhibiting triple-negative breast cancer.

In other embodiments, the cancer is a sarcoma. Illustrative sarcomas include Askin's tumor, sarcoma botryoides, chondrosarcoma, Ewing's sarcoma, malignant hemangioendothelioma, malignant Schwannoma, and osteosarcoma. The sarcoma also can be a soft tissue sarcoma, including alveolar soft part sarcoma, angiosarcoma, cystosarcoma Phyllodes, dermatofibrosarcoma protuberans, desmoid tumor, desmoplastic small round cell tumor, epithelioid sarcoma, extraskeletal chondrosarcoma, extraskeletal osteosarcoma, fibrosarcoma, gastrointestinal stromal tumor, hemangiopericytoma ("solitary fibrous tumor"), angiosarcoma, Kaposi's sarcoma, leiomyosarcoma, liposarcoma, lymphangiosarcoma, malignant peripheral nerve sheath tumor (MPNST), neurofibrosarcoma, Rhabdomyosarcoma, synovial sarcoma, and undifferentiated pleomorphic sarcoma.

Another embodiment provides a method for selectively inhibiting FOXC2-expressing breast cancer stem cells. The method comprises contacting the cells with an effective amount of a compound, or a pharmaceutically acceptable salt thereof, according to any one of Formulae I-IV as described herein. The contacting occurs in vivo. Alternatively, in accordance with an embodiment, the contacting occurs in vitro or ex vivo.

Compounds of the present disclosure chemically target the intermediate filament protein, vimentin, and the compounds therefore promote mitotic catastrophe, such as in mesenchymally-derived or mesenchymally-transformed cancers. The compounds also are useful in treating diseases or conditions that are characterized by the expression of vimentin (K. M. Ridge et al., *Methods Enzymol.* 568 (2016) 389-426). The diseases and conditions include inflammatory diseases (G. Dos Santos et al., *Nature Communications* 6 (2015) 6574) such as Crohn's disease (C. Stevens et al., *Gut* 62(5) (20123) 695-707), cancers such as lung cancer (M. E. Kidd et al., *American Journal of Respiratory Cell and Molecular Biology* 50(1) (2014) 1-6), congenital cataracts (M. Muller et al., *Human Molecular Genetics* 18(6) (2009) 1052-1057), and neuropathies such as giant axonal neuropathy (GAN) (S. Mahammad et al., *Journal of Clinical Investigation* 123(5) (2013) 1964-1975).

EXAMPLES

The present disclosure will be additionally understood by reference to the following examples. The examples should not, however, be construed as limiting the scope of the present disclosure.

Example 1: High Throughput Screen Identifies Selective Inhibitors of FOXC2-Expressing Cells An engineered cancer cell line HMLER as an isogenic screening system was employed to identify compounds that are selectively toxic to the FOXC2 positive genotype. HMLER cells are derived from mammary epithelial cells (HMECs), but are virally transformed with the K-Ras oncogene (G12V), human telomerase reverse transcriptase (hTERT), and SV40 large-T antigen (B. Elenbaas, B. et al. Genes Dev. 15 (2001) 50-65). Expression of these genes endows HMLER cells with functional immortality and tumorigenic potential at high seeding number (>$10^6$ cells; Hollier (2013)). HMLER cells retain epithelial characteristics and sensitivity to various EMT-inducing stimuli (e.g. TGF-β1) and have historically been used to investigate the effects of single EMT related genes on cancer stemness (Mani (2008)). Further, retroviral expression of FOXC2 endows these cells with metastatic potential and the properties of stem cells, including the ability to form mammospheres, resist conventional chemotherapeutic agents, and form tumors at limiting dilutions ($10^3$ cells; Hollier (2013)). This example thus employed FOXC2-expressing HMLER cells (designated FOXC2-HMLER throughout) that were generated using retroviral transgene delivery, with the isogenic HMLER cell line as a control (Hollier (2013)).

Cell Lines:

The propagation conditions and generation of FOXC2-HMLER, HMLER, SNAIL-HMLER, SNAIL-HMLE, and SUM159 cells have been described previously (Mani (2008)). MCF-7, HepG2, HCT116, and MDA-MB-231 cells were from ATCC and maintained in DMEM medium (Corning) supplemented with 10% FBS (Corning) with Anti-anti (Gibco). The soft tissue sarcoma cell line panel was purchased from ATCC (TCP-1019) and maintained in the recommended medium for each cell type. HUVEC cells (pooled donor) were maintained in EBM-2 medium (both from Lonza Walkersville). Primary human lung fibroblasts were maintained in Fibroblast Medium (both from Sciencell Research Laboratories). For cell growth experiments, HLFs were grown in DMEM supplemented with 2% FBS and Anti-anti. For all experiments, primary human cells were used at a passage no greater than 4.

High Throughput Screening and Miniaturized Cell Viability Experiments:

For high throughput screening, FOXC2-HMLER and HMLER cells were plated at $10^3$ cells per well in white 384-well plates in 50 μL of MEGM medium (Lonza). Cells were allowed to attach for one hour before compound was transferred to each well as a DMSO solution using a 100 nL pintool head affixed to a PerkinElmer FX instrument. After 72-hour incubation, 30 μL of a Cell Titer Glo solution (diluted 1:6 in water, Promega) was dispensed into each well and luminance values were recorded using an Envision plate reader. Compounds which decreased viability of FOXC2-HMLER cells three Z scores below plate mean but did not decrease control HMLER viability more than one Z score below plate mean were deemed primary screening hits. Selected hit compounds were reordered from ChemDiv and tested for selective toxicity in 10-point response assays as above. All other miniaturized, selective viability experiments were performed as above using the indicated growth medium.

More specifically, in the high throughput screening assay above, each cell line was plated at 1,000 cells per well in 384-well plates, treated for 72 hours with 2 μM of test compound, and the viability of each line was determined in parallel by Cell Titer Glo (Promega) luminance measurements. The screen employed a library of ~50,000 diverse heterocyclic compounds and biologically active small molecules (ChemDiv, San Diego, Calif., USA) for cytotoxic activity against both cell lines.

Preliminary screening of the compounds revealed that FOXC2-HMLER cells were largely resistant to most chemotherapies tested. For comparison, the commonly used chemotherapy drug doxorubicin (Fisher Scientific) displays modest preferential toxicity to control HMLER cells ($IC_{50}$ 267 nM) relative to FOXC2-HMLER cells ($IC_{50}$ 447 nM). These results were consistent with the notion that these cells represent a cancer stem cell population.

This screening campaign led to the identification of Formulae I-IV compounds that selectively inhibit the growth of FOXC2-expressing HMLER cells at sub-micromolar doses while displaying minimal toxicity to vector control HMLER cells or to non-transformed human mammary epithelial cells (HMECs) at doses up to 20 μM (see FIG. 1).

Results of the screen are presented in Tables 1 to 4 below, corresponding to compounds of Formulae I-IV, respectively. Activities of the compounds are scored in relation to the activities of "parent" compounds in each table, i.e., those labeled as compounds 1, 2, 3, and 4, as follows:

| Activity score | Activity |
|---|---|
| +++ | More potent than parent |
| ++ | $IC_{50}$ < 1 μM; similar activity to parent |
| + | 20 μM > $IC_{50}$ > 1 μM; less potent than parent |
| − | $IC_{50}$ > 20 μM; no detectable activity |

TABLE 1

Inhibition of FOXC2-expressing HMLER cells by Formula I Compounds

| Compound No. | Structure | Activity Score |
|---|---|---|
| 1 | (Cl-substituted cinnoline linked via piperazine to chlorophenyl) | ++ |

TABLE 1-continued

Inhibition of FOXC2-expressing HMLER cells by Formula I Compounds

| Compound No. | Structure | Activity Score |
|---|---|---|
| 1A | 8-chloro-4-(3,5-dimethylpiperidin-1-yl)cinnoline | + |
| 1B | 2-(3,4-dimethylphenyl)-4-(4-phenylpiperazin-1-yl)pyrazolo[1,5-a]pyrazine | + |
| 1C | 2-phenyl-4-(4-(p-tolyl)piperazin-1-yl)pyrazolo[1,5-a]pyrazine | + |
| 1D | 3-(4-(3-chlorophenyl)piperazin-1-yl)quinoxaline | + |
| 1E | 3-chloro-6-(4-(2-chlorophenyl)piperazin-1-yl)pyridazine | − |
| 1F | 2-(4-chlorophenyl)-4-(4-(4-methoxyphenyl)piperazin-1-yl)pyrazolo[1,5-a]pyrazine | − |
| 1G | 7-chloro-4-(piperazin-1-yl)quinoline | − |
| 1SRH | 8-chloro-4-(4-(3,5-dichlorophenyl)piperazin-1-yl)cinnoline | +++ |

TABLE 1-continued

Inhibition of FOXC2-expressing HMLER cells by Formula I Compounds

| Compound No. | Structure | Activity Score |
|---|---|---|
| 1SRI | (8-chlorocinnolin-4-yl)-piperazine-(3,5-dichloro-4-fluorophenyl) | + |
| 1SRJ | (8-chlorocinnolin-4-yl)-piperazine-(3-chloro-4-fluorophenyl) | + |
| 1SRK | (8-chlorocinnolin-4-yl)-piperazine-(2-fluoro-3-chlorophenyl) | + |
| 1SRL | (8-chlorocinnolin-4-yl)-2-methylpiperazine-(3,5-dichlorophenyl) | ++ |
| 1SRM | (8-chlorocinnolin-4-yl)-3-methylpiperazine-(3,5-dichlorophenyl) | ++ |
| 1SRN | (cinnolin-4-yl)-piperazine-(3,5-dichlorophenyl) | ++ |

TABLE 1-continued
Inhibition of FOXC2-expressing HMLER cells by Formula I Compounds
| Compound No. | Structure | Activity Score |
|---|---|---|
| 1SRO | 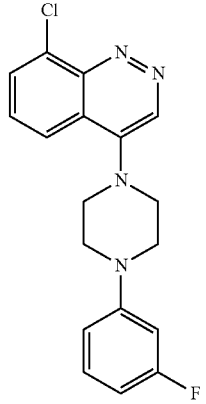 [SMILES: Fc1cccc(N2CCN(c3cnnc4c(Cl)cccc34)CC2)c1] | + |
| 1SRP | 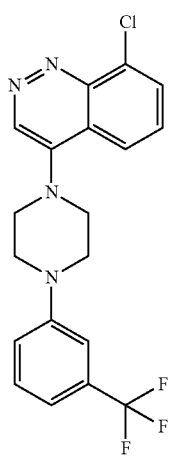 | + |
| 1SRQ | 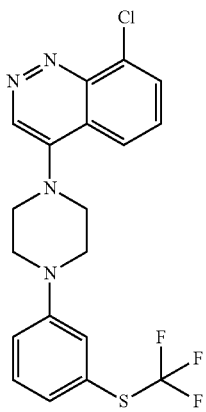 | + |
| 1SRU | 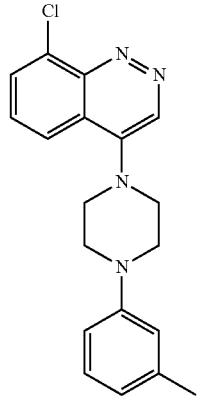 | + |
| 1SRT | 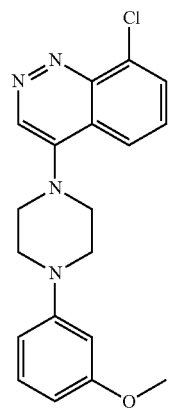 [SMILES: COc1cccc(N2CCN(c3cnnc4c(Cl)cccc34)CC2)c1] | ++ |
| 1SRU | 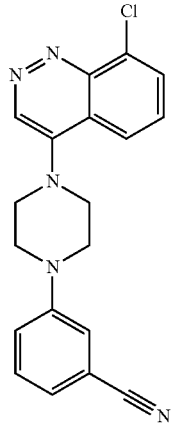 | ++ |

TABLE 1-continued

Inhibition of FOXC2-expressing HMLER cells by Formula I Compounds

| Compound No. | Structure | Activity Score |
|---|---|---|
| 1SRV | 8-chlorocinnoline-4-yl piperazine with 3-carboxamidophenyl | + |
| 1SRW | 8-chlorocinnoline-4-yl piperazine with 2-chlorophenyl | + |
| 1SRX | 8-chlorocinnoline-4-yl piperazine with phenyl | − |
| 1SRY | 8-chlorocinnoline-4-yl piperazine with 4-chlorophenyl | − |
| 1SRZ | 8-chlorocinnoline-4-yl piperazine with 2,3-dichlorophenyl | − |
| 1SRAA | 8-chlorocinnoline-4-yl piperazine with 3,4-dichlorophenyl | + |

TABLE 1-continued

Inhibition of FOXC2-expressing HMLER cells by Formula I Compounds

| Compound No. | Structure | Activity Score |
|---|---|---|
| 1SRAB | 8-chloro-4-[4-(2,5-dichlorophenyl)piperazin-1-yl]cinnoline | + |
| 1SRAC | 8-chloro-4-{4-[3-(trifluoromethoxy)phenyl]piperazin-1-yl}cinnoline | + |
| 1SRAD | 8-chloro-4-[4-(6-chloropyridin-2-yl)piperazin-1-yl]cinnoline | + |
| 1SRAE | 8-chloro-4-[4-(2-chloropyrimidin-4-yl)piperazin-1-yl]cinnoline | − |
| 1SRAF | 8-chloro-4-[4-(6-chloropyrazin-2-yl)piperazin-1-yl]cinnoline | − |
| 1SRAG | 8-chloro-4-[4-(3-chloro-5-fluorophenyl)piperazin-1-yl]cinnoline | ++ |

TABLE 1-continued

Inhibition of FOXC2-expressing HMLER cells by Formula I Compounds

| Compound No. | Structure | Activity Score |
|---|---|---|
| 1SRAH | *8-chlorocinnoline-4-yl piperazine linked to 3-chloro-5-methoxyphenyl* | +++ |
| 1SRAI | *8-chlorocinnoline-4-yl piperazine linked to 3-chloro-5-methylphenyl* | ++ |
| 1SRAJ | *8-chlorocinnoline-4-yl piperazine linked to 3-chloro-5-(trifluoromethyl)phenyl* | + |
| 1SRAK | *8-chlorocinnoline-4-yl piperazine linked to 3-chloro-5-cyanophenyl* | ++ |
| 1SRAL | *8-chlorocinnoline-4-yl piperazine linked to 3,5-dichloro-4-methylphenyl* | + |
| 1SRAM | *8-chlorocinnoline-4-yl piperazine linked via sulfonyl to 1-(difluoromethyl)-5-methyl-1H-pyrazol-4-yl* | − |

TABLE 1-continued

Inhibition of FOXC2-expressing HMLER cells by Formula I Compounds

| Compound No. | Structure | Activity Score |
|---|---|---|
| 1SRAN | [structure: 8-chloro-cinnoline linked to a diazabicyclic diamine bearing a 3,5-dichlorophenyl group] | ++ |

TABLE 2

Inhibition of FOXC2-expressing HMLER cells by Formula II Compounds

| Compound No. | Structure | Activity Score |
|---|---|---|
| 2A | [structure: dioxino-fused quinolinone with (4-ethylphenyl)aminomethyl substituent and N-(2,6-dimethylphenyl)acetamide on ring nitrogen] | +++ |
| 2 | [structure: 7-methoxy-2-oxoquinoline with 3-((phenylamino)methyl) group, N-substituted with acetamide linked to methyl 2-aminobenzoate] | ++ |

TABLE 2-continued

Inhibition of FOXC2-expressing HMLER cells by Formula II Compounds

| Compound No. | Structure | Activity Score |
|---|---|---|
| 2B | 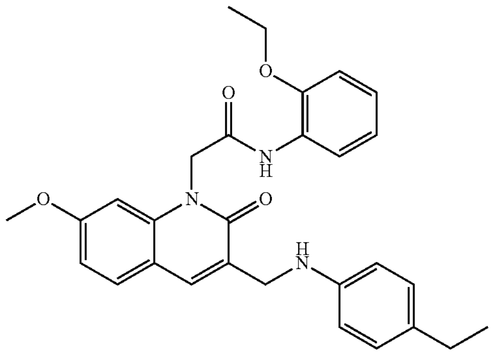 [SMILES: CCOc1ccccc1NC(=O)Cn1c(=O)c(CNc2ccc(CC)cc2)cc2ccc(OC)cc21] | ++ |
| 2C | 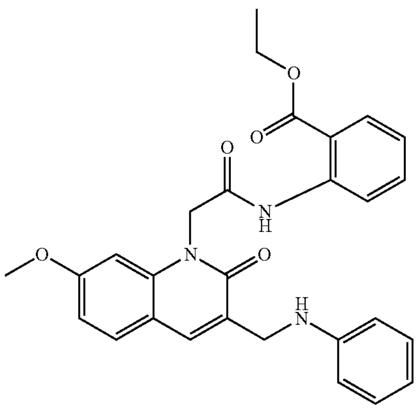 [SMILES: CCOC(=O)c1ccccc1NC(=O)Cn1c(=O)c(CNc2ccccc2)cc2ccc(OC)cc21] | ++ |
| 2D | 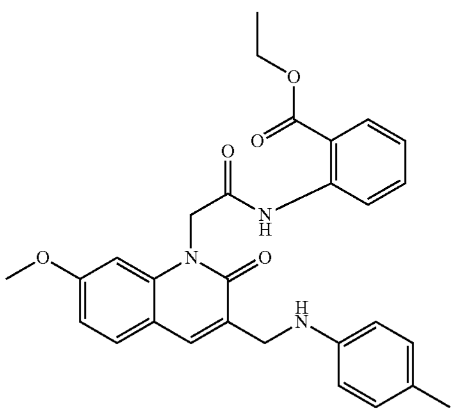 | + |
| 2E | 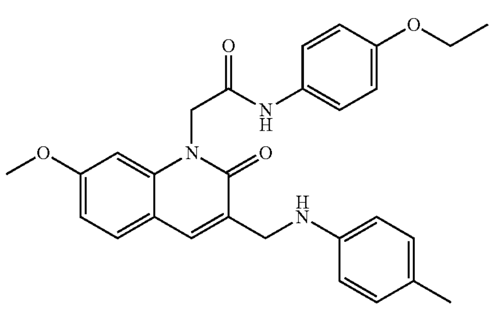 [SMILES: CCOc1ccc(NC(=O)Cn2c(=O)c(CNc3ccc(C)cc3)cc3ccc(OC)cc32)cc1] | + |

TABLE 2-continued

Inhibition of FOXC2-expressing HMLER cells by Formula II Compounds

| Compound No. | Structure | Activity Score |
|---|---|---|
| 2F | 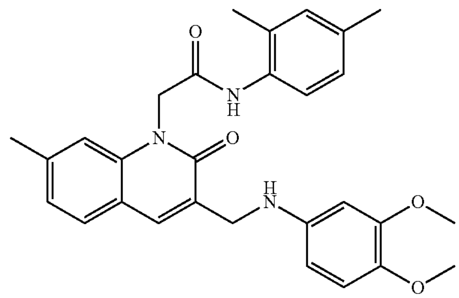 | + |
| 2G | 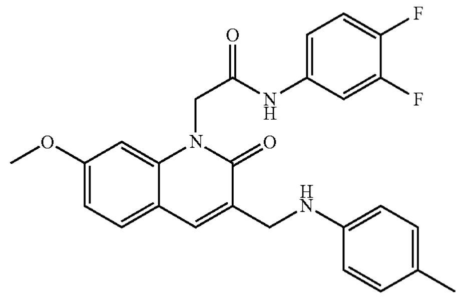 | + |
| 2H | 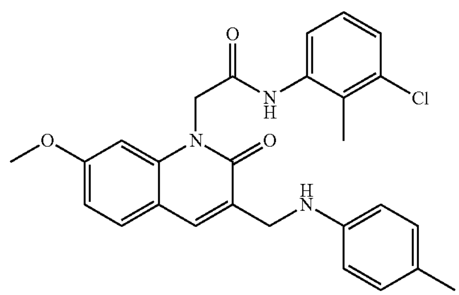 | + |
| 2I | 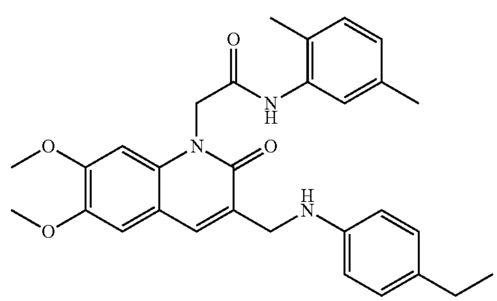 [SMILES: CCc1ccc(NCc2cc3cc(OC)c(OC)cc3n(CC(=O)Nc3cc(C)ccc3C)c2=O)cc1] | + |
| 2J | 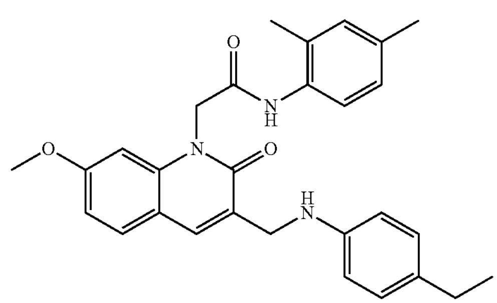 [SMILES: CCc1ccc(NCc2cc3ccc(OC)cc3n(CC(=O)Nc3ccc(C)cc3C)c2=O)cc1] | + |

TABLE 2-continued

Inhibition of FOXC2-expressing HMLER cells by Formula II Compounds

| Compound No. | Structure | Activity Score |
|---|---|---|
| 2K | 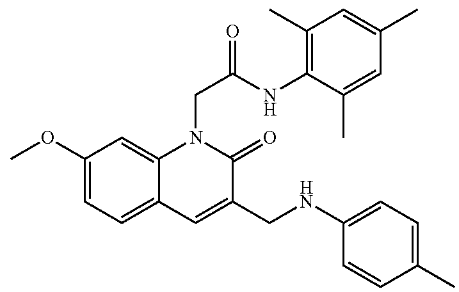 | + |
| 2L | 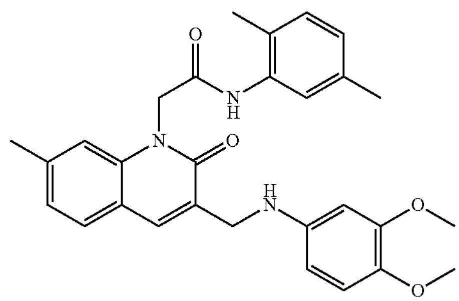 | + |
| 2M | 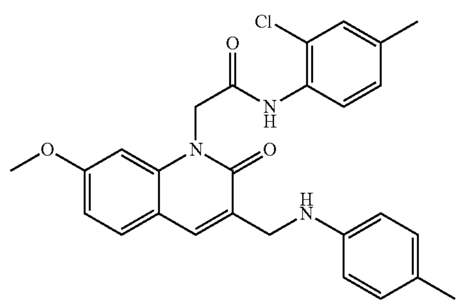 | + |
| 2N | 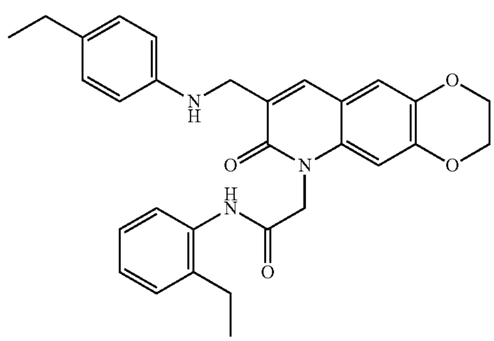 [SMILES: CCc1ccc(NCc2cc3cc4c(cc3n(CC(=O)Nc3ccccc3CC)c2=O)OCCO4)cc1] | + |
| 2O | 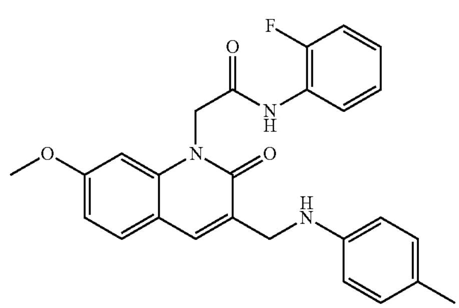 | + |

TABLE 2-continued
Inhibition of FOXC2-expressing HMLER cells by Formula II Compounds
| Compound No. | Structure | Activity Score |
|---|---|---|
| 2P | 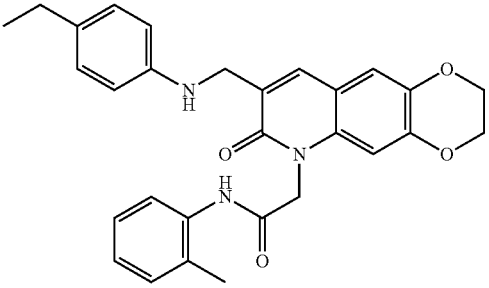 [SMILES: CCc1ccc(NCc2cc3cc4c(cc3n(CC(=O)Nc3ccccc3C)c2=O)OCCO4)cc1] | + |
| 2Q | 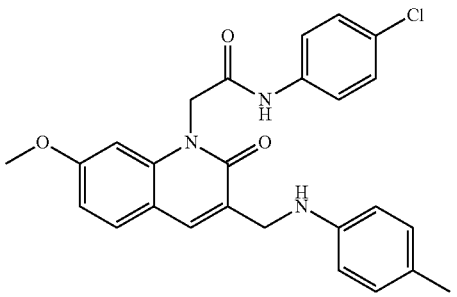 | + |
| 2R | 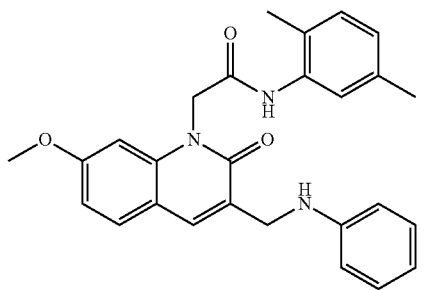 | + |
| 2S | 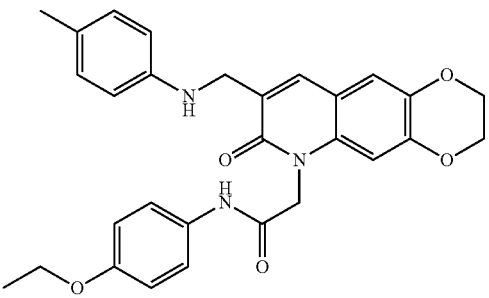 [SMILES: CCOc1ccc(NC(=O)Cn2c(=O)c(CNc3ccc(C)cc3)cc3cc4c(cc32)OCCO4)cc1] | + |
| 2T | 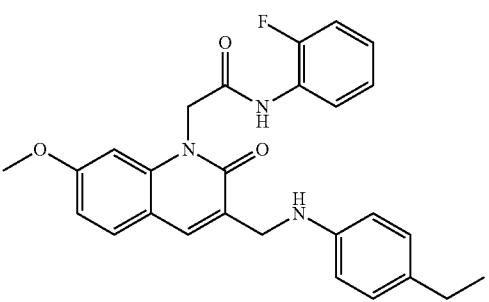 [SMILES: CCc1ccc(NCc2cc3ccc(OC)cc3n(CC(=O)Nc3ccccc3F)c2=O)cc1] | + |

TABLE 2-continued

Inhibition of FOXC2-expressing HMLER cells by Formula II Compounds

| Compound No. | Structure | Activity Score |
|---|---|---|
| 2U | *structure* | + |
| 2V | *structure* | + |
| 2W | *structure* | + |
| 2X | *structure* | + |
| 2Y | *structure* | + |

TABLE 2-continued
Inhibition of FOXC2-expressing HMLER cells by Formula II Compounds
| Compound No. | Structure | Activity Score |
|---|---|---|
| 2Z | 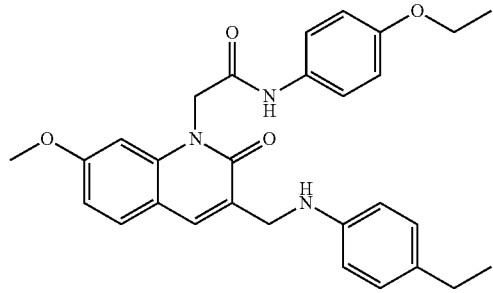 [SMILES: CCOc1ccc(NC(=O)Cn2c(=O)c(CNc3ccc(CC)cc3)cc3ccc(OC)cc32)cc1] | + |
| 2AA | 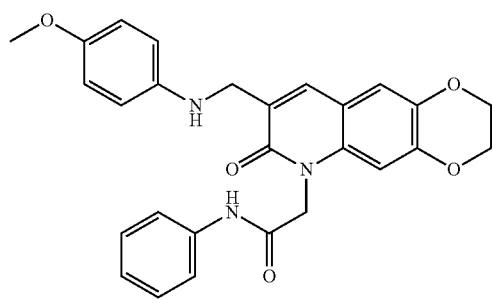 [SMILES: COc1ccc(NCc2cc3cc4c(cc3n(CC(=O)Nc3ccccc3)c2=O)OCCO4)cc1] | + |
| 2AB | 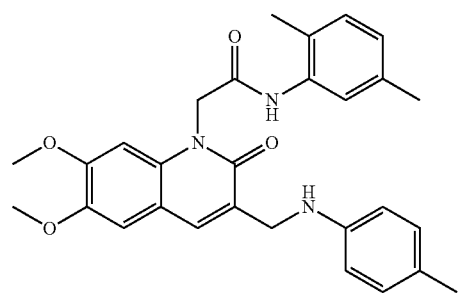 | + |
| 2AC | 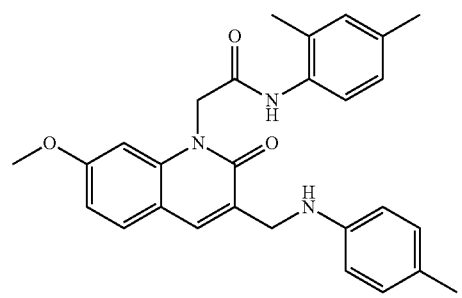 | + |

TABLE 2-continued

Inhibition of FOXC2-expressing HMLER cells by Formula II Compounds

| Compound No. | Structure | Activity Score |
|---|---|---|
| 2AD | 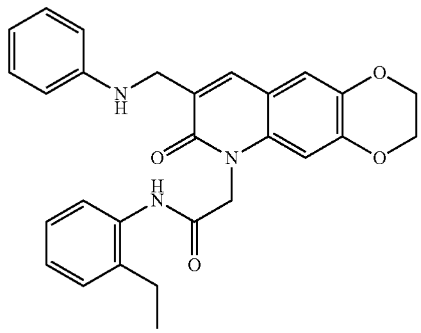 | + |
| 2AE | 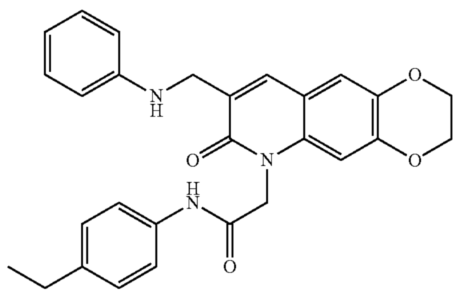 [SMILES: CCc1ccc(NC(=O)Cn2c(=O)c(CNc3ccccc3)cc3cc4c(cc32)OCCO4)cc1] | + |
| 2AF | 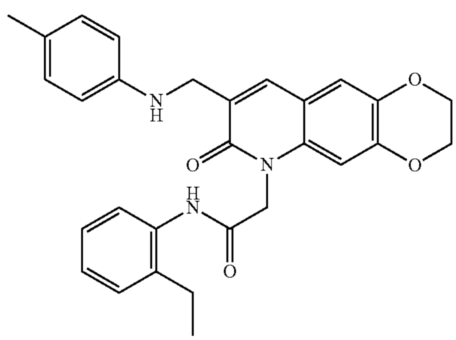 [SMILES: CCc1ccccc1NC(=O)Cn1c(=O)c(CNc2ccc(C)cc2)cc2cc3c(cc21)OCCO3] | + |
| 2AG | 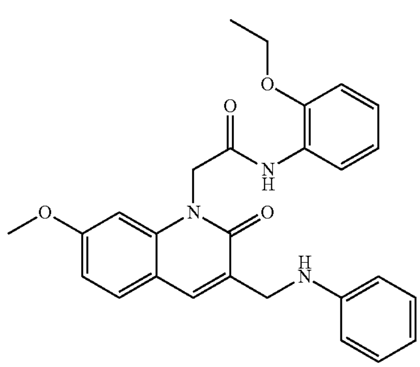 [SMILES: CCOc1ccccc1NC(=O)Cn1c(=O)c(CNc2ccccc2)cc2ccc(OC)cc21] | + |

TABLE 2-continued

Inhibition of FOXC2-expressing HMLER cells by Formula II Compounds

| Compound No. | Structure | Activity Score |
|---|---|---|
| 2AH | 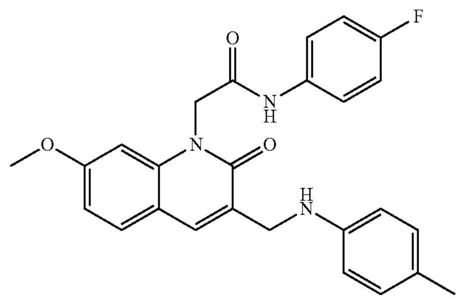 | + |
| 2AI | 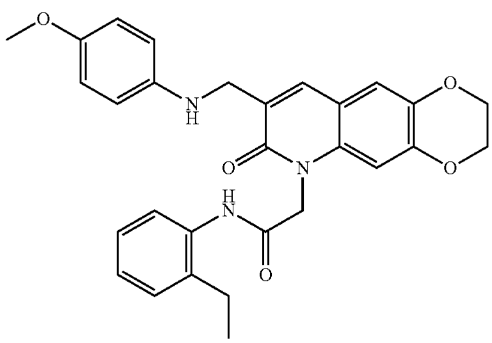 [SMILES: CCc1ccccc1NC(=O)Cn1c(=O)c(CNc2ccc(OC)cc2)cc2cc3c(cc21)OCCO3] | + |
| 2AJ | 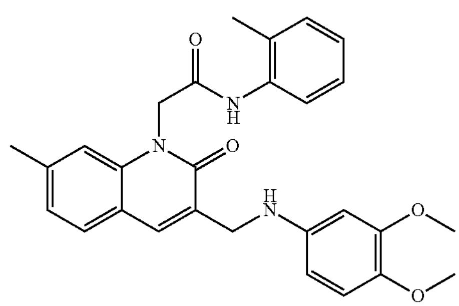 | + |
| 2AK | 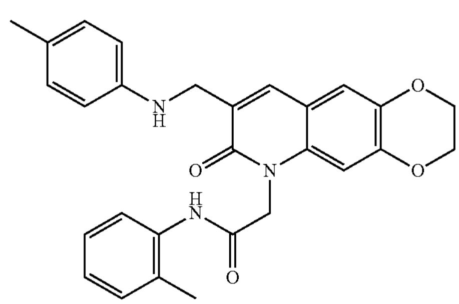 [SMILES: Cc1ccc(NCc2cc3cc4c(cc3n(CC(=O)Nc3ccccc3C)c2=O)OCCO4)cc1] | + |

TABLE 2-continued

Inhibition of FOXC2-expressing HMLER cells by Formula II Compounds

| Compound No. | Structure | Activity Score |
|---|---|---|
| 2AL | 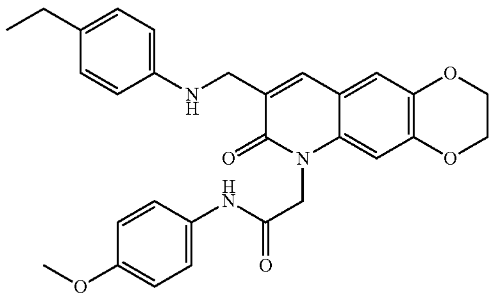 [SMILES: CCc1ccc(NCc2cc3cc4c(cc3n(CC(=O)Nc3ccc(OC)cc3)c2=O)OCCO4)cc1] | + |
| 2AM | 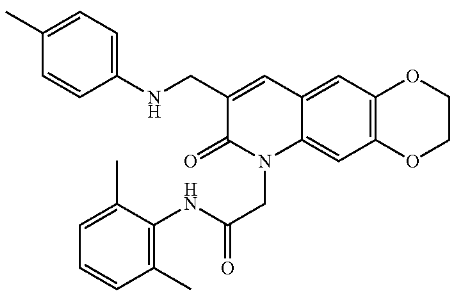 [SMILES: Cc1ccc(NCc2cc3cc4c(cc3n(CC(=O)Nc3c(C)cccc3C)c2=O)OCCO4)cc1] | + |
| 2AN | 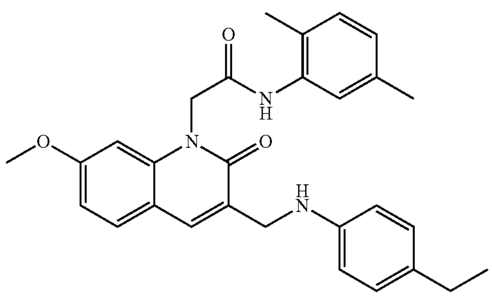 [SMILES: CCc1ccc(NCc2cc3ccc(OC)cc3n(CC(=O)Nc3cc(C)ccc3C)c2=O)cc1] | + |
| 2AO | 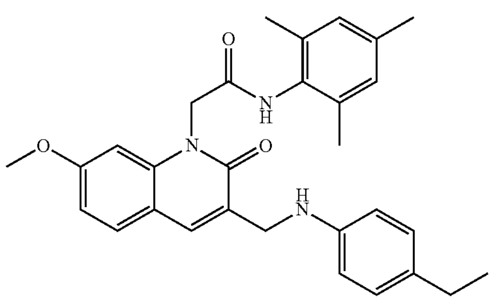 [SMILES: CCc1ccc(NCc2cc3ccc(OC)cc3n(CC(=O)Nc3c(C)cc(C)cc3C)c2=O)cc1] | + |
| 2AP | 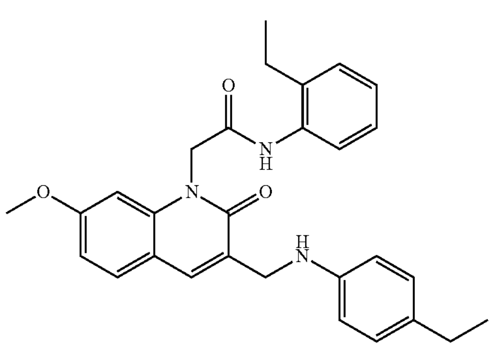 [SMILES: CCc1ccc(NCc2cc3ccc(OC)cc3n(CC(=O)Nc3ccccc3CC)c2=O)cc1] | + |

TABLE 2-continued

Inhibition of FOXC2-expressing HMLER cells by Formula II Compounds

| Compound No. | Structure | Activity Score |
|---|---|---|
| 2AQ | 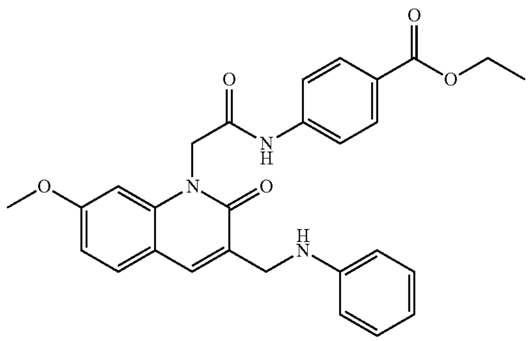 [SMILES: CCOC(=O)c1ccc(NC(=O)Cn2c(=O)c(CNc3ccccc3)cc3ccc(OC)cc32)cc1] | − |
| 2AR | 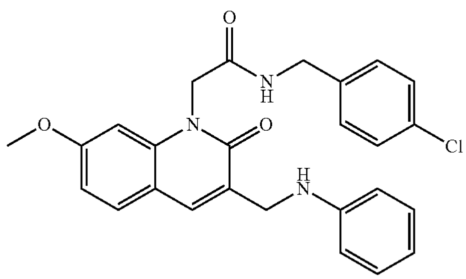 [SMILES: COc1ccc2cc(CNc3ccccc3)c(=O)n(CC(=O)NCc3ccc(Cl)cc3)c2c1] | − |
| 2AS | 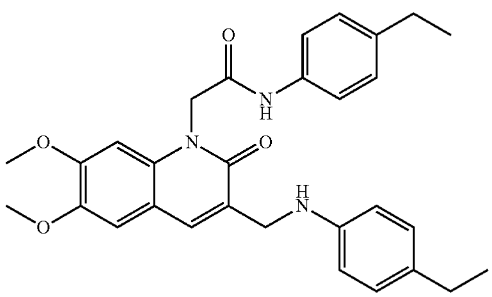 [SMILES: CCc1ccc(NCc2cc3cc(OC)c(OC)cc3n(CC(=O)Nc3ccc(CC)cc3)c2=O)cc1] | − |
| 2AT | 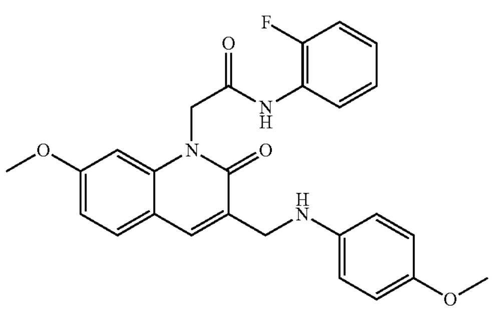 | − |
| 2AU | 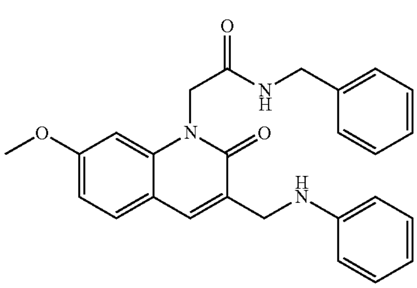 [SMILES: COc1ccc2cc(CNc3ccccc3)c(=O)n(CC(=O)NCc3ccccc3)c2c1] | − |

TABLE 2-continued

Inhibition of FOXC2-expressing HMLER cells by Formula II Compounds

| Compound No. | Structure | Activity Score |
|---|---|---|
| 2AV | 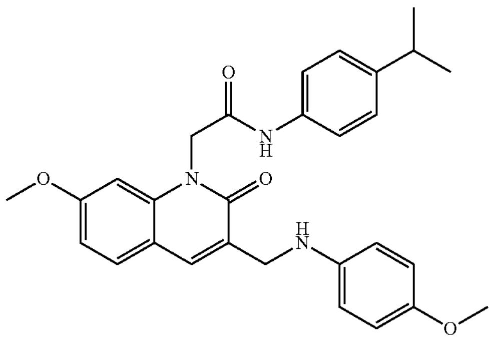 | − |
| 2AW | 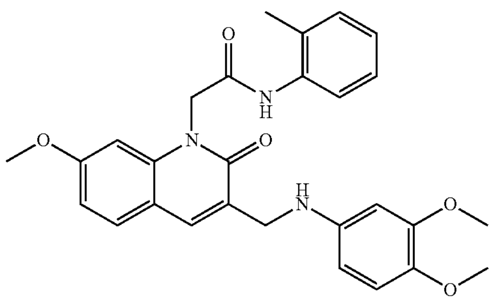 | − |
| 2AX | 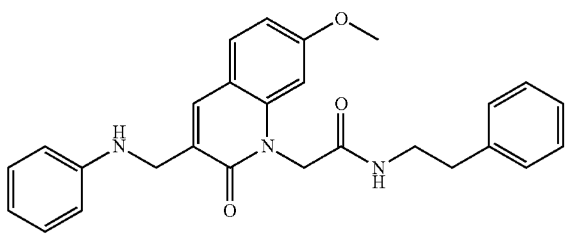 [SMILES: COc1ccc2cc(CNc3ccccc3)c(=O)n(CC(=O)NCCc3ccccc3)c2c1] | − |
| 2AY | 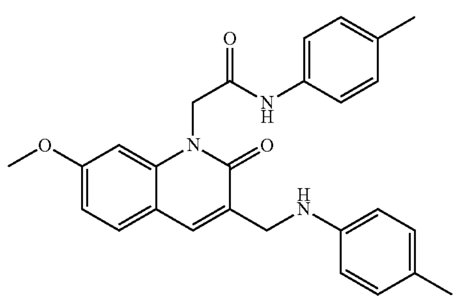 | − |
| 2AZ | 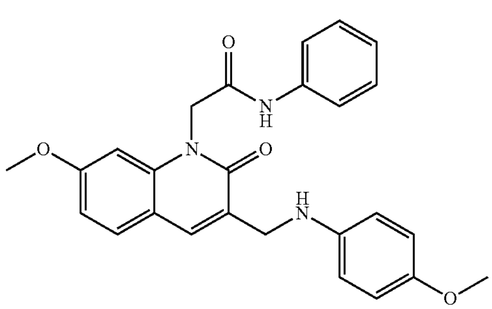 | − |

TABLE 2-continued

Inhibition of FOXC2-expressing HMLER cells by Formula II Compounds

| Compound No. | Structure | Activity Score |
|---|---|---|
| 2BA | 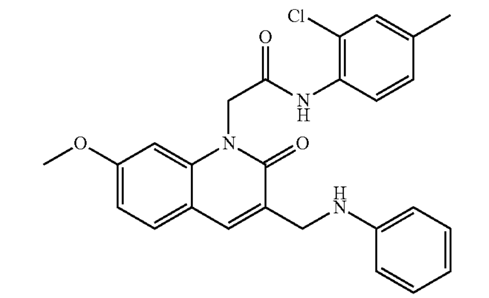 | − |
| 2BB | 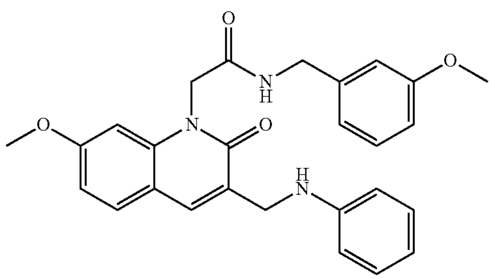 | − |
| 2BC | 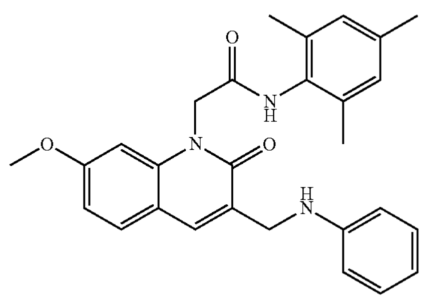 | − |
| 2BD | 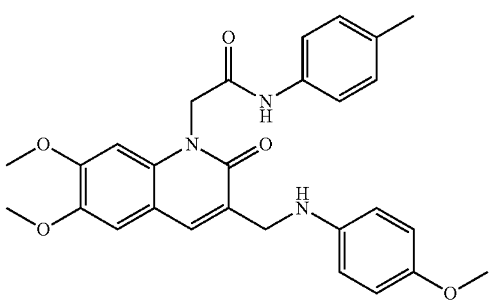 | − |
| 2BE | 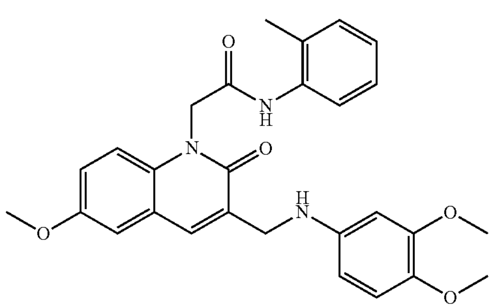 | − |

TABLE 2-continued

Inhibition of FOXC2-expressing HMLER cells by Formula II Compounds

| Compound No. | Structure | Activity Score |
|---|---|---|
| 2BF | 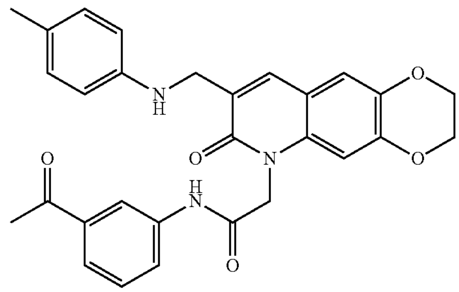 [SMILES: CC(=O)c1cccc(NC(=O)Cn2c(=O)c(CNc3ccc(C)cc3)cc3cc4c(cc32)OCCO4)c1] | − |
| 2BG | 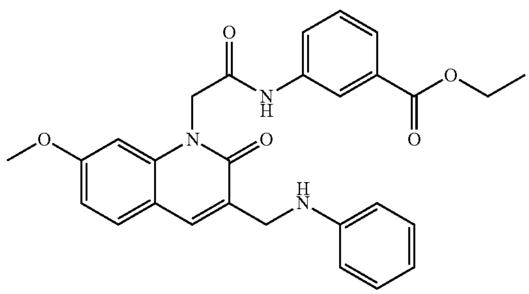 [SMILES: CCOC(=O)c1cccc(NC(=O)Cn2c(=O)c(CNc3ccccc3)cc3ccc(OC)cc32)c1] | − |
| 2BH | 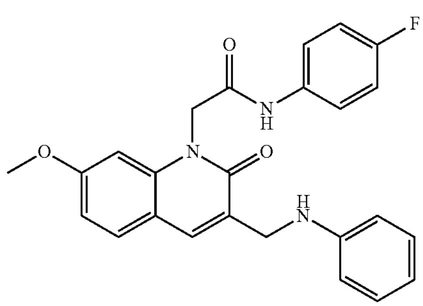 [SMILES: COc1ccc2cc(CNc3ccccc3)c(=O)n(CC(=O)Nc3ccc(F)cc3)c2c1] | − |
| 2BI | 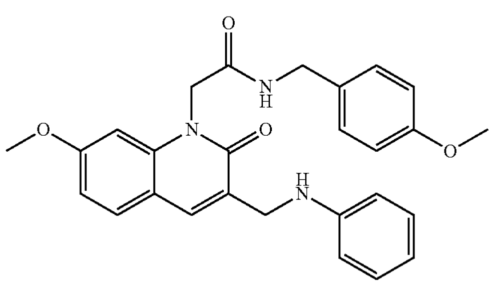 | − |
| 2BJ | 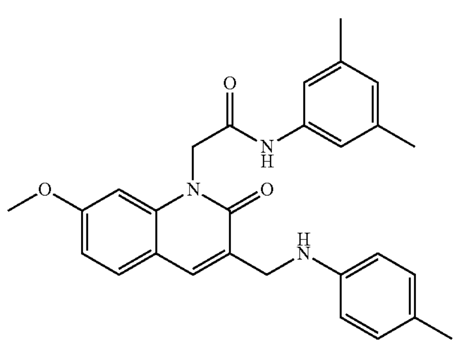 | − |

TABLE 2-continued

Inhibition of FOXC2-expressing HMLER cells by Formula II Compounds

| Compound No. | Structure | Activity Score |
|---|---|---|
| 2BK | 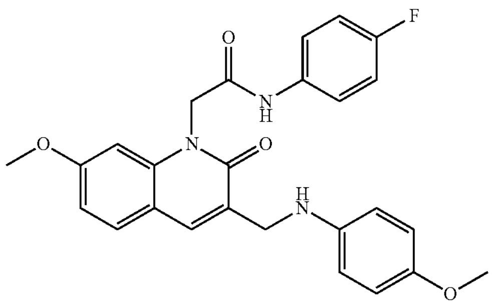 | − |
| 2BL | 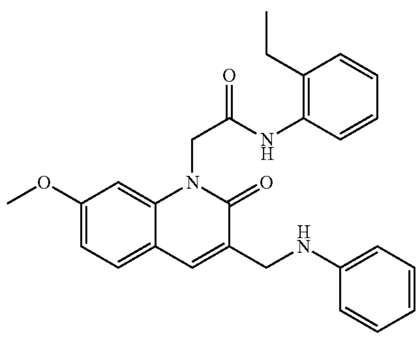 [SMILES: CCc1ccccc1NC(=O)Cn1c(=O)c(CNc2ccccc2)cc2ccc(OC)cc21] | − |
| 2BM | 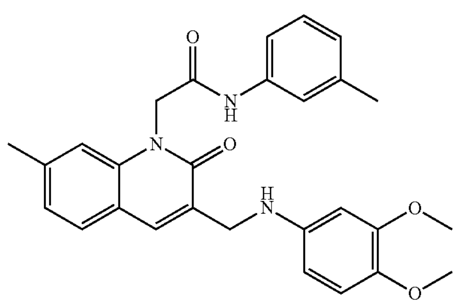 | − |
| 2BN | 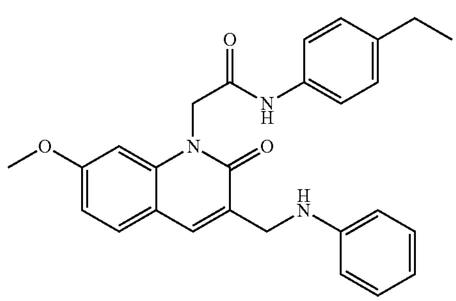 [SMILES: CCc1ccc(NC(=O)Cn2c(=O)c(CNc3ccccc3)cc3ccc(OC)cc32)cc1] | − |

TABLE 2-continued

Inhibition of FOXC2-expressing HMLER cells by Formula II Compounds

| Compound No. | Structure | Activity Score |
|---|---|---|
| 2BO | 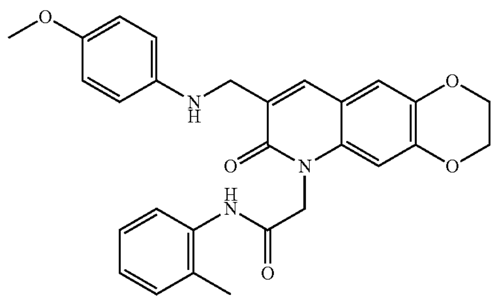 [SMILES: COc1ccc(NCc2cc3cc4c(cc3n(CC(=O)Nc3ccccc3C)c2=O)OCCO4)cc1] | − |
| 2BP | 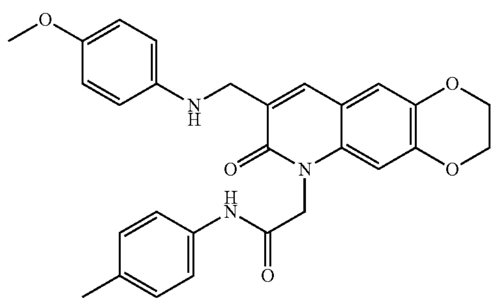 [SMILES: COc1ccc(NCc2cc3cc4c(cc3n(CC(=O)Nc3ccc(C)cc3)c2=O)OCCO4)cc1] | − |
| 2BQ | 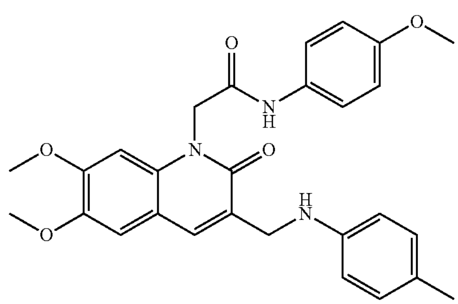 | − |
| 2BR | 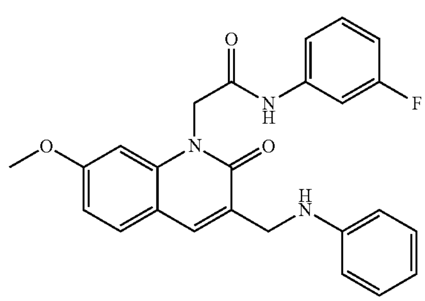 [SMILES: COc1ccc2cc(CNc3ccccc3)c(=O)n(CC(=O)Nc3cccc(F)c3)c2c1] | − |
| 2BS | 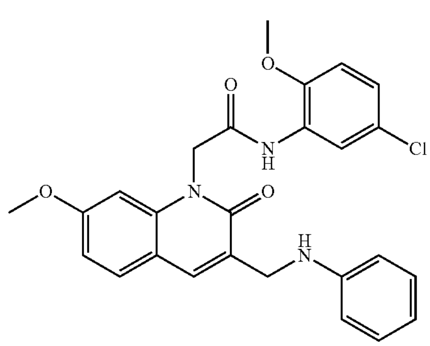 [SMILES: COc1ccc2cc(CNc3ccccc3)c(=O)n(CC(=O)Nc3cc(Cl)ccc3OC)c2c1] | − |

TABLE 2-continued

Inhibition of FOXC2-expressing HMLER cells by Formula II Compounds

| Compound No. | Structure | Activity Score |
|---|---|---|
| 2BT | 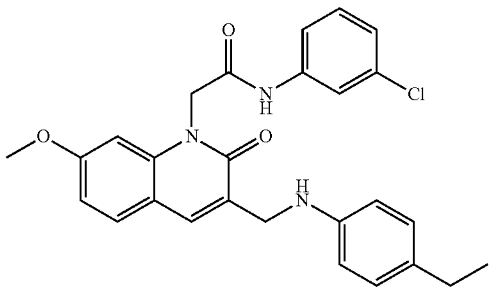 | − |
| 2BU | 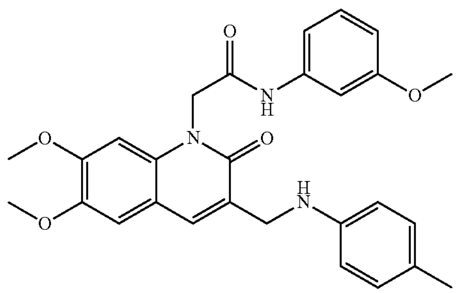 | − |
| 2BV | 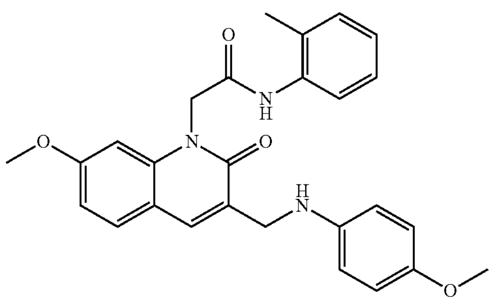 | − |
| 2BW | 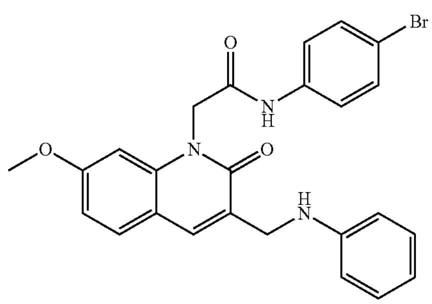 [SMILES: COc1ccc2cc(CNc3ccccc3)c(=O)n(CC(=O)Nc3ccc(Br)cc3)c2c1] | − |
| 2BX | 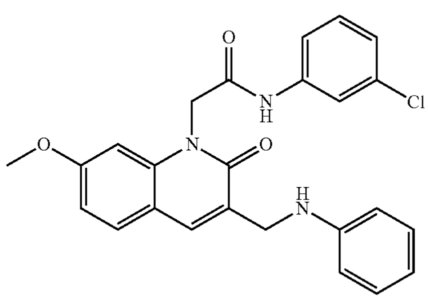 [SMILES: COc1ccc2cc(CNc3ccccc3)c(=O)n(CC(=O)Nc3cccc(Cl)c3)c2c1] | − |

TABLE 2-continued

Inhibition of FOXC2-expressing HMLER cells by Formula II Compounds

| Compound No. | Structure | Activity Score |
|---|---|---|
| 2BY | 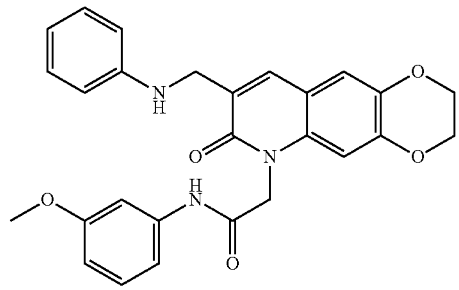 [SMILES: COc1cccc(NC(=O)Cn2c(=O)c(CNc3ccccc3)cc3cc4c(cc32)OCCO4)c1] | − |
| 2BZ | 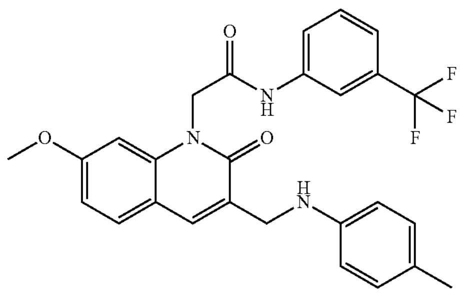 [SMILES: COc1ccc2cc(CNc3ccc(C)cc3)c(=O)n(CC(=O)Nc3cccc(C(F)(F)F)c3)c2c1] | − |
| 2CA | 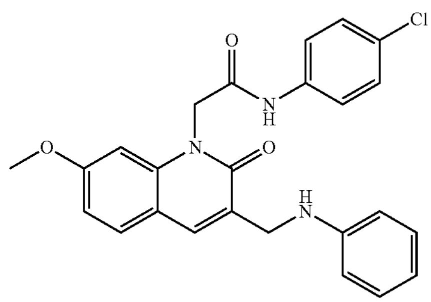 [SMILES: COc1ccc2cc(CNc3ccccc3)c(=O)n(CC(=O)Nc3ccc(Cl)cc3)c2c1] | − |
| 2CB | 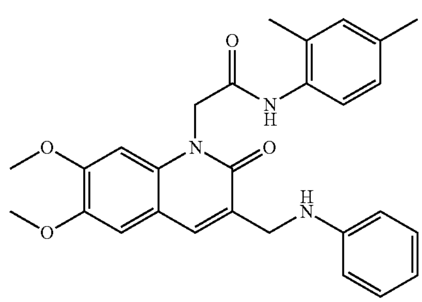 | − |
| 2CC | 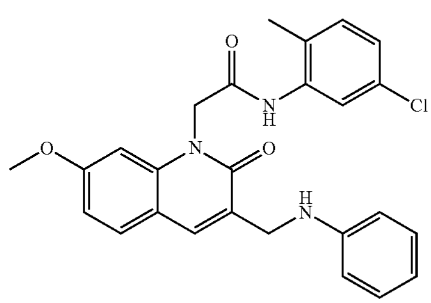 [SMILES: COc1ccc2cc(CNc3ccccc3)c(=O)n(CC(=O)Nc3cc(Cl)ccc3C)c2c1] | − |

TABLE 2-continued
Inhibition of FOXC2-expressing HMLER cells by Formula II Compounds
| Compound No. | Structure | Activity Score |
|---|---|---|
| 2CD | 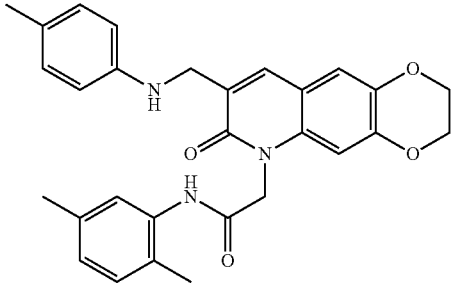 [SMILES: Cc1ccc(NCc2cc3cc4c(cc3n(CC(=O)Nc3cc(C)ccc3C)c2=O)OCCO4)cc1] | − |
| 2CE | 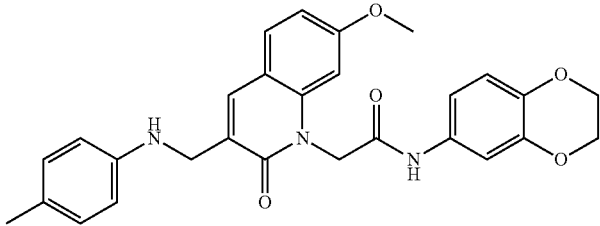 [SMILES: COc1ccc2cc(CNc3ccc(C)cc3)c(=O)n(CC(=O)Nc3ccc4c(c3)OCCO4)c2c1] | − |
| 2CF | 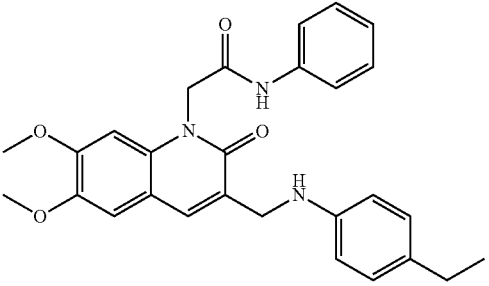 | − |
| 2CG | 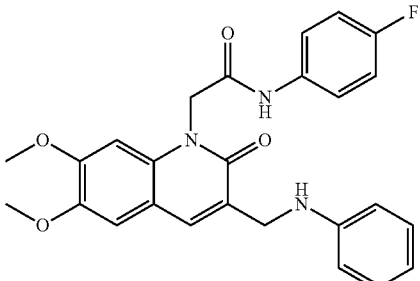 | − |
| 2CH | 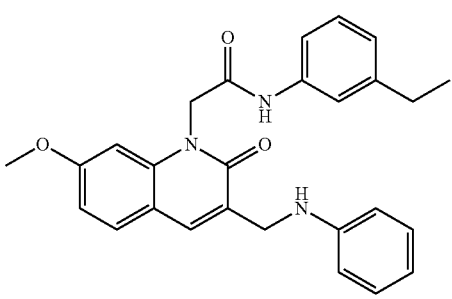 [SMILES: CCc1cccc(NC(=O)Cn2c(=O)c(CNc3ccccc3)cc3ccc(OC)cc32)c1] | − |

TABLE 2-continued

Inhibition of FOXC2-expressing HMLER cells by Formula II Compounds

| Compound No. | Structure | Activity Score |
|---|---|---|
| 2CI | 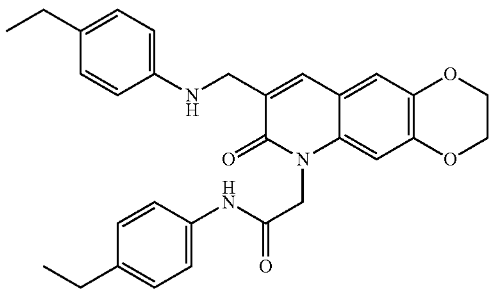 [SMILES: CCc1ccc(NCc2cc3cc4c(cc3n(CC(=O)Nc3ccc(CC)cc3)c2=O)OCCO4)cc1] | − |
| 2CJ | 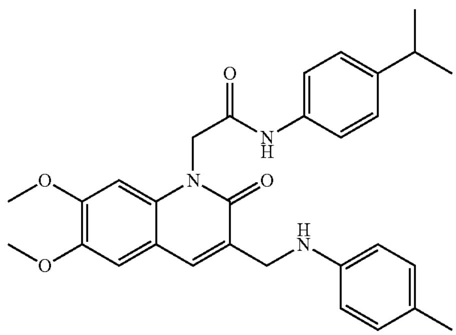 [SMILES: COc1cc2cc(CNc3ccc(C)cc3)c(=O)n(CC(=O)Nc3ccc(C(C)C)cc3)c2cc1OC] | − |
| 2CK | 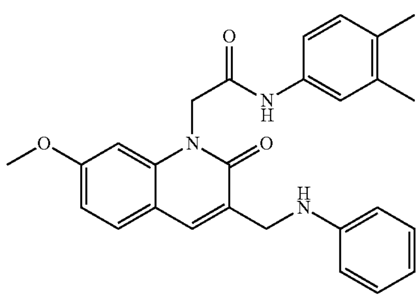 | − |
| 2CL | 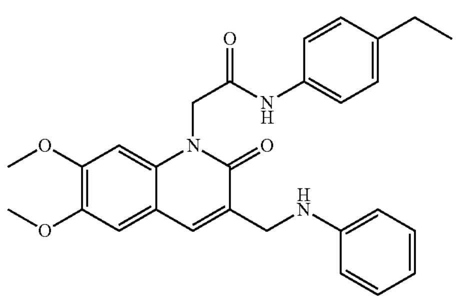 [SMILES: CCc1ccc(NC(=O)Cn2c(=O)c(CNc3ccccc3)cc3cc(OC)c(OC)cc32)cc1] | − |

TABLE 2-continued

Inhibition of FOXC2-expressing HMLER cells by Formula II Compounds

| Compound No. | Structure | Activity Score |
|---|---|---|
| 2CM | 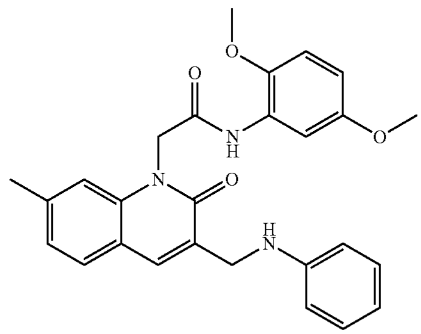 | − |
| 2CN | 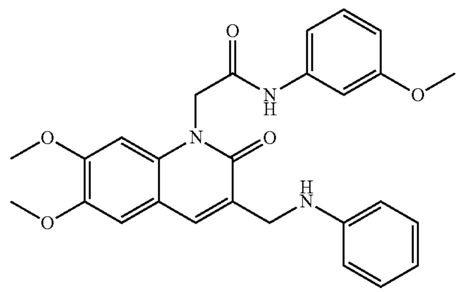 | − |
| 2CO | 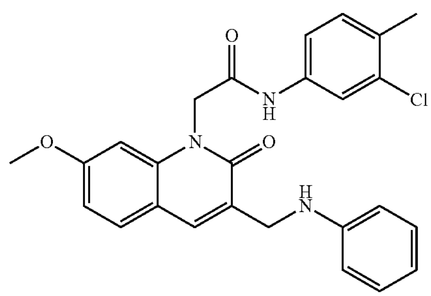 | − |
| 2CP | 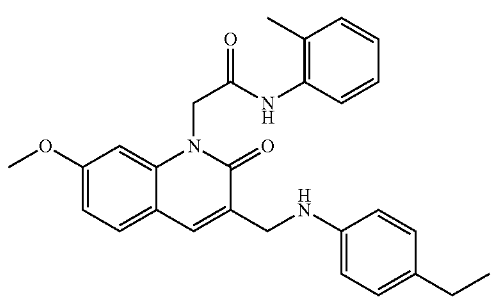 [SMILES: CCc1ccc(NCc2cc3ccc(OC)cc3n(CC(=O)Nc3ccccc3C)c2=O)cc1] | − |
| 2CQ | 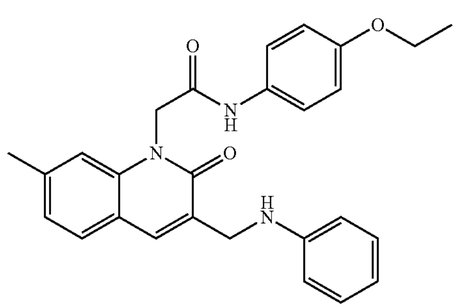 [SMILES: CCOc1ccc(NC(=O)Cn2c(=O)c(CNc3ccccc3)cc3ccc(C)cc32)cc1] | − |

TABLE 2-continued

Inhibition of FOXC2-expressing HMLER cells by Formula II Compounds

| Compound No. | Structure | Activity Score |
|---|---|---|
| 2CR | 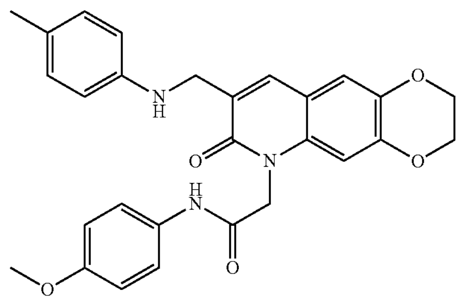 [SMILES: COc1ccc(NC(=O)Cn2c(=O)c(CNc3ccc(C)cc3)cc3cc4c(cc32)OCCO4)cc1] | − |
| 2CS | 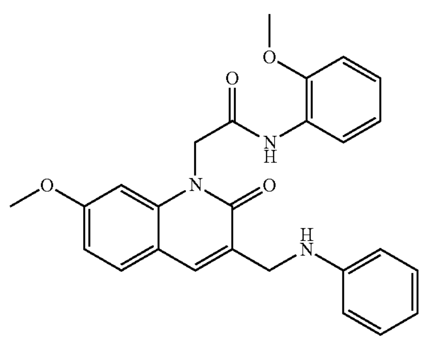 | − |
| 2CT | 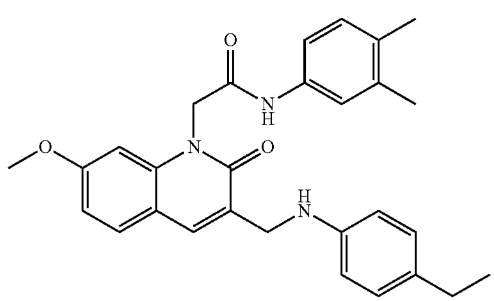 [SMILES: CCc1ccc(NCc2cc3ccc(OC)cc3n(CC(=O)Nc3ccc(C)c(C)c3)c2=O)cc1] | − |
| 2CU | 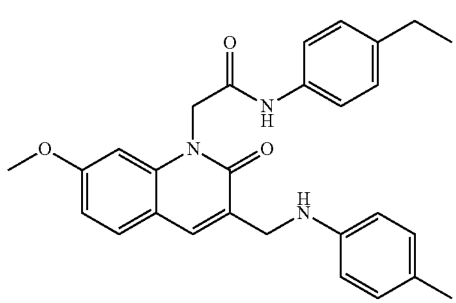 [SMILES: CCc1ccc(NC(=O)Cn2c(=O)c(CNc3ccc(C)cc3)cc3ccc(OC)cc32)cc1] | − |

TABLE 2-continued

Inhibition of FOXC2-expressing HMLER cells by Formula II Compounds

| Compound No. | Structure | Activity Score |
|---|---|---|
| 2CV | 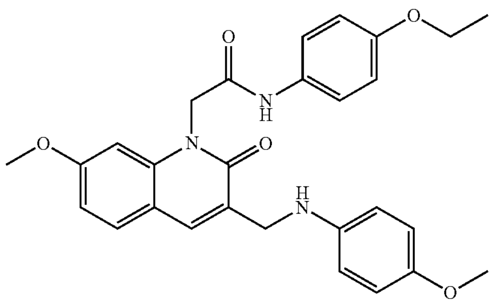 [SMILES: CCOc1ccc(NC(=O)Cn2c(=O)c(CNc3ccc(OC)cc3)cc3ccc(OC)cc32)cc1] | − |
| 2CW | 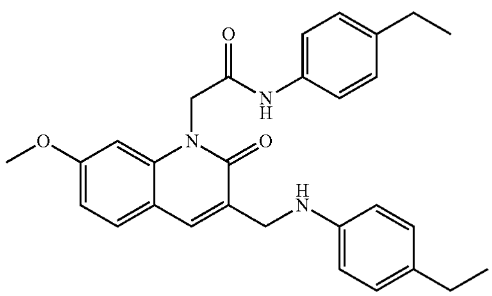 [SMILES: CCc1ccc(NCc2cc3ccc(OC)cc3n(CC(=O)Nc3ccc(CC)cc3)c2=O)cc1] | − |
| 2CX | 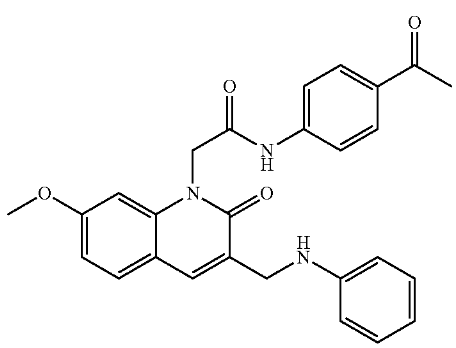 [SMILES: COc1ccc2cc(CNc3ccccc3)c(=O)n(CC(=O)Nc3ccc(C(C)=O)cc3)c2c1] | − |
| 2CY | 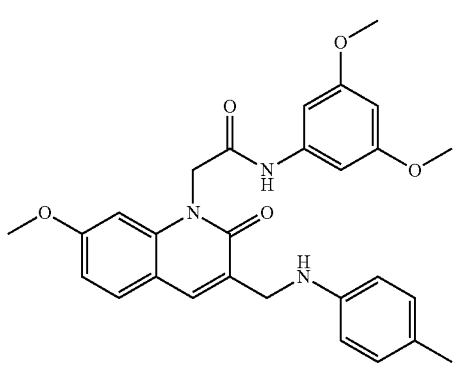 | − |

TABLE 2-continued
Inhibition of FOXC2-expressing HMLER cells by Formula II Compounds
| Compound No. | Structure | Activity Score |
|---|---|---|
| 2CZ | 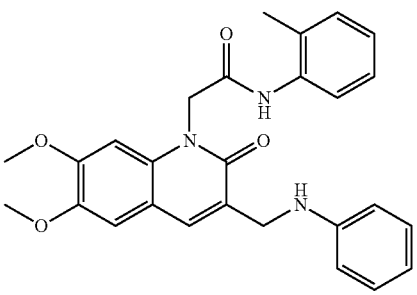 [SMILES: COc1cc2cc(CNc3ccccc3)c(=O)n(CC(=O)Nc3ccccc3C)c2cc1OC] | − |
| 2DA | 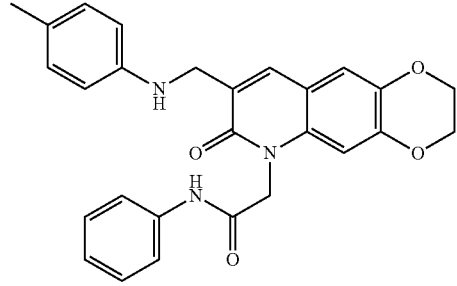 [SMILES: Cc1ccc(NCc2cc3cc4c(cc3n(CC(=O)Nc3ccccc3)c2=O)OCCO4)cc1] | − |
| 2DB | 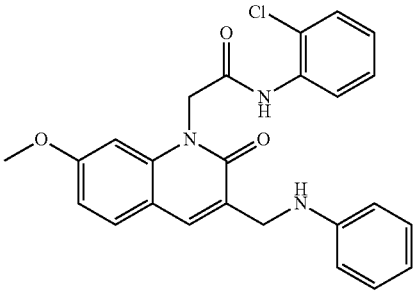 [SMILES: COc1ccc2cc(CNc3ccccc3)c(=O)n(CC(=O)Nc3ccccc3Cl)c2c1] | − |
| 2DC | 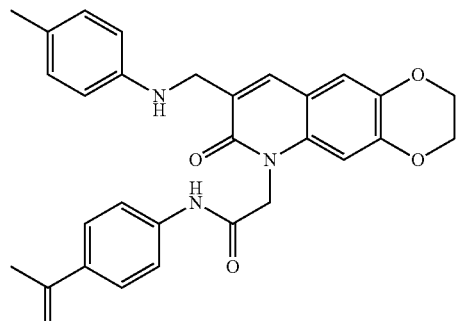 | − |
| 2DD | 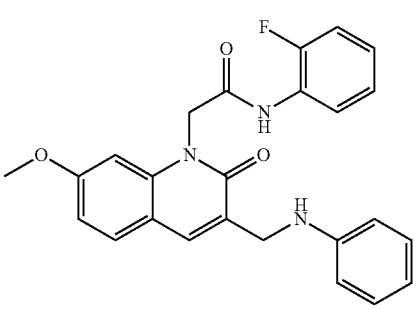 [SMILES: COc1ccc2cc(CNc3ccccc3)c(=O)n(CC(=O)Nc3ccccc3F)c2c1] | − |

TABLE 2-continued

Inhibition of FOXC2-expressing HMLER cells by Formula II Compounds

| Compound No. | Structure | Activity Score |
|---|---|---|
| 2DE | 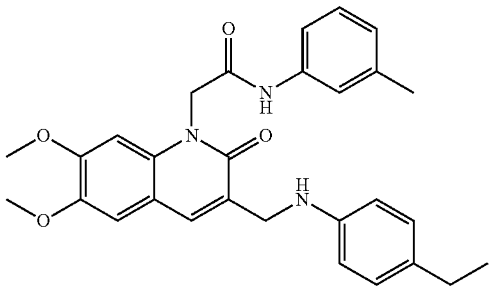 [SMILES: CCc1ccc(NCc2cc3cc(OC)c(OC)cc3n(CC(=O)Nc3cccc(C)c3)c2=O)cc1] | − |
| 2DF | 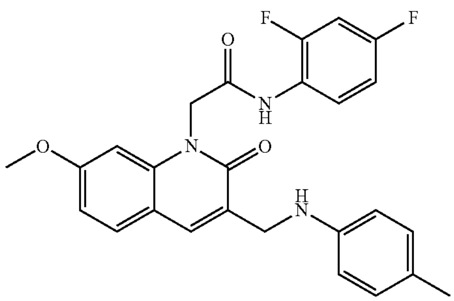 | − |
| 2DG | 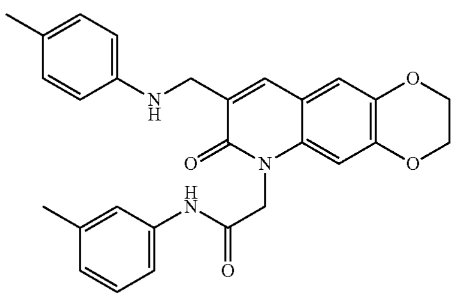 [SMILES: Cc1ccc(NCc2cc3cc4c(cc3n(CC(=O)Nc3cccc(C)c3)c2=O)OCCO4)cc1] | − |
| 2DH | 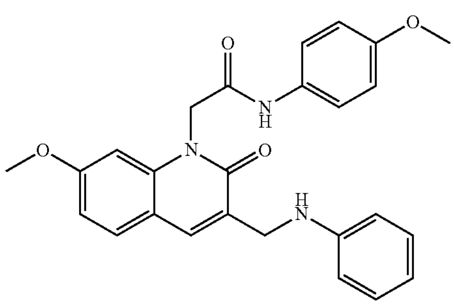 | − |
| 2DI | 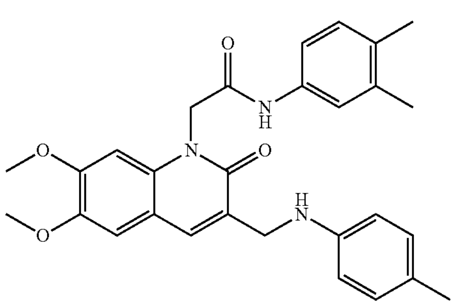 | − |

TABLE 2-continued
Inhibition of FOXC2-expressing HMLER cells by Formula II Compounds
| Compound No. | Structure | Activity Score |
|---|---|---|
| 2DJ | 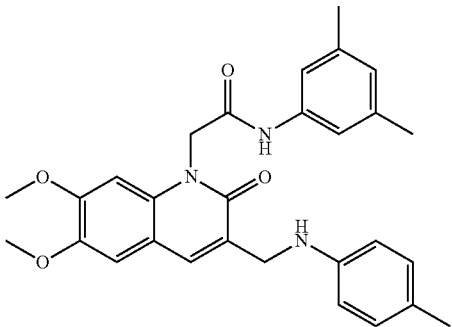 | − |
| 2DK | 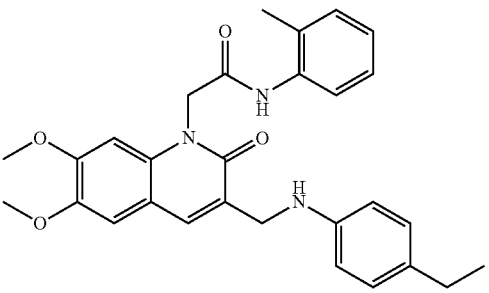 [SMILES: CCc1ccc(NCc2cc3cc(OC)c(OC)cc3n(CC(=O)Nc3ccccc3C)c2=O)cc1] | − |
| 2DL | 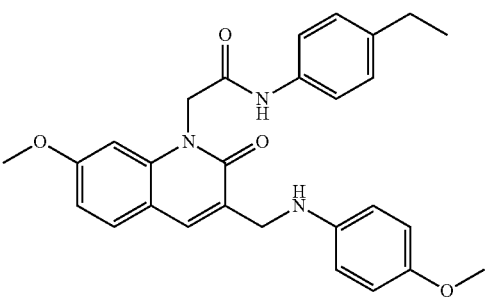 | − |
| 2DM | 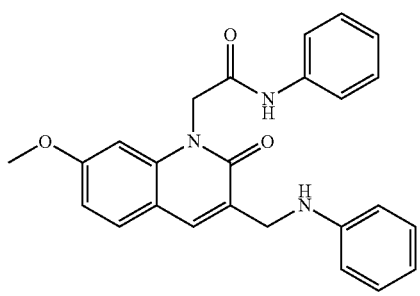 [SMILES: COc1ccc2cc(CNc3ccccc3)c(=O)n(CC(=O)Nc3ccccc3)c2c1] | − |
| 2DN | 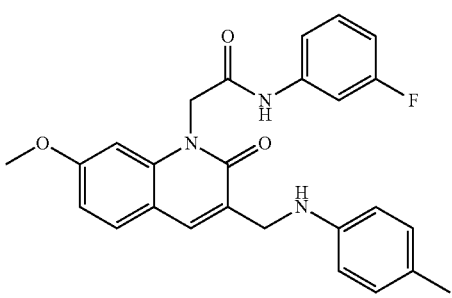 | − |

TABLE 2-continued

Inhibition of FOXC2-expressing HMLER cells by Formula II Compounds

| Compound No. | Structure | Activity Score |
|---|---|---|
| 2DO | 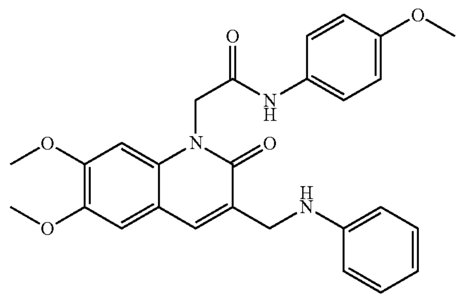 | − |
| 2DP | 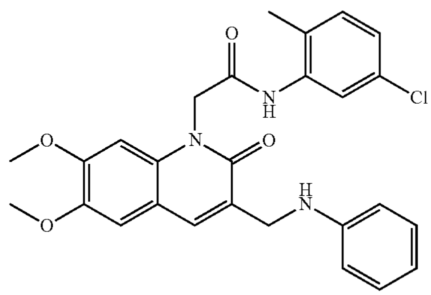 [SMILES: COc1cc2cc(CNc3ccccc3)c(=O)n(CC(=O)Nc3cc(Cl)ccc3C)c2cc1OC] | − |
| 2DQ | 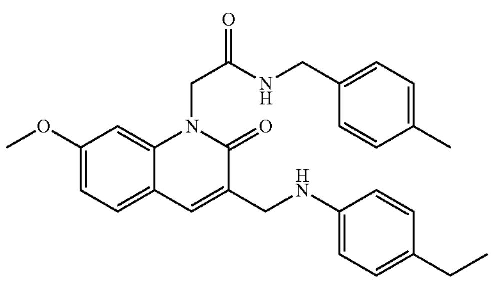 [SMILES: CCc1ccc(NCc2cc3ccc(OC)cc3n(CC(=O)NCc3ccc(C)cc3)c2=O)cc1] | − |
| 2DR | 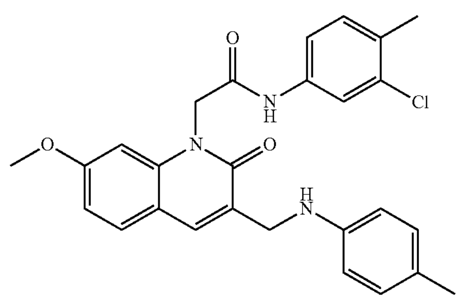 | − |
| 2DS | 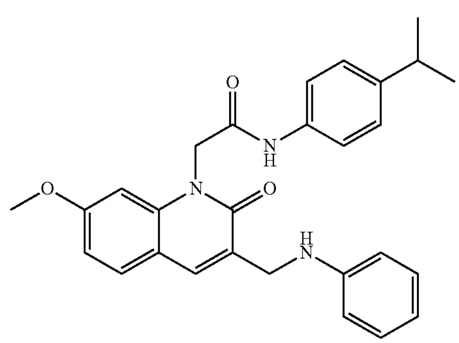 [SMILES: COc1ccc2cc(CNc3ccccc3)c(=O)n(CC(=O)Nc3ccc(C(C)C)cc3)c2c1] | − |

TABLE 2-continued

Inhibition of FOXC2-expressing HMLER cells by Formula II Compounds

| Compound No. | Structure | Activity Score |
|---|---|---|
| 2DT | 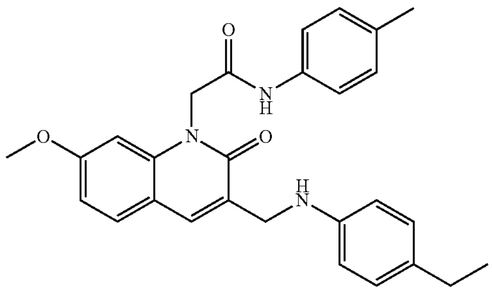 [SMILES: CCc1ccc(NCc2cc3ccc(OC)cc3n(CC(=O)Nc3ccc(C)cc3)c2=O)cc1] | – |
| 2DU | 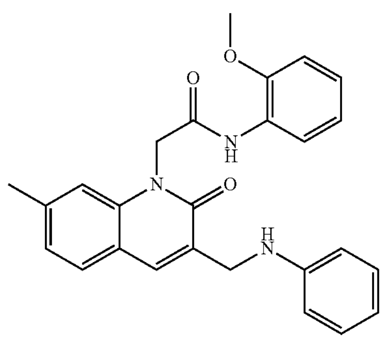 [SMILES: COc1ccccc1NC(=O)Cn1c(=O)c(CNc2ccccc2)cc2ccc(C)cc21] | – |
| 2DV | 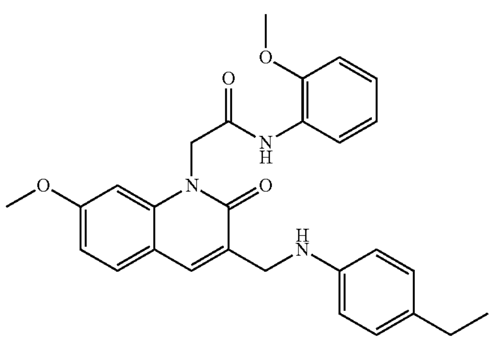 [SMILES: CCc1ccc(NCc2cc3ccc(OC)cc3n(CC(=O)Nc3ccccc3OC)c2=O)cc1] | – |
| 2DW | 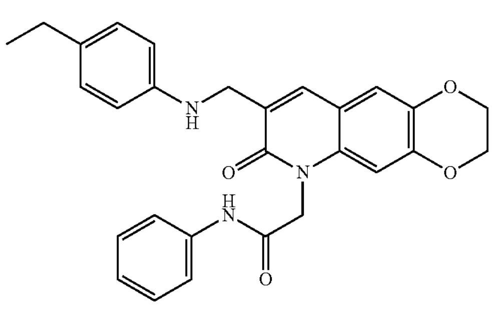 [SMILES: CCc1ccc(NCc2cc3cc4c(cc3n(CC(=O)Nc3ccccc3)c2=O)OCCO4)cc1] | – |

TABLE 2-continued

Inhibition of FOXC2-expressing HMLER cells by Formula II Compounds

| Compound No. | Structure | Activity Score |
|---|---|---|
| 2DX | 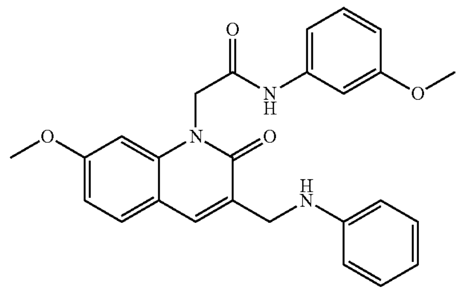 | − |
| 2DY | 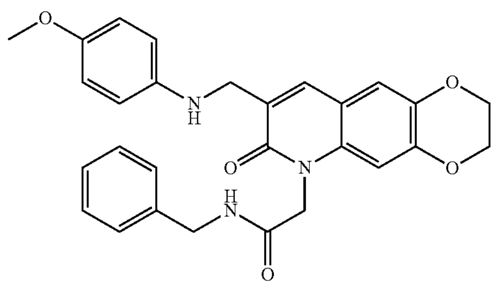 [SMILES: COc1ccc(NCc2cc3cc4c(cc3n(CC(=O)NCc3ccccc3)c2=O)OCCO4)cc1] | − |
| 2DZ | 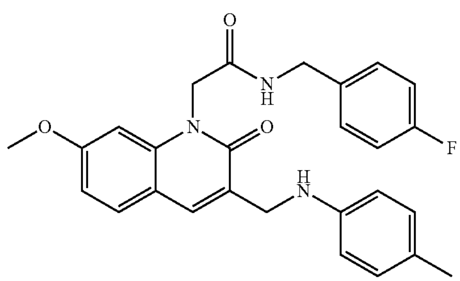 [SMILES: COc1ccc2cc(CNc3ccc(C)cc3)c(=O)n(CC(=O)NCc3ccc(F)cc3)c2c1] | − |
| 2EA | 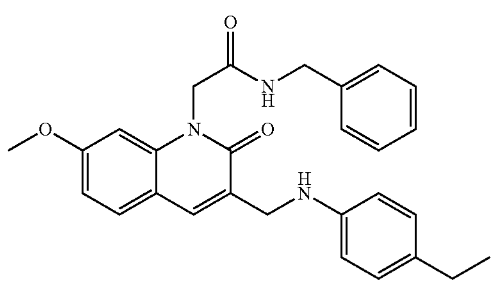 [SMILES: CCc1ccc(NCc2cc3ccc(OC)cc3n(CC(=O)NCc3ccccc3)c2=O)cc1] | − |
| 2EB | 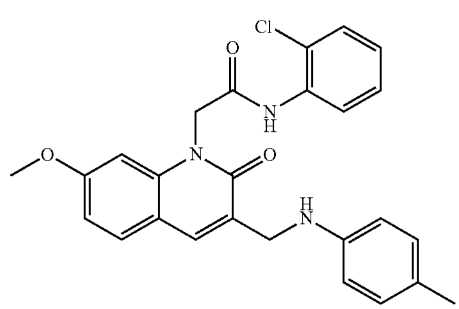 | − |

TABLE 2-continued

Inhibition of FOXC2-expressing HMLER cells by Formula II Compounds

| Compound No. | Structure | Activity Score |
|---|---|---|
| 2EC | 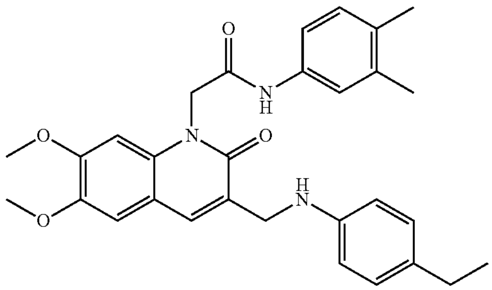 [SMILES: CCc1ccc(NCc2cc3cc(OC)c(OC)cc3n(CC(=O)Nc3ccc(C)c(C)c3)c2=O)cc1] | − |
| 2ED | 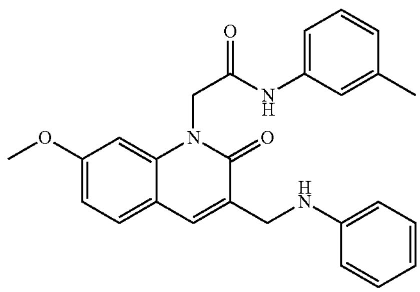 | − |
| 2EE | 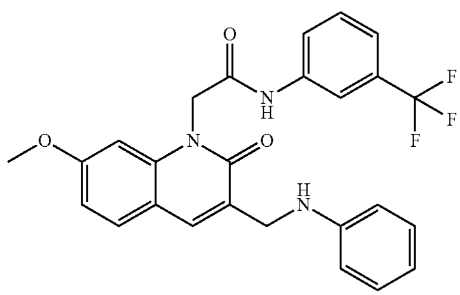 [SMILES: COc1ccc2cc(CNc3ccccc3)c(=O)n(CC(=O)Nc3cccc(C(F)(F)F)c3)c2c1] | − |
| 2EF | 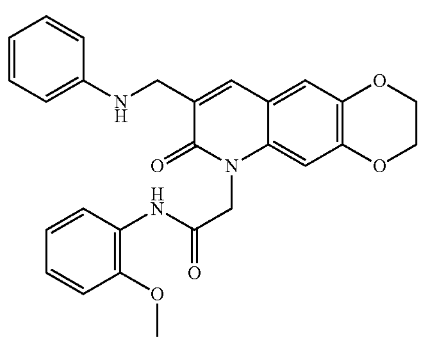 [SMILES: COc1ccccc1NC(=O)Cn1c(=O)c(CNc2ccccc2)cc2cc3c(cc21)OCCO3] | − |
| 2EG | 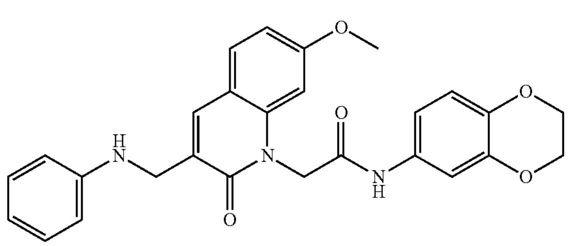 [SMILES: COc1ccc2cc(CNc3ccccc3)c(=O)n(CC(=O)Nc3ccc4c(c3)OCCO4)c2c1] | − |

TABLE 2-continued

Inhibition of FOXC2-expressing HMLER cells by Formula II Compounds

| Compound No. | Structure | Activity Score |
|---|---|---|
| 2EH | 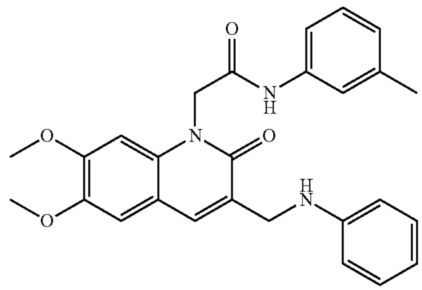 | − |
| 2EI | 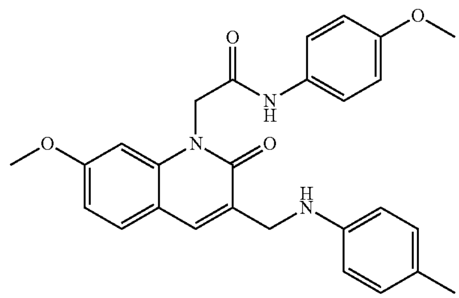 | − |
| 2EJ | 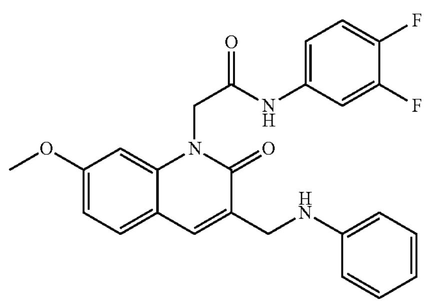 [SMILES: COc1ccc2cc(CNc3ccccc3)c(=O)n(CC(=O)Nc3ccc(F)c(F)c3)c2c1] | − |
| 2EK | 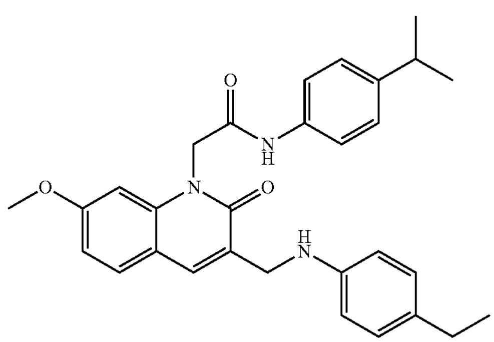 [SMILES: CCc1ccc(NCc2cc3ccc(OC)cc3n(CC(=O)Nc3ccc(C(C)C)cc3)c2=O)cc1] | − |
| 2EL | 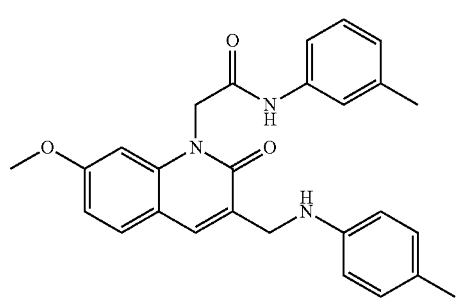 | − |

TABLE 2-continued

Inhibition of FOXC2-expressing HMLER cells by Formula II Compounds

| Compound No. | Structure | Activity Score |
|---|---|---|
| 2EM | 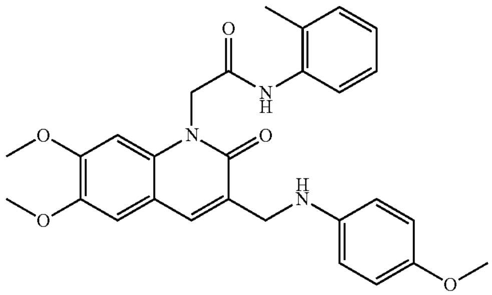 | − |
| 2EN | 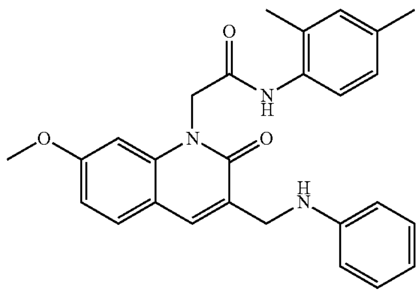 | − |
| 2EO | 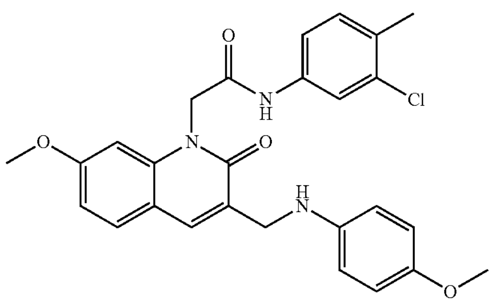 | − |
| 2EP | 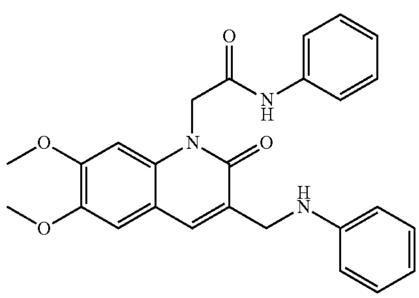 [SMILES: COc1cc2cc(CNc3ccccc3)c(=O)n(CC(=O)Nc3ccccc3)c2cc1OC] | − |
| 2EQ | 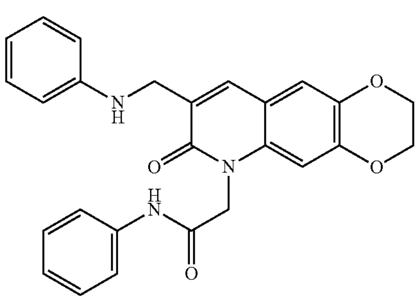 [SMILES: O=C(Cn1c(=O)c(CNc2ccccc2)cc2cc3c(cc21)OCCO3)Nc1ccccc1] | − |

TABLE 2-continued

Inhibition of FOXC2-expressing HMLER cells by Formula II Compounds

| Compound No. | Structure | Activity Score |
|---|---|---|
| 2ER | 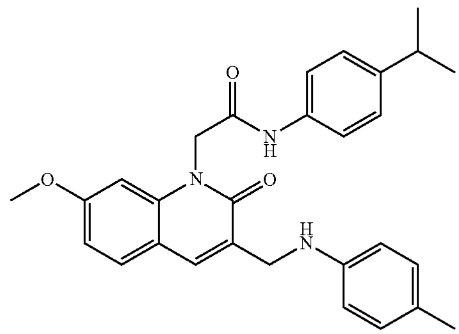 [SMILES: COc1ccc2cc(CNc3ccc(C)cc3)c(=O)n(CC(=O)Nc3ccc(C(C)C)cc3)c2c1] | − |
| 2ES | 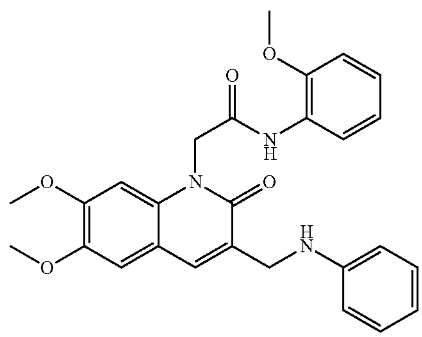 [SMILES: COc1ccccc1NC(=O)Cn1c(=O)c(CNc2ccccc2)cc2cc(OC)c(OC)cc21] | − |
| 2ET | 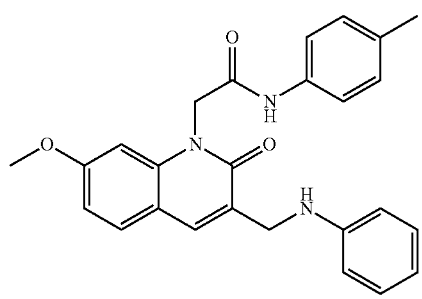 | − |
| 2EU | 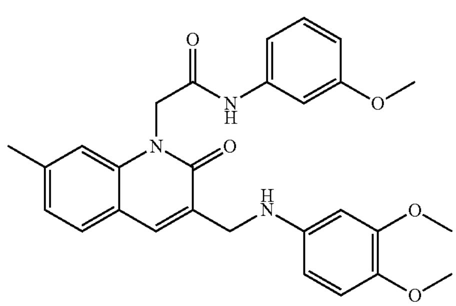 | − |

TABLE 2-continued

Inhibition of FOXC2-expressing HMLER cells by Formula II Compounds

| Compound No. | Structure | Activity Score |
|---|---|---|
| 2EV | 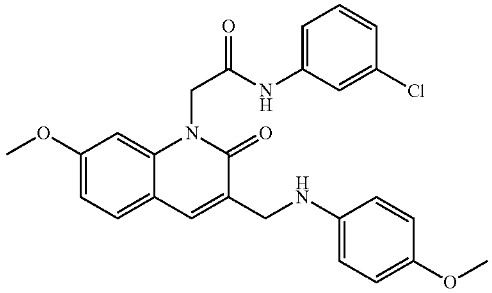 | − |
| 2EW | 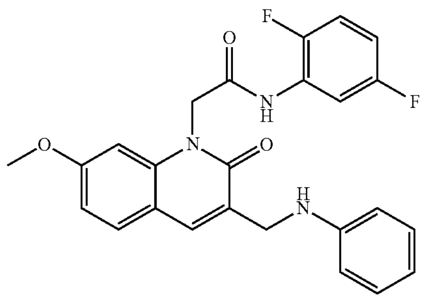 [SMILES: COc1ccc2cc(CNc3ccccc3)c(=O)n(CC(=O)Nc3cc(F)ccc3F)c2c1] | − |
| 2EX | 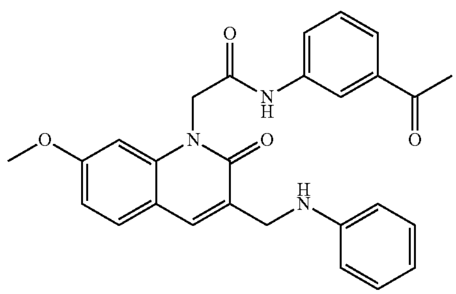 [SMILES: COc1ccc2cc(CNc3ccccc3)c(=O)n(CC(=O)Nc3cccc(C(C)=O)c3)c2c1] | − |
| 2EY | 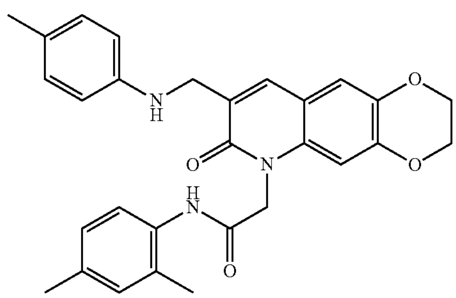 [SMILES: Cc1ccc(NCc2cc3cc4c(cc3n(CC(=O)Nc3ccc(C)cc3C)c2=O)OCCO4)cc1] | − |
| 2EZ | 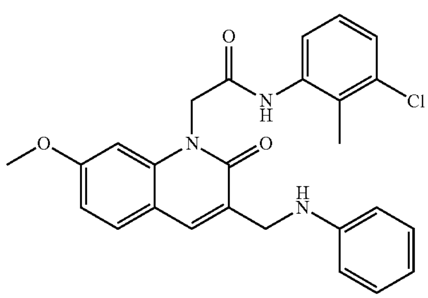 [SMILES: COc1ccc2cc(CNc3ccccc3)c(=O)n(CC(=O)Nc3cccc(Cl)c3C)c2c1] | − |

TABLE 2-continued

Inhibition of FOXC2-expressing HMLER cells by Formula II Compounds

| Compound No. | Structure | Activity Score |
|---|---|---|
| 2FA | 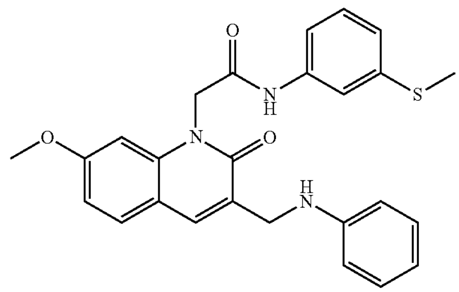 | − |
| 2FB | 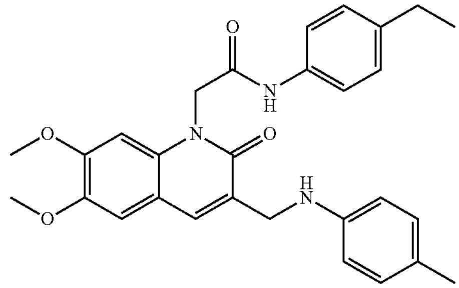 [SMILES: CCc1ccc(NC(=O)Cn2c(=O)c(CNc3ccc(C)cc3)cc3cc(OC)c(OC)cc32)cc1] | − |
| 2FC | 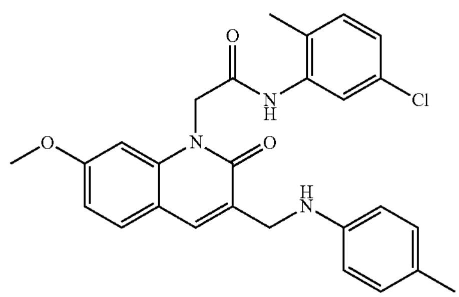 | − |
| 2FD | 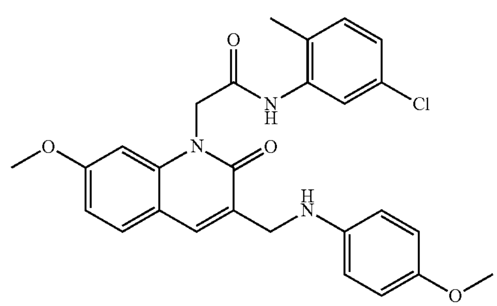 | − |
| 2FE | 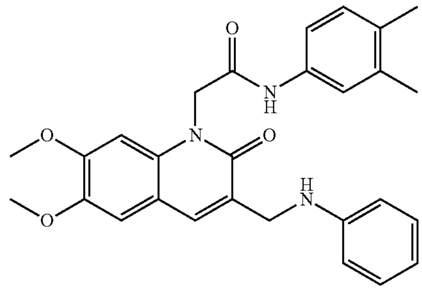 | − |

TABLE 2-continued

Inhibition of FOXC2-expressing HMLER cells by Formula II Compounds

| Compound No. | Structure | Activity Score |
|---|---|---|
| 2FF | 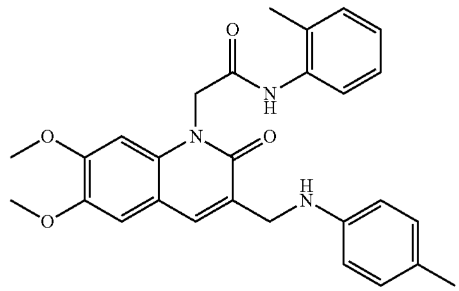 | − |
| 2FG | 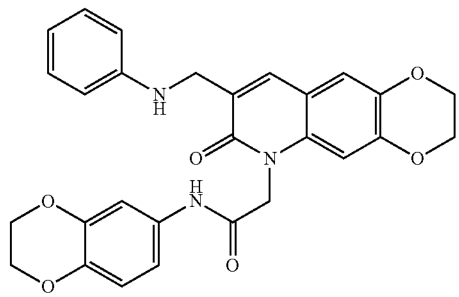 [SMILES: O=C(Cn1c(=O)c(CNc2ccccc2)cc2cc3c(cc21)OCCO3)Nc1ccc2c(c1)OCCO2] | − |
| 2FH | 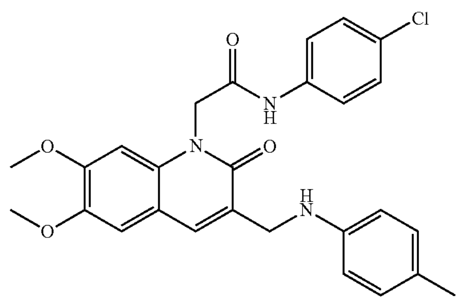 | − |
| 2FI | 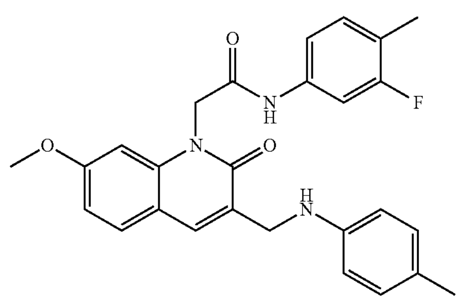 | − |
| 2FJ | 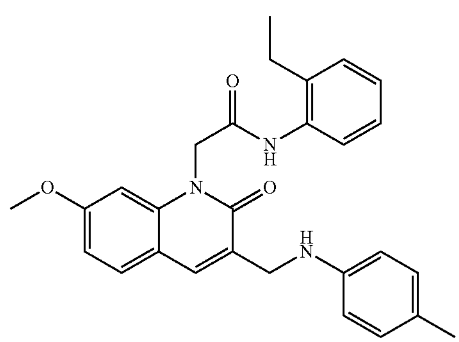 | − |

TABLE 2-continued

Inhibition of FOXC2-expressing HMLER cells by Formula II Compounds

| Compound No. | Structure | Activity Score |
|---|---|---|
| 2FK | 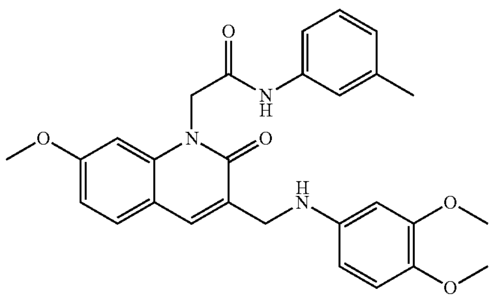 | − |
| 2FL | 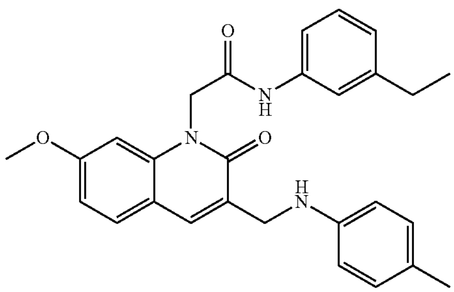 [SMILES: CCc1cccc(NC(=O)Cn2c(=O)c(CNc3ccc(C)cc3)cc3ccc(OC)cc32)c1] | − |
| 2FM | 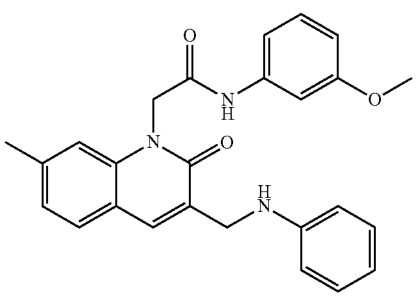 | − |
| 2FN | 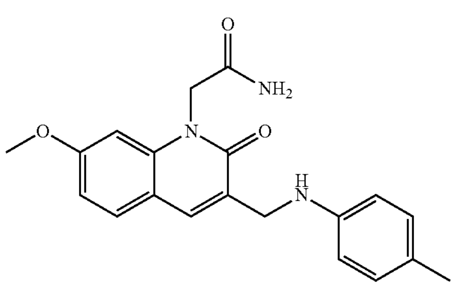 | − |
| 2FO | 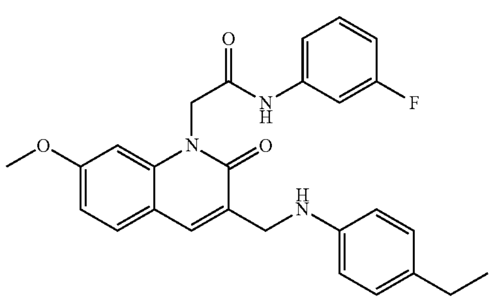 | − |

TABLE 2-continued

Inhibition of FOXC2-expressing HMLER cells by Formula II Compounds

| Compound No. | Structure | Activity Score |
|---|---|---|
| 2FP | 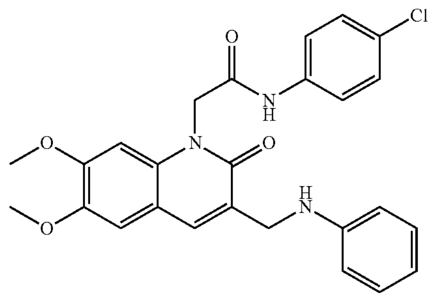 [SMILES: COc1cc2cc(CNc3ccccc3)c(=O)n(CC(=O)Nc3ccc(Cl)cc3)c2cc1OC] | − |
| 2FQ | 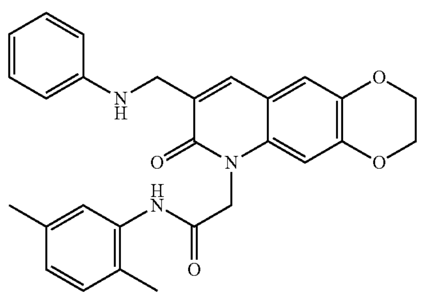 [SMILES: Cc1ccc(C)c(NC(=O)Cn2c(=O)c(CNc3ccccc3)cc3cc4c(cc32)OCCO4)c1] | − |
| 2FR | 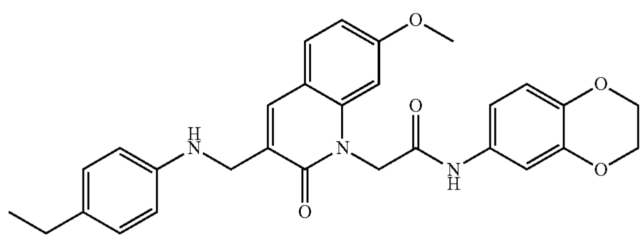 [SMILES: CCc1ccc(NCc2cc3ccc(OC)cc3n(CC(=O)Nc3ccc4c(c3)OCCO4)c2=O)cc1] | − |
| 2FS | 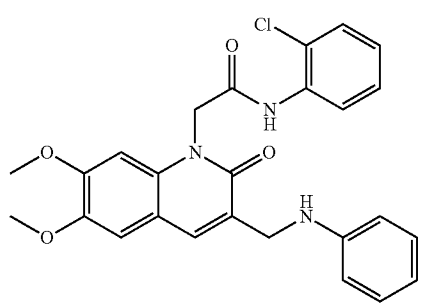 [SMILES: COc1cc2cc(CNc3ccccc3)c(=O)n(CC(=O)Nc3ccccc3Cl)c2cc1OC] | − |
| 2FT | 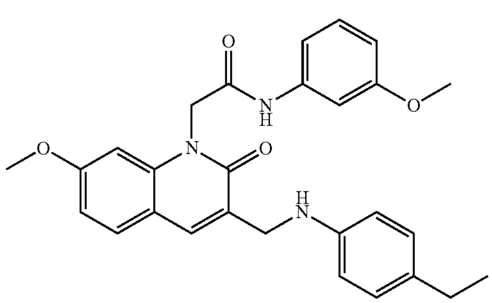 [SMILES: CCc1ccc(NCc2cc3ccc(OC)cc3n(CC(=O)Nc3cccc(OC)c3)c2=O)cc1] | − |

TABLE 2-continued

Inhibition of FOXC2-expressing HMLER cells by Formula II Compounds

| Compound No. | Structure | Activity Score |
|---|---|---|
| 2FU | 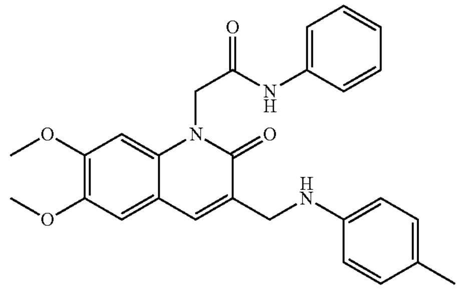 | − |
| 2FV | 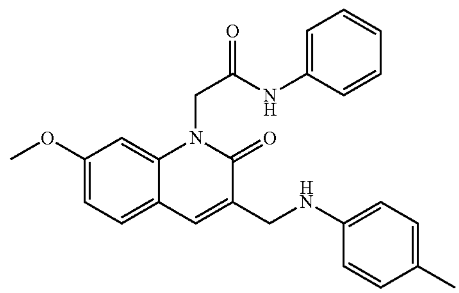 | − |
| 2FW | 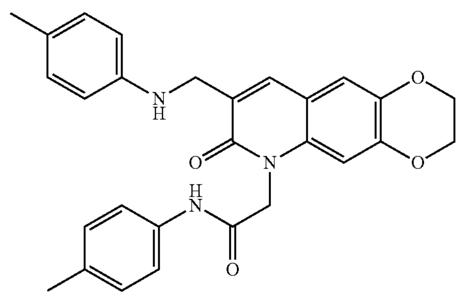 [SMILES: Cc1ccc(NCc2cc3cc4c(cc3n(CC(=O)Nc3ccc(C)cc3)c2=O)OCCO4)cc1] | − |
| 2FX | 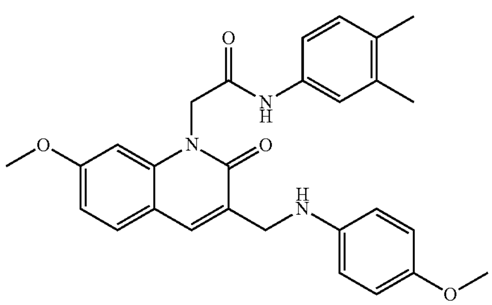 | − |
| 2FY | 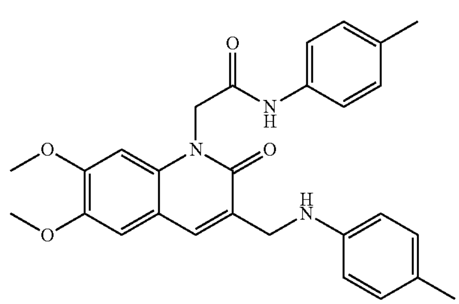 | − |

TABLE 2-continued
Inhibition of FOXC2-expressing HMLER cells by Formula II Compounds
| Compound No. | Structure | Activity Score |
|---|---|---|
| 2FZ | 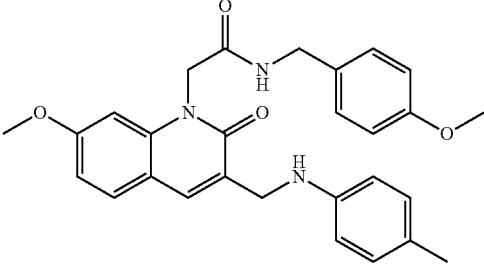 | – |
| 2GA | 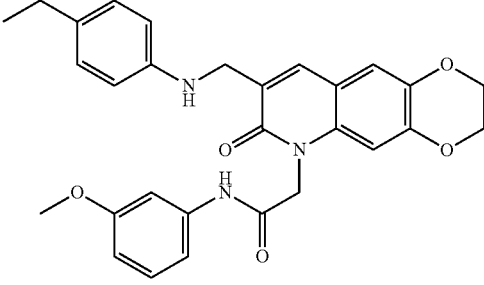 [SMILES: CCc1ccc(NCc2cc3cc4c(cc3n(CC(=O)Nc3cccc(OC)c3)c2=O)OCCO4)cc1] | – |
| 2GB | 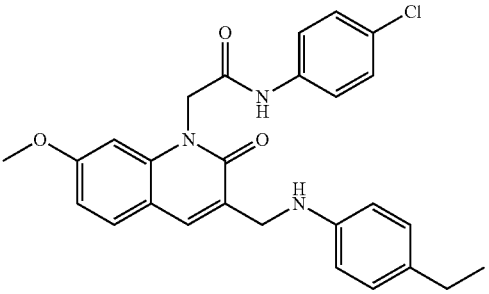 [SMILES: CCc1ccc(NCc2cc3ccc(OC)cc3n(CC(=O)Nc3ccc(Cl)cc3)c2=O)cc1] | – |
| 2GC | 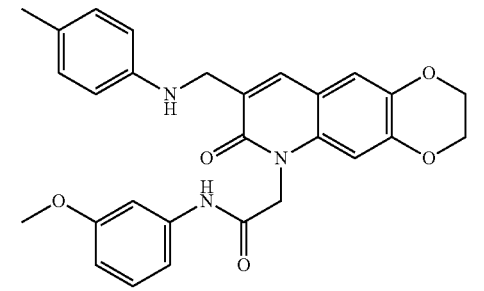 | – |
| 2GD | 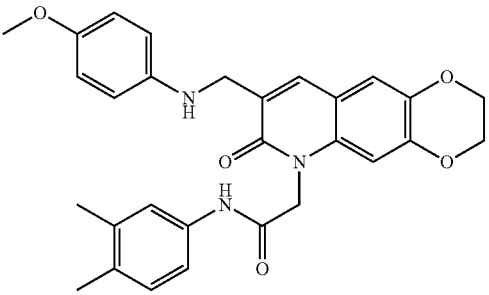 [SMILES: COc1ccc(NCc2cc3cc4c(cc3n(CC(=O)Nc3ccc(C)c(C)c3)c2=O)OCCO4)cc1] | – |

TABLE 2-continued
Inhibition of FOXC2-expressing HMLER cells by Formula II Compounds
| Compound No. | Structure | Activity Score |
|---|---|---|
| 2GE | 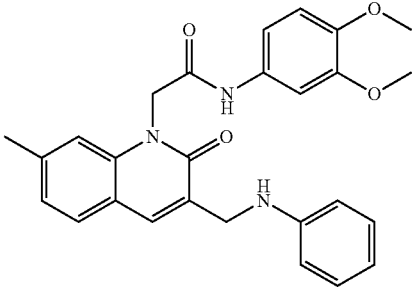 | − |
| 2GF | 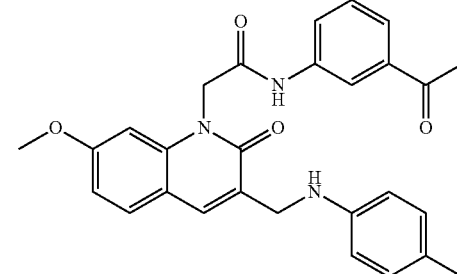 | − |
| 2GG | 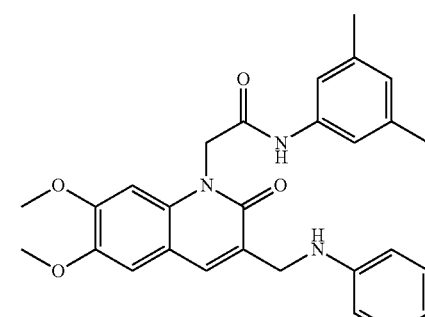 | − |
| 2GH | 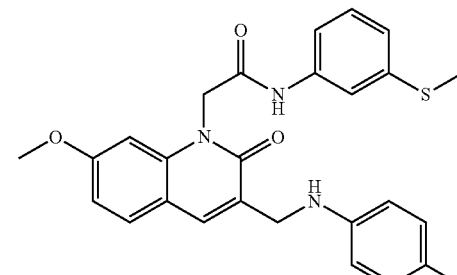 | − |
| 2GI | 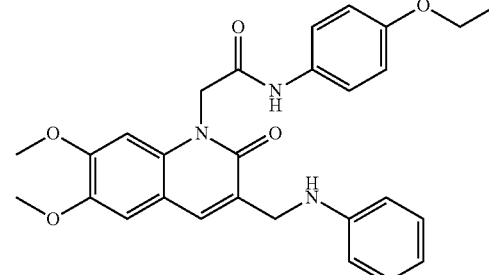 | − |

TABLE 2-continued

Inhibition of FOXC2-expressing HMLER cells by Formula II Compounds

| Compound No. | Structure | Activity Score |
|---|---|---|
| 2GJ | 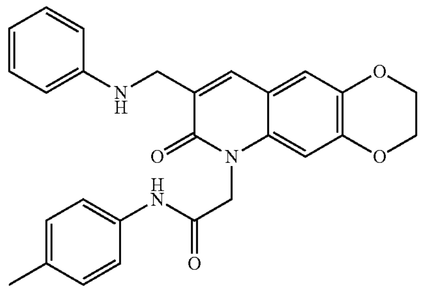 [SMILES: Cc1ccc(NC(=O)Cn2c(=O)c(CNc3ccccc3)cc3cc4c(cc32)OCCO4)cc1] | – |
| 2GK | 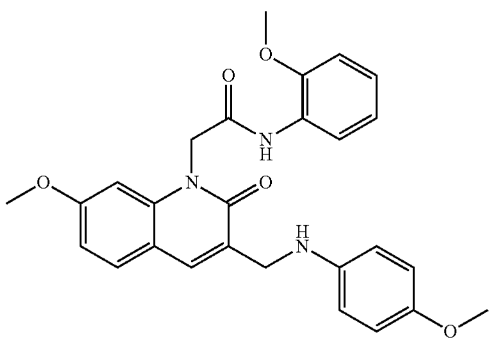 | – |
| 2GL | 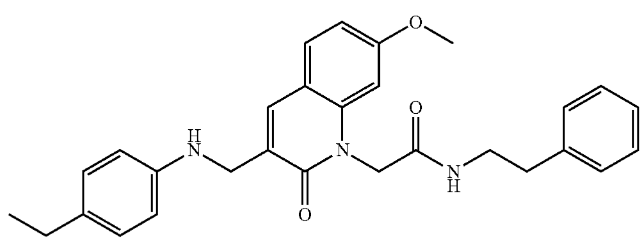 [SMILES: CCc1ccc(NCc2cc3ccc(OC)cc3n(CC(=O)NCCc3ccccc3)c2=O)cc1] | – |
| 2GM | 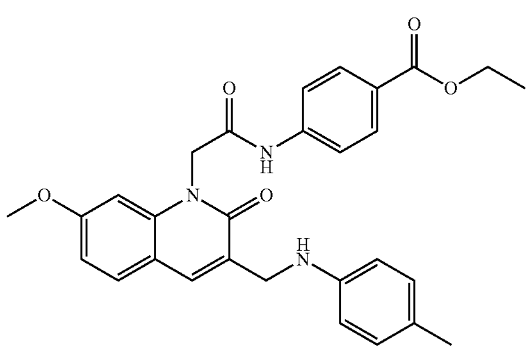 [SMILES: CCOC(=O)c1ccc(NC(=O)Cn2c(=O)c(CNc3ccc(C)cc3)cc3ccc(OC)cc32)cc1] | – |
| 2GN | 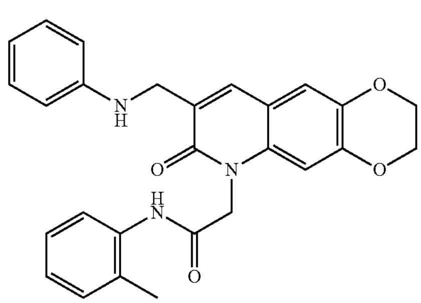 [SMILES: Cc1ccccc1NC(=O)Cn1c(=O)c(CNc2ccccc2)cc2cc3c(cc21)OCCO3] | – |

TABLE 2-continued

Inhibition of FOXC2-expressing HMLER cells by Formula II Compounds

| Compound No. | Structure | Activity Score |
|---|---|---|
| 2GO | 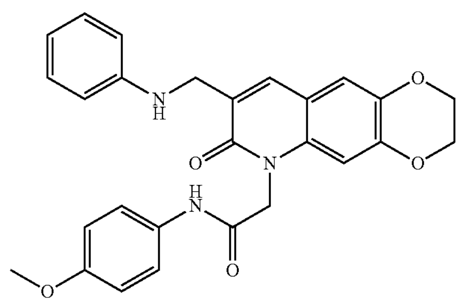 [SMILES: COc1ccc(NC(=O)Cn2c(=O)c(CNc3ccccc3)cc3cc4c(cc32)OCCO4)cc1] | − |
| 2GP | 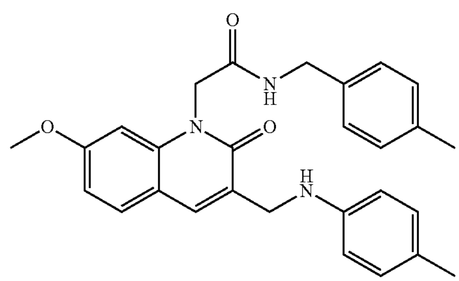 | − |
| 2GQ | 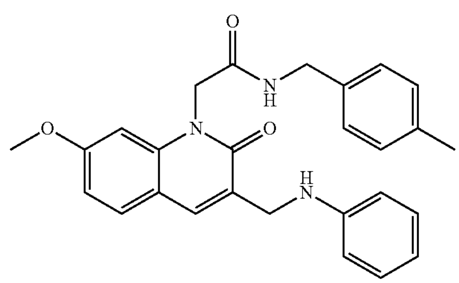 | − |
| 2GR | 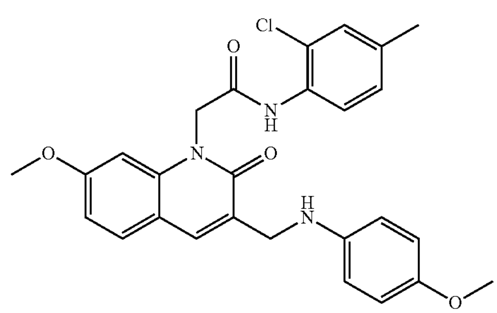 | − |
| 2GS | 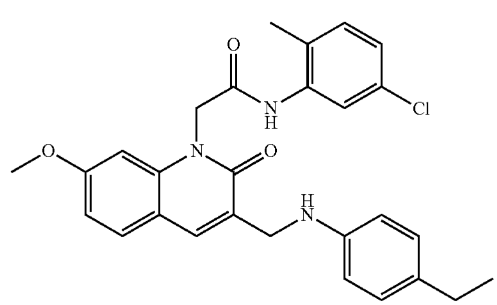 [SMILES: CCc1ccc(NCc2cc3ccc(OC)cc3n(CC(=O)Nc3cc(Cl)ccc3C)c2=O)cc1] | − |

TABLE 2-continued

Inhibition of FOXC2-expressing HMLER cells by Formula II Compounds

| Compound No. | Structure | Activity Score |
|---|---|---|
| 2GT | 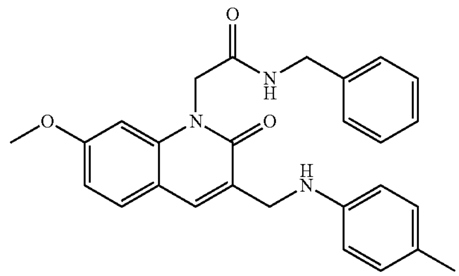 | − |
| 2GU | 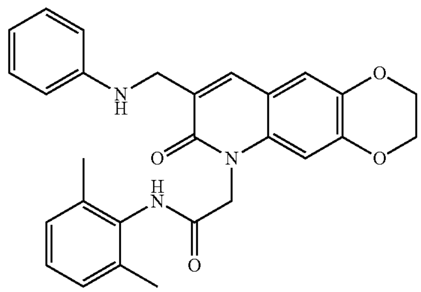 [SMILES: Cc1cccc(C)c1NC(=O)Cn1c(=O)c(CNc2ccccc2)cc2cc3c(cc21)OCCO3] | − |
| 2GV | 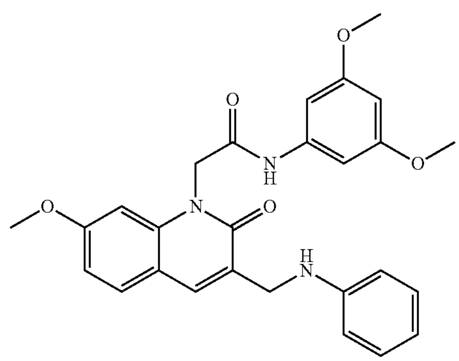 | − |
| 2GW | 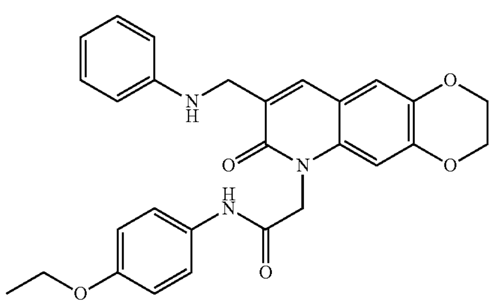 [SMILES: CCOc1ccc(NC(=O)Cn2c(=O)c(CNc3ccccc3)cc3cc4c(cc32)OCCO4)cc1] | − |
| 2GX | 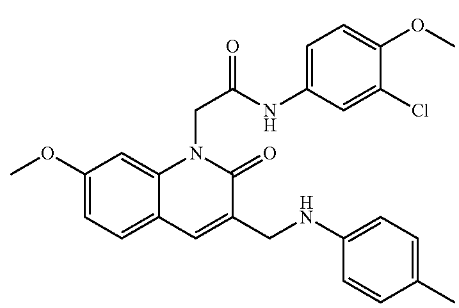 | − |

TABLE 2-continued

Inhibition of FOXC2-expressing HMLER cells by Formula II Compounds

| Compound No. | Structure | Activity Score |
|---|---|---|
| 2GY | 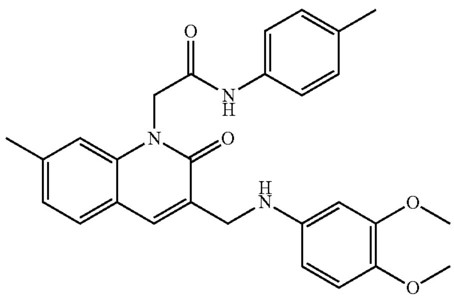 | − |
| 2GZ | 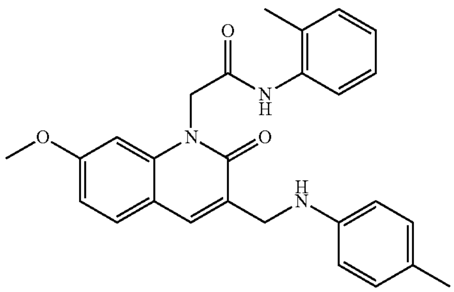 | − |
| 2HA | 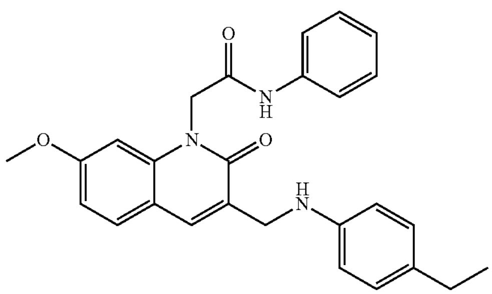 [SMILES: CCc1ccc(NCc2cc3ccc(OC)cc3n(CC(=O)Nc3ccccc3)c2=O)cc1] | − |
| 2HB | 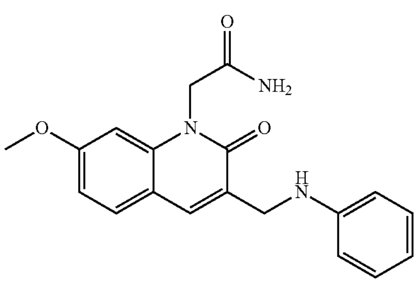 [SMILES: COc1ccc2cc(CNc3ccccc3)c(=O)n(CC(N)=O)c2c1] | − |
| 2HC | 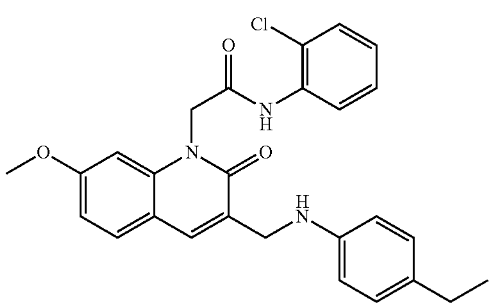 | − |

TABLE 2-continued
Inhibition of FOXC2-expressing HMLER cells by Formula II Compounds
| Compound No. | Structure | Activity Score |
|---|---|---|
| 2HD | 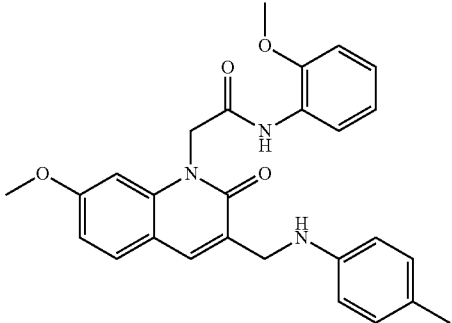 | – |
| 2HE | 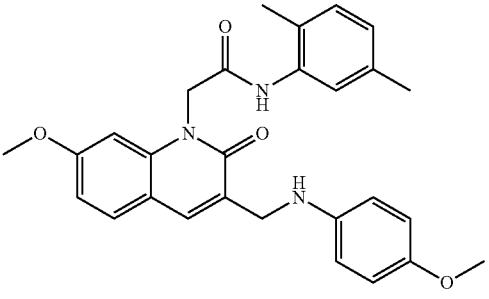 | – |
| 2HF | 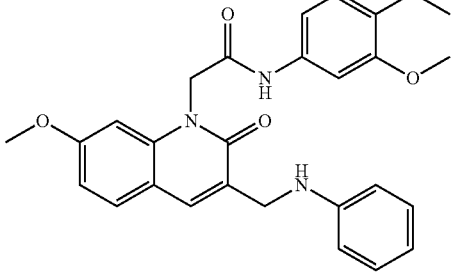 | – |
| 2HG | 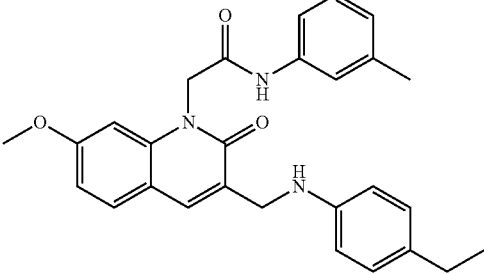 | – |
| 2HH | 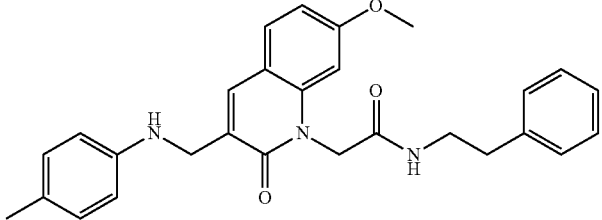 [SMILES: COc1ccc2cc(CNc3ccc(C)cc3)c(=O)n(CC(=O)NCCc3ccccc3)c2c1] | – |

TABLE 2-continued

Inhibition of FOXC2-expressing HMLER cells by Formula II Compounds

| Compound No. | Structure | Activity Score |
|---|---|---|
| 2HI | 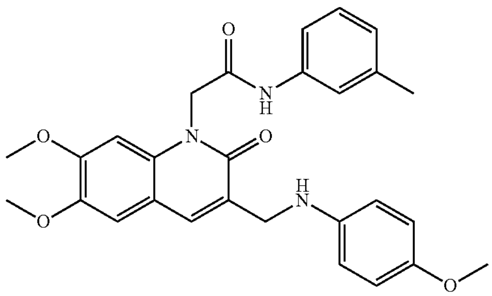 | − |
| 2HJ | 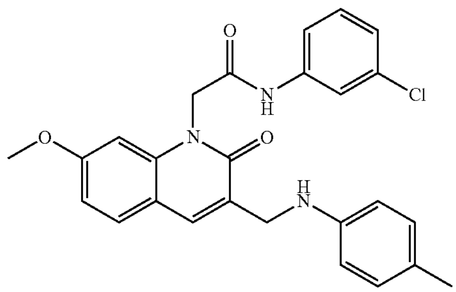 | − |
| 2HK | 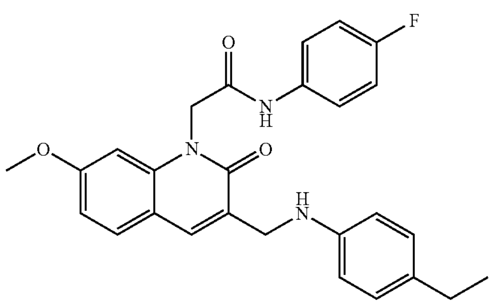 | − |
| 2HL | 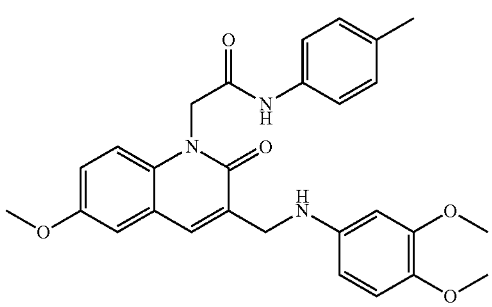 | − |
| 2HM | 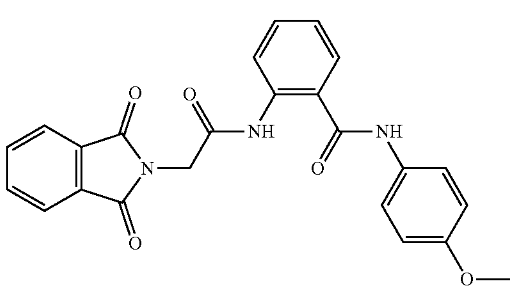 [SMILES: COc1ccc(NC(=O)c2ccccc2NC(=O)CN2C(=O)c3ccccc3C2=O)cc1] | − |

TABLE 2-continued

Inhibition of FOXC2-expressing HMLER cells by Formula II Compounds

| Compound No. | Structure | Activity Score |
|---|---|---|
| 2HN | 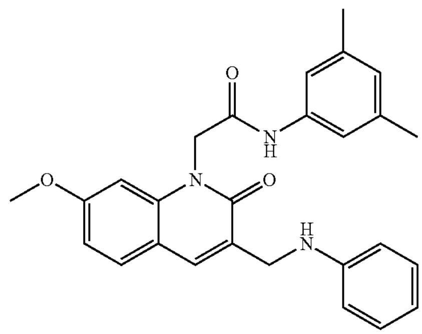 | – |
| 2HO | 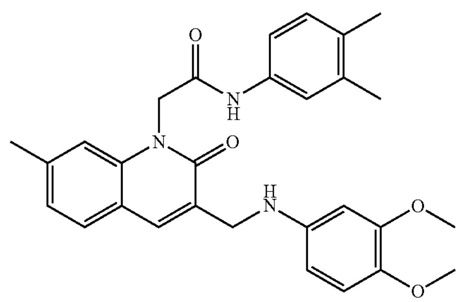 | – |
| 2HP | 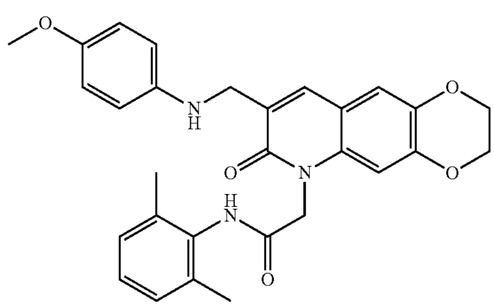 [SMILES: COc1ccc(NCc2cc3cc4c(cc3n(CC(=O)Nc3c(C)cccc3C)c2=O)OCCO4)cc1] | – |
| 2HQ | 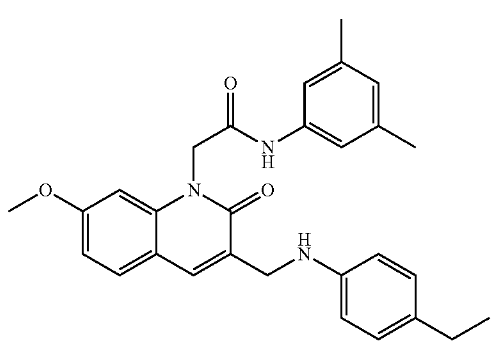 [SMILES: CCc1ccc(NCc2cc3ccc(OC)cc3n(CC(=O)Nc3cc(C)cc(C)c3)c2=O)cc1] | – |

TABLE 2-continued

Inhibition of FOXC2-expressing HMLER cells by Formula II Compounds

| Compound No. | Structure | Activity Score |
|---|---|---|
| 2HR | 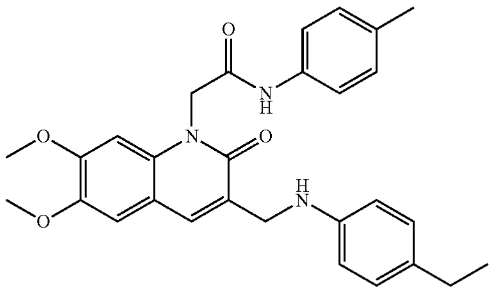 [SMILES: CCc1ccc(NCc2cc3cc(OC)c(OC)cc3n(CC(=O)Nc3ccc(C)cc3)c2=O)cc1] | − |
| 2HS | 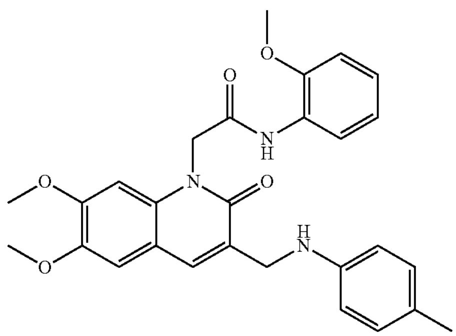 | − |
| 2HT | 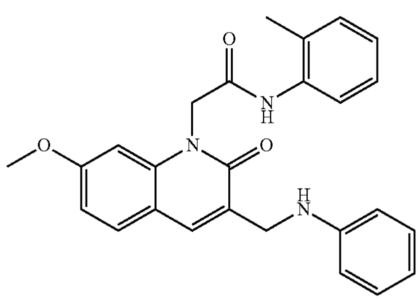 [SMILES: COc1ccc2cc(CNc3ccccc3)c(=O)n(CC(=O)Nc3ccccc3C)c2c1] | − |
| 2HU | 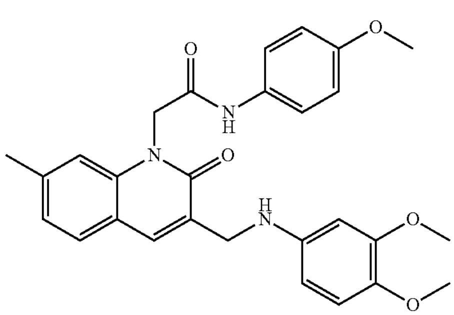 | − |

TABLE 2-continued

Inhibition of FOXC2-expressing HMLER cells by Formula II Compounds

| Compound No. | Structure | Activity Score |
|---|---|---|
| 2HV | 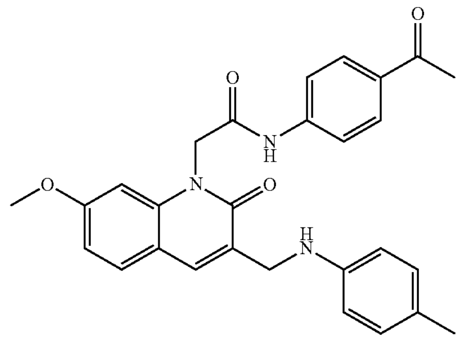 [SMILES: COc1ccc2cc(CNc3ccc(C)cc3)c(=O)n(CC(=O)Nc3ccc(C(C)=O)cc3)c2c1] | − |
| 2HW | 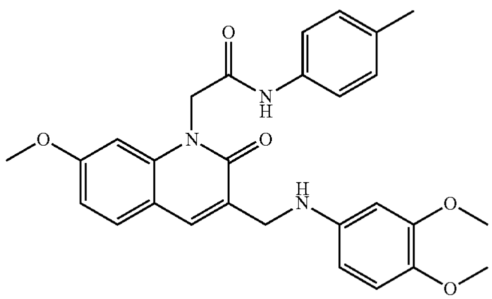 | − |
| 2HX | 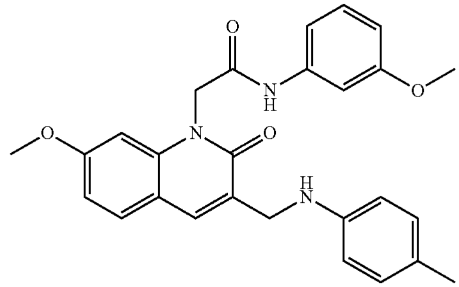 | − |
| 2HY | 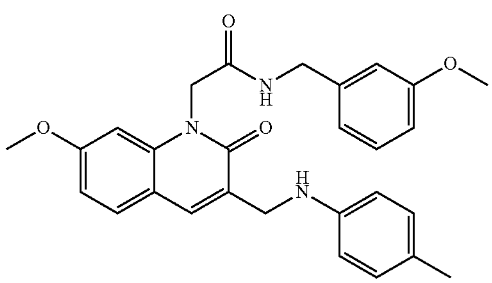 | − |
| 2HZ | 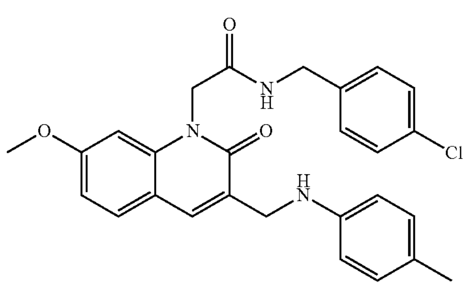 [SMILES: COc1ccc2cc(CNc3ccc(C)cc3)c(=O)n(CC(=O)NCc3ccc(Cl)cc3)c2c1] | − |

TABLE 2-continued

Inhibition of FOXC2-expressing HMLER cells by Formula II Compounds

| Compound No. | Structure | Activity Score |
|---|---|---|
| 2IA | 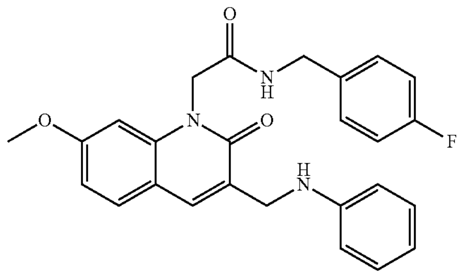 [SMILES: COc1ccc2cc(CNc3ccccc3)c(=O)n(CC(=O)NCc3ccc(F)cc3)c2c1] | − |
| 2IB | 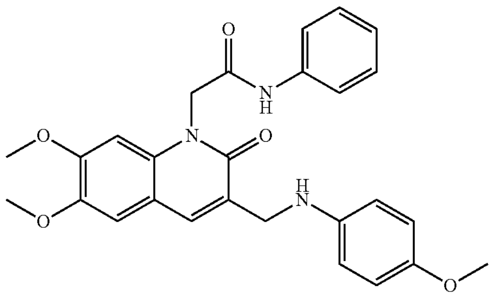 | − |
| 2IC | 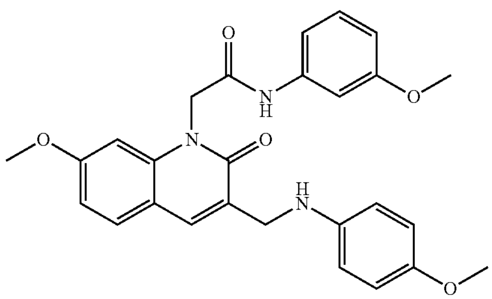 | − |
| 2ID | 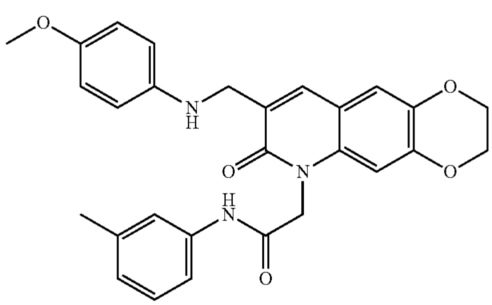 [SMILES: COc1ccc(NCc2cc3cc4c(cc3n(CC(=O)Nc3cccc(C)c3)c2=O)OCCO4)cc1] | − |
| 2IE | 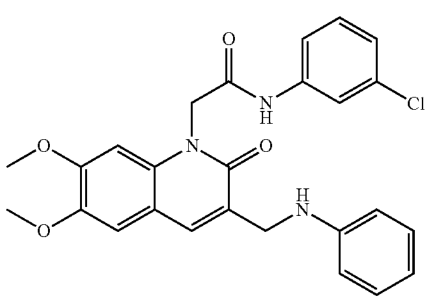 [SMILES: COc1cc2cc(CNc3ccccc3)c(=O)n(CC(=O)Nc3cccc(Cl)c3)c2cc1OC] | − |

TABLE 2-continued

Inhibition of FOXC2-expressing HMLER cells by Formula II Compounds

| Compound No. | Structure | Activity Score |
|---|---|---|
| 2IF | 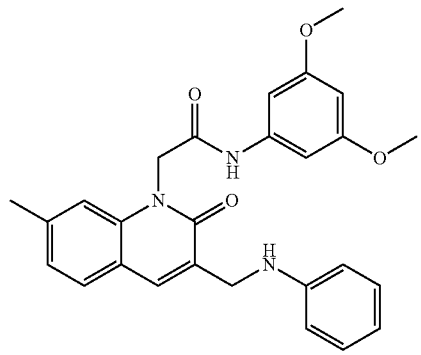 | − |
| 2IG | 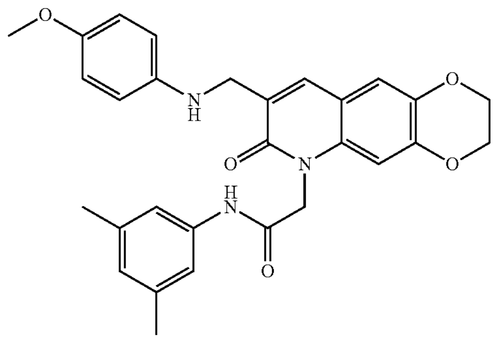 [SMILES: COc1ccc(NCc2cc3cc4c(cc3n(CC(=O)Nc3cc(C)cc(C)c3)c2=O)OCCO4)cc1] | − |
| 2IH | 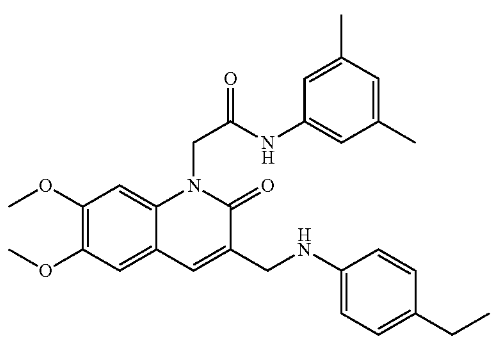 [SMILES: CCc1ccc(NCc2cc3cc(OC)c(OC)cc3n(CC(=O)Nc3cc(C)cc(C)c3)c2=O)cc1] | − |
| 2II | 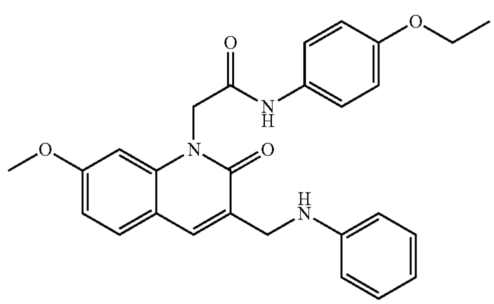 [SMILES: CCOc1ccc(NC(=O)Cn2c(=O)c(CNc3ccccc3)cc3ccc(OC)cc32)cc1] | − |

TABLE 2-continued

Inhibition of FOXC2-expressing HMLER cells by Formula II Compounds

| Compound No. | Structure | Activity Score |
|---|---|---|
| 2IJ | 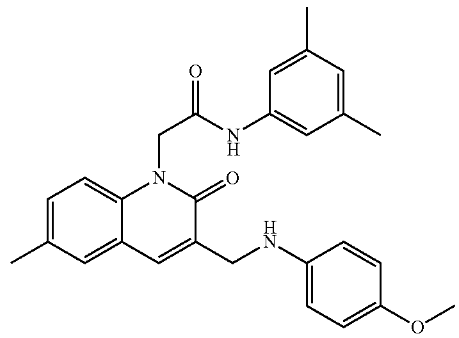 | − |
| 2IK | 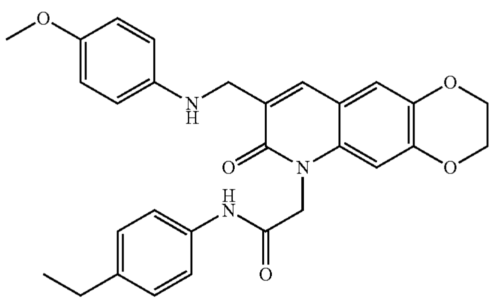 [SMILES: CCc1ccc(NC(=O)Cn2c(=O)c(CNc3ccc(OC)cc3)cc3cc4c(cc32)OCCO4)cc1] | − |
| 2IL | 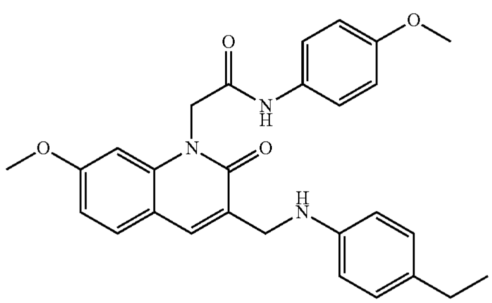 [SMILES: CCc1ccc(NCc2cc3ccc(OC)cc3n(CC(=O)Nc3ccc(OC)cc3)c2=O)cc1] | − |
| 2IM | 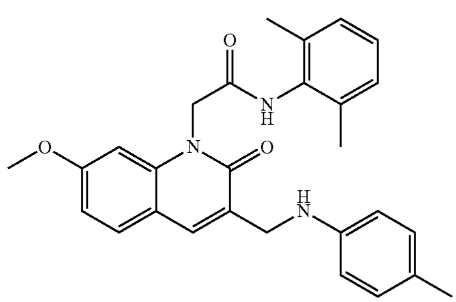 | − |

TABLE 3

Inhibition of FOXC2-expressing HMLER cells by Formula III Compounds

| Compound No. | Structure | Activity Score |
|---|---|---|
| 3A | 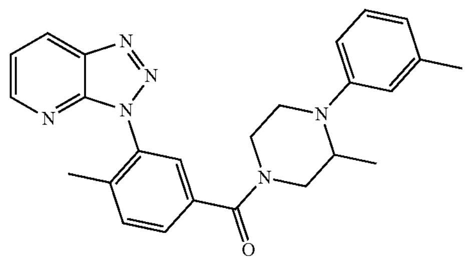 [SMILES: Cc1cccc(N2CCN(C(=O)c3ccc(C)c(-n4nnc5cccnc54)c3)CC2C)c1] | +++ |
| 3B | 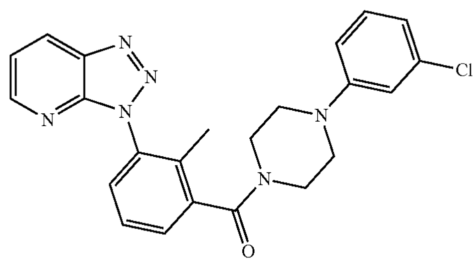 [SMILES: Cc1c(C(=O)N2CCN(c3cccc(Cl)c3)CC2)cccc1-n1nnc2cccnc21] | +++ |
| 3C | 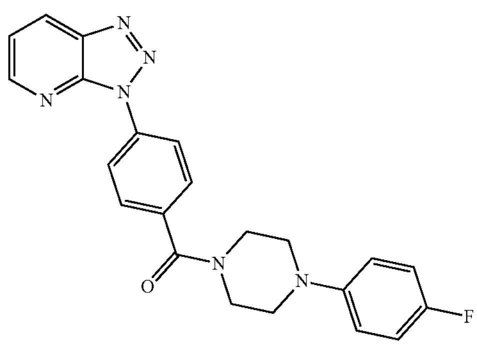 [SMILES: O=C(c1ccc(-n2nnc3cccnc32)cc1)N1CCN(c2ccc(F)cc2)CC1] | ++ |
| 3D | 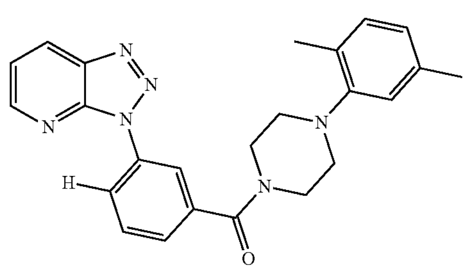 | ++ |
| 3E | 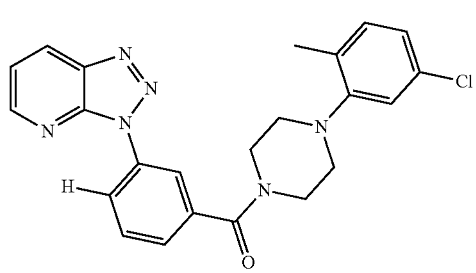 | ++ |

TABLE 3-continued

Inhibition of FOXC2-expressing HMLER cells by Formula III Compounds

| Compound No. | Structure | Activity Score |
|---|---|---|
| 3F | 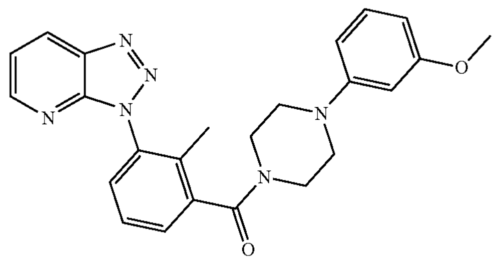 [SMILES: COc1cccc(N2CCN(C(=O)c3cccc(-n4nnc5cccnc54)c3C)CC2)c1] | ++ |
| 3 | 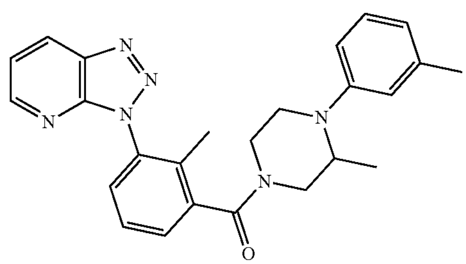 [SMILES: Cc1cccc(N2CCN(C(=O)c3cccc(-n4nnc5cccnc54)c3C)CC2C)c1] | ++ |
| 3G | 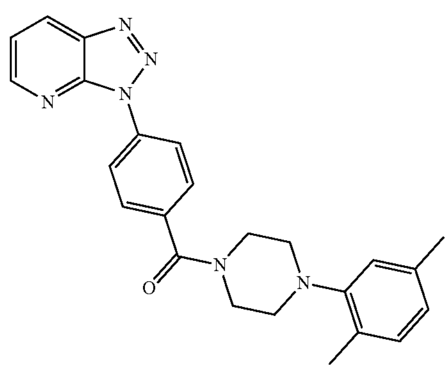 [SMILES: Cc1ccc(C)c(N2CCN(C(=O)c3ccc(-n4nnc5cccnc54)cc3)CC2)c1] | + |
| 3H | 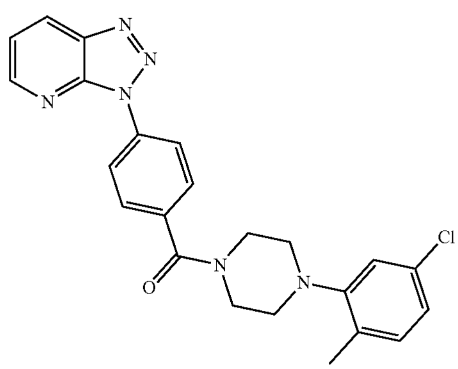 [SMILES: Cc1ccc(Cl)cc1N1CCN(C(=O)c2ccc(-n3nnc4cccnc43)cc2)CC1] | + |

TABLE 3-continued

Inhibition of FOXC2-expressing HMLER cells by Formula III Compounds

| Compound No. | Structure | Activity Score |
|---|---|---|
| 3I | 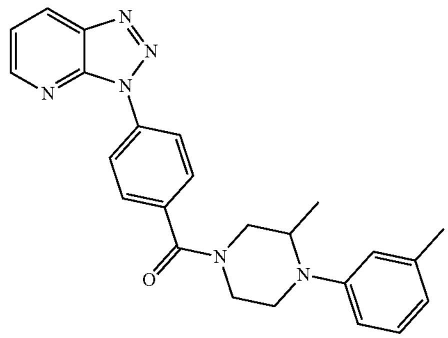 [SMILES: Cc1cccc(N2CCN(C(=O)c3ccc(-n4nnc5cccnc54)cc3)CC2C)c1] | + |
| 3J | 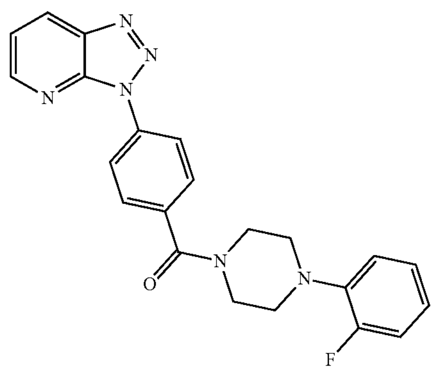 [SMILES: O=C(c1ccc(-n2nnc3cccnc32)cc1)N1CCN(c2ccccc2F)CC1] | + |
| 3K | 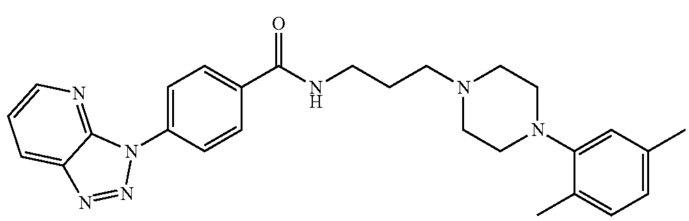 [SMILES: Cc1ccc(C)c(N2CCN(CCCNC(=O)c3ccc(-n4nnc5cccnc54)cc3)CC2)c1] | + |
| 3L | 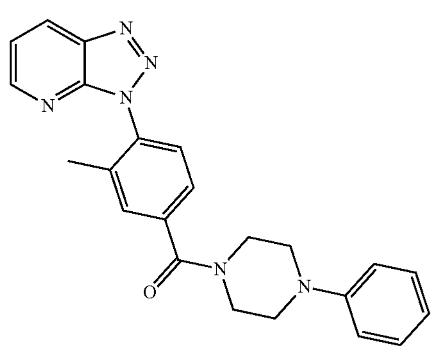 [SMILES: Cc1cc(C(=O)N2CCN(c3ccccc3)CC2)ccc1-n1nnc2cccnc21] | + |

TABLE 3-continued

Inhibition of FOXC2-expressing HMLER cells by Formula III Compounds

| Compound No. | Structure | Activity Score |
|---|---|---|
| 3M | [triazolopyridine-phenyl(methyl)-C(=O)-N-piperidine-4-benzyl] | + |
| 3N | [triazolopyridine-phenyl(methyl)-C(=O)-NH-piperidine-N-benzyl] | + |
| 3O | [triazolopyridine-phenyl(methyl)-C(=O)-NH-phenyl-CH2-pyrrolidine] | + |

TABLE 3-continued

Inhibition of FOXC2-expressing HMLER cells by Formula III Compounds

| Compound No. | Structure | Activity Score |
|---|---|---|
| 3P | 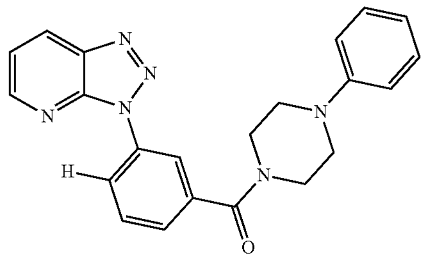 [SMILES: O=C(c1cccc(-n2nnc3cccnc32)c1)N1CCN(c2ccccc2)CC1] | + |
| 3Q | 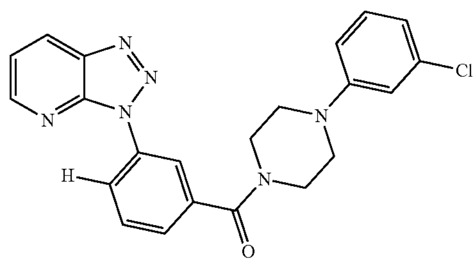 [SMILES: O=C(c1cccc(-n2nnc3cccnc32)c1)N1CCN(c2cccc(Cl)c2)CC1] | + |
| 3R | 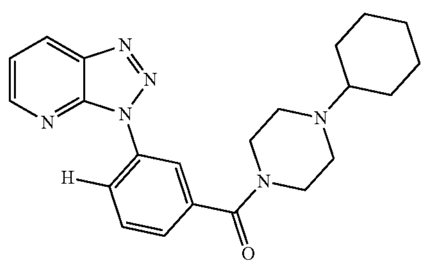 [SMILES: O=C(c1cccc(-n2nnc3cccnc32)c1)N1CCN(C2CCCCC2)CC1] | + |
| 3S | 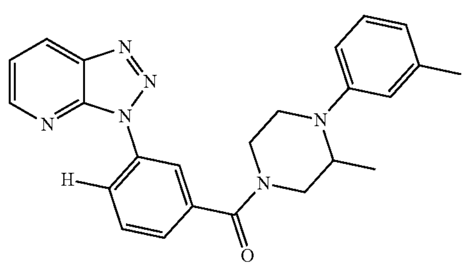 | + |
| 3T | 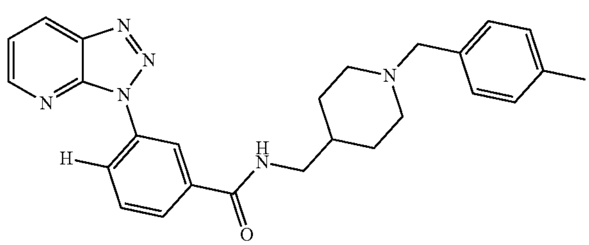 [SMILES: Cc1ccc(CN2CCC(CNC(=O)c3cccc(-n4nnc5cccnc54)c3)CC2)cc1] | + |

TABLE 3-continued

Inhibition of FOXC2-expressing HMLER cells by Formula III Compounds

| Compound No. | Structure | Activity Score |
|---|---|---|
| 3U | 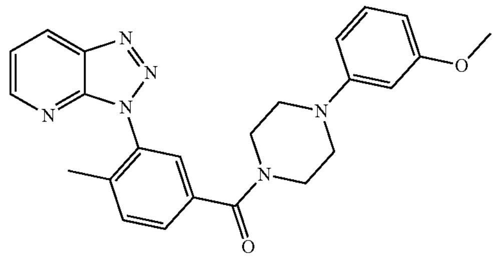 [SMILES: COc1cccc(N2CCN(C(=O)c3ccc(C)c(-n4nnc5cccnc54)c3)CC2)c1] | + |
| 3V | 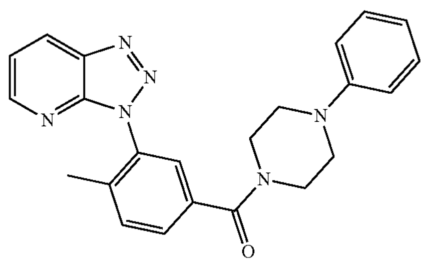 [SMILES: Cc1ccc(C(=O)N2CCN(c3ccccc3)CC2)cc1-n1nnc2cccnc21] | + |
| 3W | 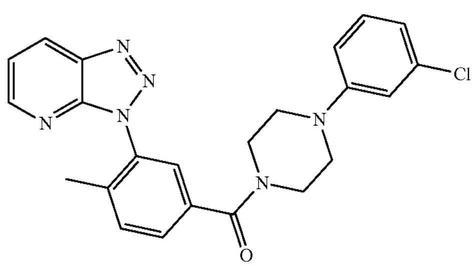 [SMILES: Cc1ccc(C(=O)N2CCN(c3cccc(Cl)c3)CC2)cc1-n1nnc2cccnc21] | + |
| 3X | 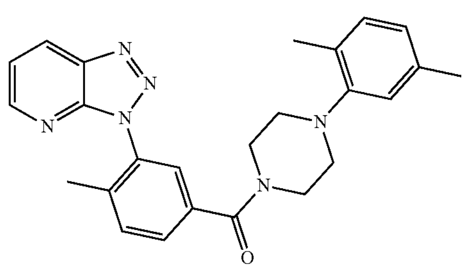 [SMILES: Cc1ccc(C)c(N2CCN(C(=O)c3ccc(C)c(-n4nnc5cccnc54)c3)CC2)c1] | + |
| 3Y | 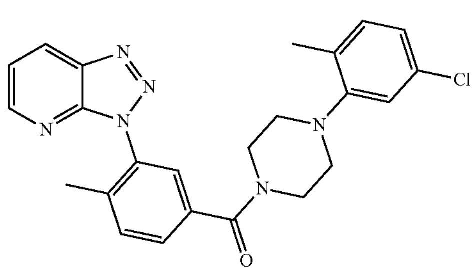 [SMILES: Cc1ccc(Cl)cc1N1CCN(C(=O)c2ccc(C)c(-n3nnc4cccnc43)c2)CC1] | + |

TABLE 3-continued

Inhibition of FOXC2-expressing HMLER cells by Formula III Compounds

| Compound No. | Structure | Activity Score |
|---|---|---|
| 3Z | 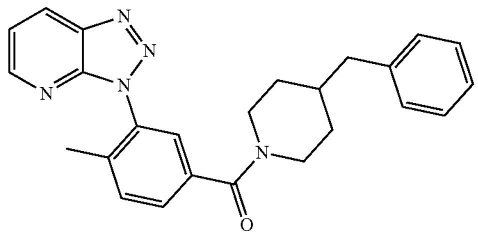 [SMILES: Cc1ccc(C(=O)N2CCC(Cc3ccccc3)CC2)cc1-n1nnc2cccnc21] | + |
| 3AA | 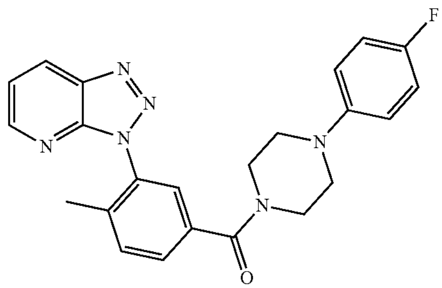 [SMILES: Cc1ccc(C(=O)N2CCN(c3ccc(F)cc3)CC2)cc1-n1nnc2cccnc21] | + |
| 3AB | 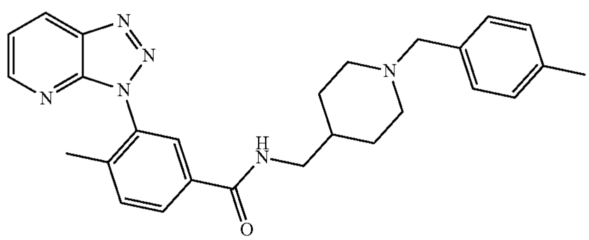 [SMILES: Cc1ccc(CN2CCC(CNC(=O)c3ccc(C)c(-n4nnc5cccnc54)c3)CC2)cc1] | + |
| 3AC | 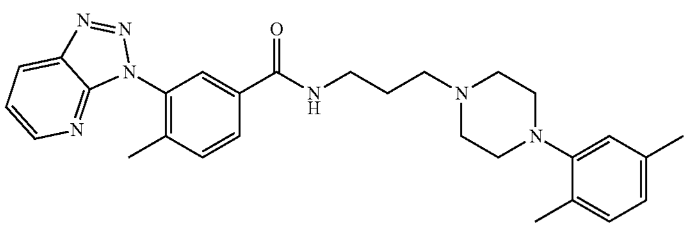 [SMILES: Cc1ccc(C)c(N2CCN(CCCNC(=O)c3ccc(C)c(-n4nnc5cccnc54)c3)CC2)c1] | + |
| 3AD | 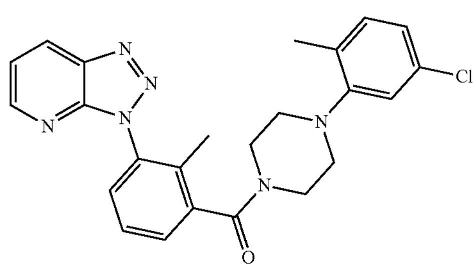 [SMILES: Cc1ccc(Cl)cc1N1CCN(C(=O)c2cccc(-n3nnc4cccnc43)c2C)CC1] | + |
| 3AE | 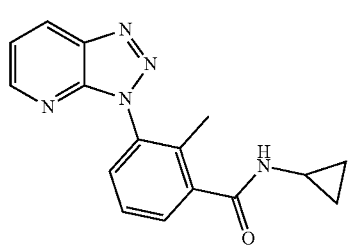 [SMILES: Cc1c(C(=O)NC2CC2)cccc1-n1nnc2cccnc21] | + |

TABLE 3-continued

Inhibition of FOXC2-expressing HMLER cells by Formula III Compounds

| Compound No. | Structure | Activity Score |
|---|---|---|
| 3AF | 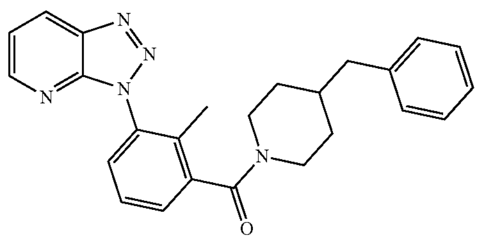 [SMILES: Cc1c(C(=O)N2CCC(Cc3ccccc3)CC2)cccc1-n1nnc2cccnc21] | + |
| 3AG | | + |
| 3AG | | + |
| 3AH | 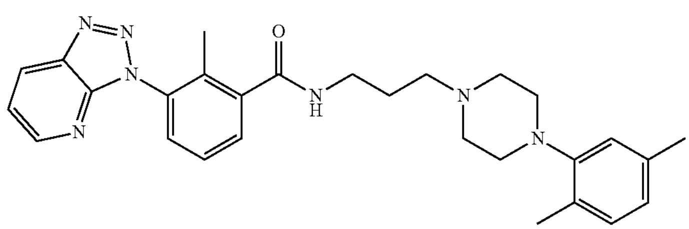 [SMILES: Cc1ccc(C)c(N2CCN(CCCNC(=O)c3cccc(-n4nnc5cccnc54)c3C)CC2)c1] | + |
| 3AI | 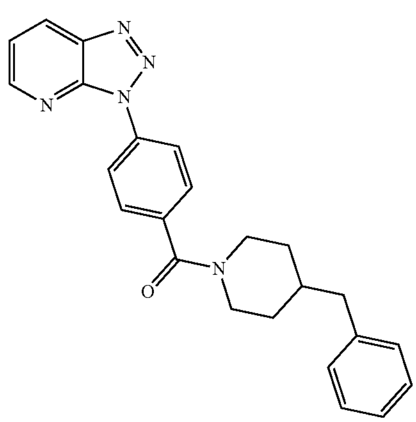 [SMILES: O=C(c1ccc(-n2nnc3cccnc32)cc1)N1CCC(Cc2ccccc2)CC1] | + |

TABLE 3-continued

Inhibition of FOXC2-expressing HMLER cells by Formula III Compounds

| Compound No. | Structure | Activity Score |
|---|---|---|
| 3AJ | 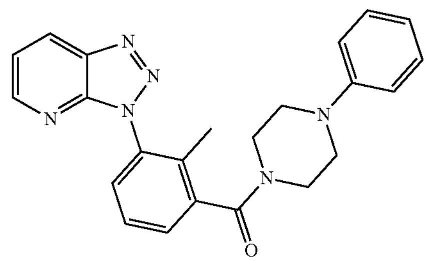 [SMILES: Cc1c(C(=O)N2CCN(c3ccccc3)CC2)cccc1-n1nnc2cccnc21] | + |
| 3AK | 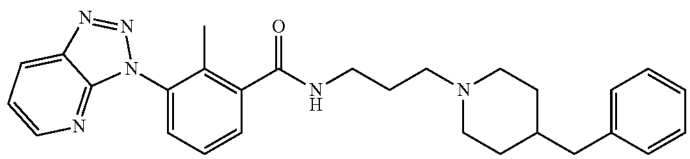 [SMILES: Cc1c(C(=O)NCCCN2CCC(Cc3ccccc3)CC2)cccc1-n1nnc2cccnc21] | + |
| 3AL | 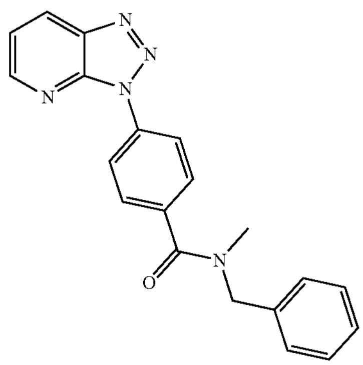 [SMILES: CN(Cc1ccccc1)C(=O)c1ccc(-n2nnc3cccnc32)cc1] | − |
| 3AM | 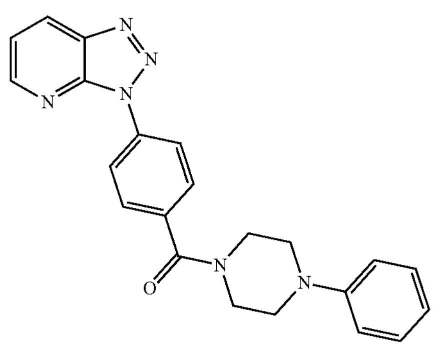 [SMILES: O=C(c1ccc(-n2nnc3cccnc32)cc1)N1CCN(c2ccccc2)CC1] | − |
| 3AN | 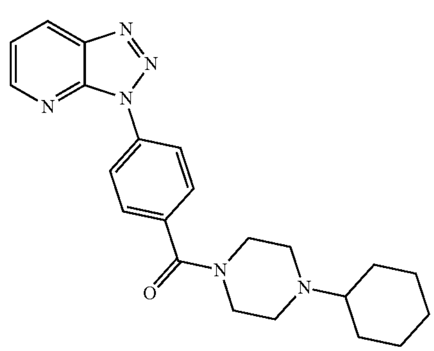 [SMILES: O=C(c1ccc(-n2nnc3cccnc32)cc1)N1CCN(C2CCCCC2)CC1] | − |

TABLE 3-continued

Inhibition of FOXC2-expressing HMLER cells by Formula III Compounds

| Compound No. | Structure | Activity Score |
|---|---|---|
| 3AO | 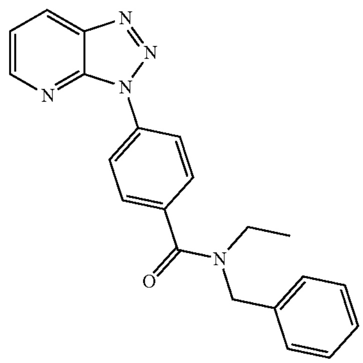 [SMILES: CCN(Cc1ccccc1)C(=O)c1ccc(-n2nnc3cccnc32)cc1] | – |
| 3AP | 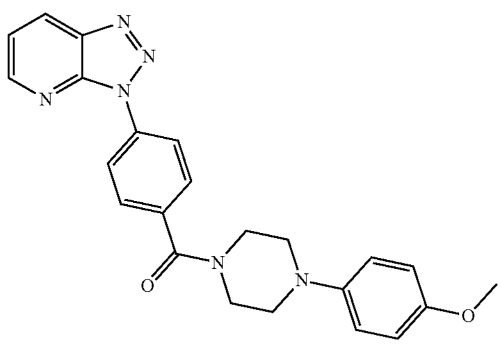 [SMILES: COc1ccc(N2CCN(C(=O)c3ccc(-n4nnc5cccnc54)cc3)CC2)cc1] | – |
| 3AQ | 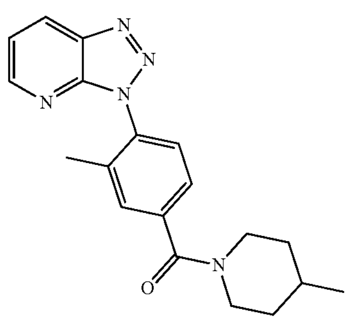 [SMILES: Cc1cc(C(=O)N2CCC(C)CC2)ccc1-n1nnc2cccnc21] | – |
| 3AR | 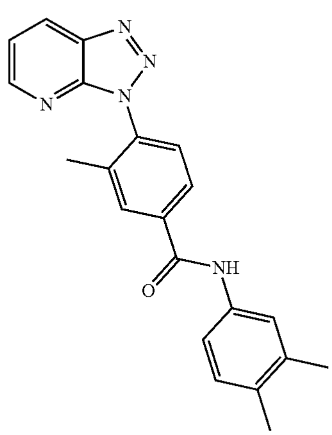 [SMILES: Cc1ccc(NC(=O)c2ccc(-n3nnc4cccnc43)c(C)c2)cc1C] | – |

TABLE 3-continued

Inhibition of FOXC2-expressing HMLER cells by Formula III Compounds

| Compound No. | Structure | Activity Score |
|---|---|---|
| 3AS | 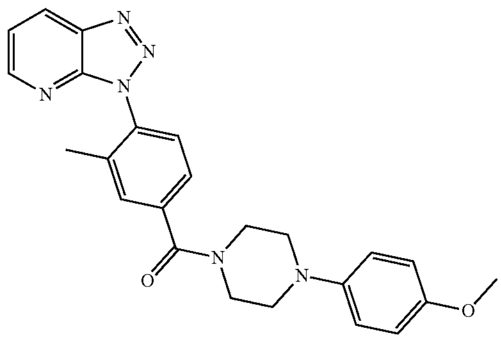 [SMILES: COc1ccc(N2CCN(C(=O)c3ccc(-n4nnc5cccnc54)c(C)c3)CC2)cc1] | – |
| 3AT | 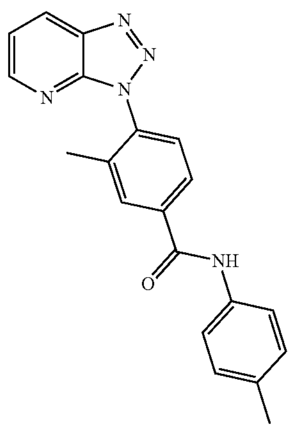 [SMILES: Cc1ccc(NC(=O)c2ccc(-n3nnc4cccnc43)c(C)c2)cc1] | – |
| 3AU | 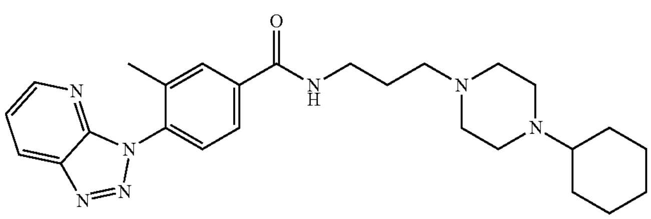 [SMILES: Cc1cc(C(=O)NCCCN2CCN(C3CCCCC3)CC2)ccc1-n1nnc2cccnc21] | – |
| 3AV | 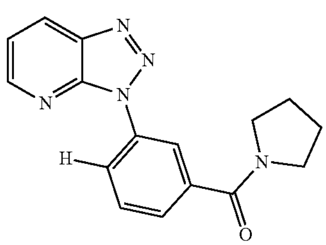 [SMILES: O=C(c1cccc(-n2nnc3cccnc32)c1)N1CCCC1] | – |
| 3AW | 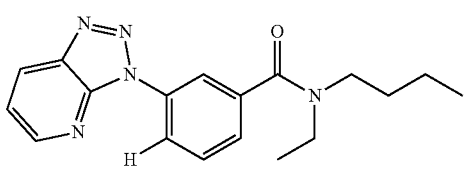 [SMILES: CCCCN(CC)C(=O)c1cccc(-n2nnc3cccnc32)c1] | – |

TABLE 3-continued

Inhibition of FOXC2-expressing HMLER cells by Formula III Compounds

| Compound No. | Structure | Activity Score |
|---|---|---|
| 3AX | 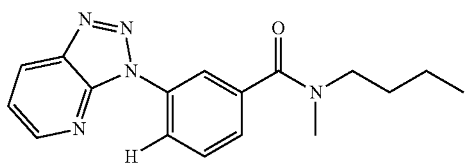 [SMILES: CCCCN(C)C(=O)c1cccc(-n2nnc3cccnc32)c1] | – |
| 3AY | 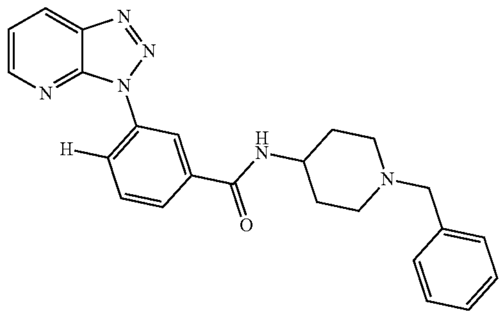 [SMILES: O=C(NC1CCN(Cc2ccccc2)CC1)c1cccc(-n2nnc3cccnc32)c1] | – |
| 3AZ | 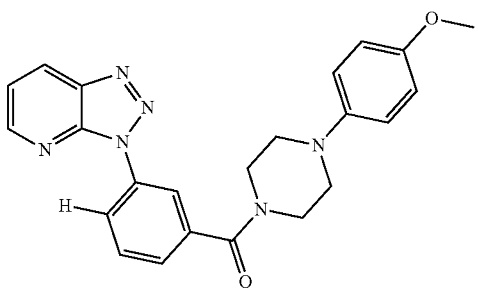 [SMILES: COc1ccc(N2CCN(C(=O)c3cccc(-n4nnc5cccnc54)c3)CC2)cc1] | – |
| 3BA | 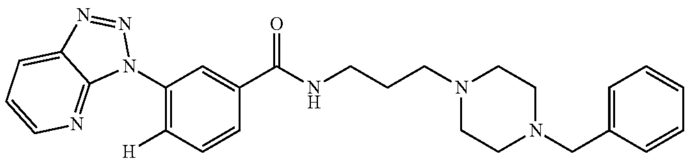 [SMILES: O=C(NCCCN1CCN(Cc2ccccc2)CC1)c1cccc(-n2nnc3cccnc32)c1] | – |
| 3BB | 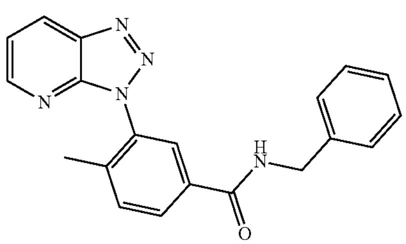 [SMILES: Cc1ccc(C(=O)NCc2ccccc2)cc1-n1nnc2cccnc21] | – |
| 3BC | 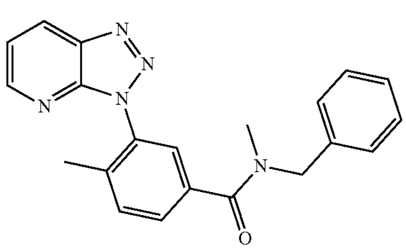 [SMILES: Cc1ccc(C(=O)N(C)Cc2ccccc2)cc1-n1nnc2cccnc21] | – |

TABLE 3-continued

Inhibition of FOXC2-expressing HMLER cells by Formula III Compounds

| Compound No. | Structure | Activity Score |
|---|---|---|
| 3BD | 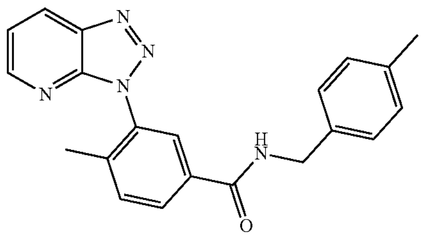 [SMILES: Cc1ccc(CNC(=O)c2ccc(C)c(-n3nnc4cccnc43)c2)cc1] | − |
| 3BE | 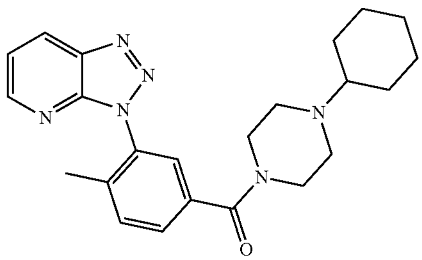 [SMILES: Cc1ccc(C(=O)N2CCN(C3CCCCC3)CC2)cc1-n1nnc2cccnc21] | − |
| 3BF | 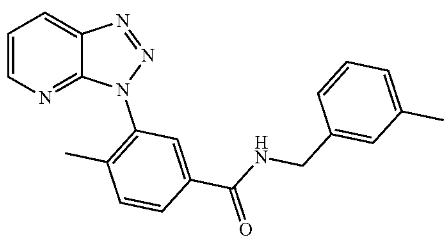 [SMILES: Cc1cccc(CNC(=O)c2ccc(C)c(-n3nnc4cccnc43)c2)c1] | − |
| 3BG | 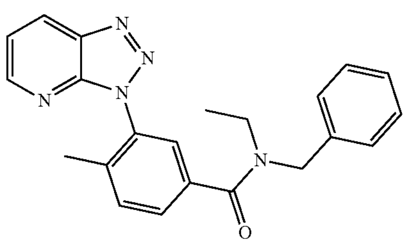 [SMILES: CCN(Cc1ccccc1)C(=O)c1ccc(C)c(-n2nnc3cccnc32)c1] | − |
| 3BH | 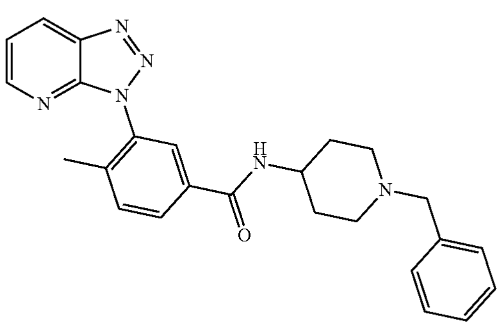 [SMILES: Cc1ccc(C(=O)NC2CCN(Cc3ccccc3)CC2)cc1-n1nnc2cccnc21] | − |

TABLE 3-continued

Inhibition of FOXC2-expressing HMLER cells by Formula III Compounds

| Compound No. | Structure | Activity Score |
|---|---|---|
| 3BI | 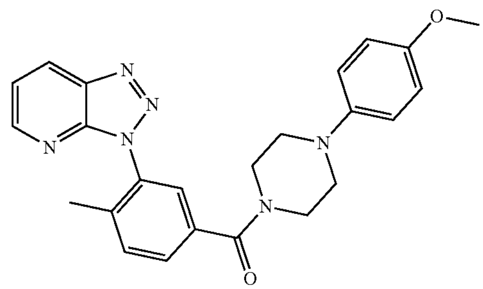 [SMILES: COc1ccc(N2CCN(C(=O)c3ccc(C)c(-n4nnc5cccnc54)c3)CC2)cc1] | – |
| 3BJ | 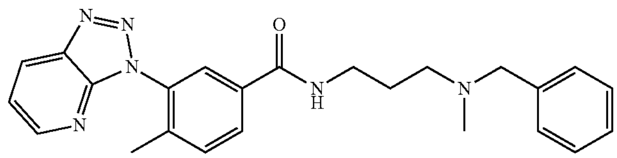 [SMILES: Cc1ccc(C(=O)NCCCN(C)Cc2ccccc2)cc1-n1nnc2cccnc21] | – |
| 3BK | 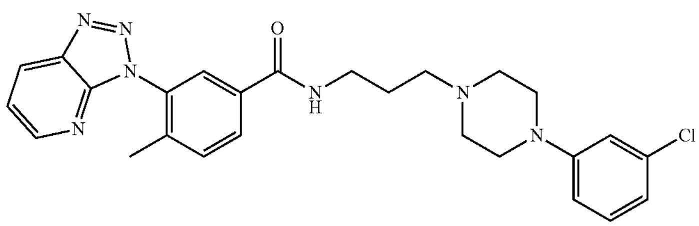 [SMILES: Cc1ccc(C(=O)NCCCN2CCN(c3cccc(Cl)c3)CC2)cc1-n1nnc2cccnc21] | – |
| 3BL | 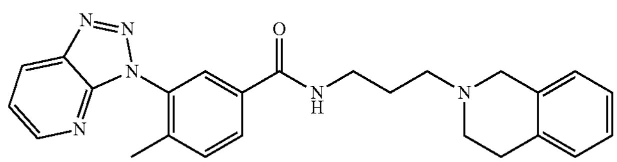 [SMILES: Cc1ccc(C(=O)NCCCN2CCc3ccccc3C2)cc1-n1nnc2cccnc21] | – |
| 3BM | 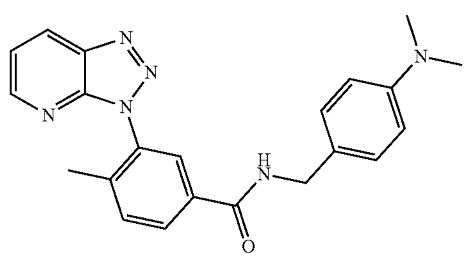 [SMILES: Cc1ccc(C(=O)NCc2ccc(N(C)C)cc2)cc1-n1nnc2cccnc21] | – |
| 3BN | 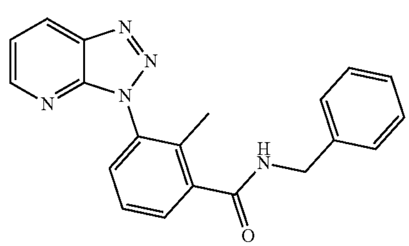 [SMILES: Cc1c(C(=O)NCc2ccccc2)cccc1-n1nnc2cccnc21] | – |

TABLE 3-continued

Inhibition of FOXC2-expressing HMLER cells by Formula III Compounds

| Compound No. | Structure | Activity Score |
|---|---|---|
| 3BO | 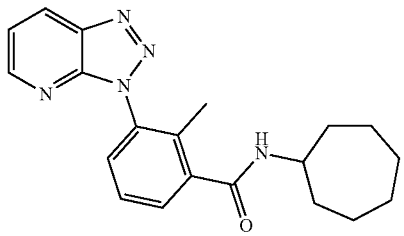 [SMILES: Cc1c(C(=O)NC2CCCCCC2)cccc1-n1nnc2cccnc21] | − |
| 3BP | 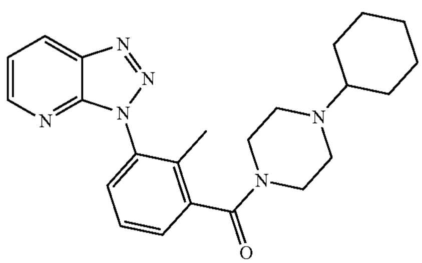 [SMILES: Cc1c(C(=O)N2CCN(C3CCCCC3)CC2)cccc1-n1nnc2cccnc21] | − |
| 3BQ | 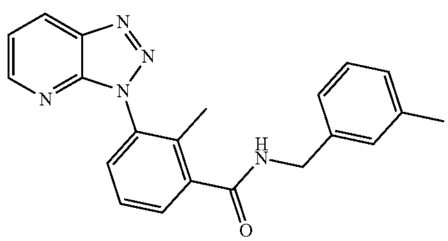 [SMILES: Cc1cccc(CNC(=O)c2cccc(-n3nnc4cccnc43)c2C)c1] | − |
| 3BR | 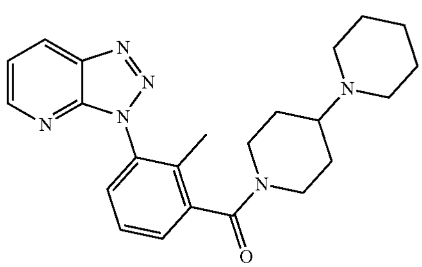 [SMILES: Cc1c(C(=O)N2CCC(N3CCCCC3)CC2)cccc1-n1nnc2cccnc21] | − |
| 3BS | 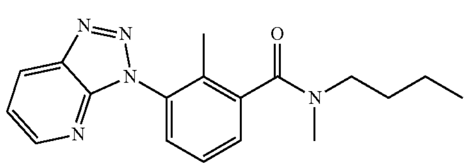 [SMILES: CCCCN(C)C(=O)c1cccc(-n2nnc3cccnc32)c1C] | − |
| 3BT | 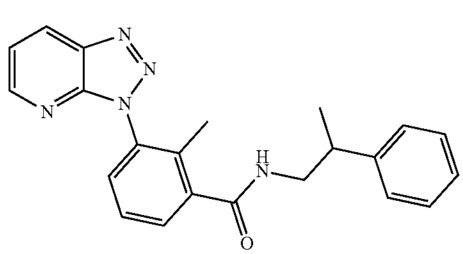 [SMILES: Cc1c(C(=O)NCC(C)c2ccccc2)cccc1-n1nnc2cccnc21] | − |

TABLE 3-continued
Inhibition of FOXC2-expressing HMLER cells by Formula III Compounds
| Compound No. | Structure | Activity Score |
|---|---|---|
| 3BU | 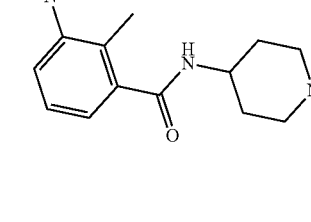 | – |
| 3BV | 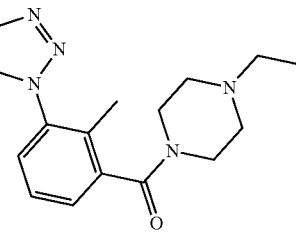 | – |
| 3BW | 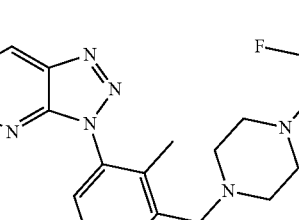 | – |
| 3BX | 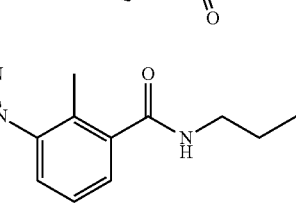 | – |
| 3BY | 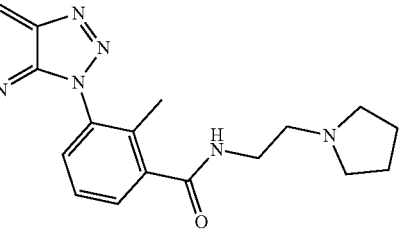 | – |
| 3BZ | 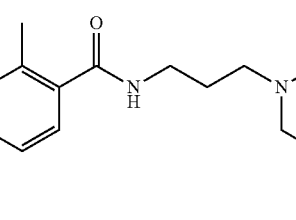 | – |

TABLE 3-continued

Inhibition of FOXC2-expressing HMLER cells by Formula III Compounds

| Compound No. | Structure | Activity Score |
|---|---|---|
| 3CA | 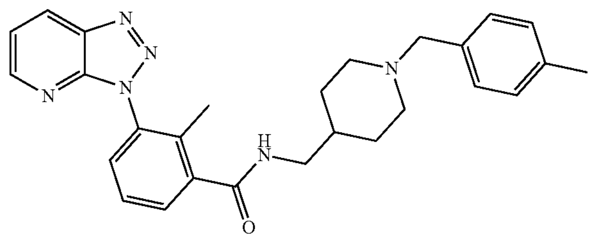 [SMILES: Cc1ccc(CN2CCC(CNC(=O)c3cccc(-n4nnc5cccnc54)c3C)CC2)cc1] | − |
| 3CB | 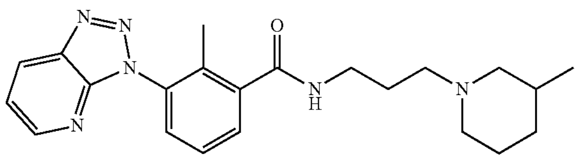 [SMILES: Cc1c(C(=O)NCCCN2CCCC(C)C2)cccc1-n1nnc2cccnc21] | − |
| 3CC | 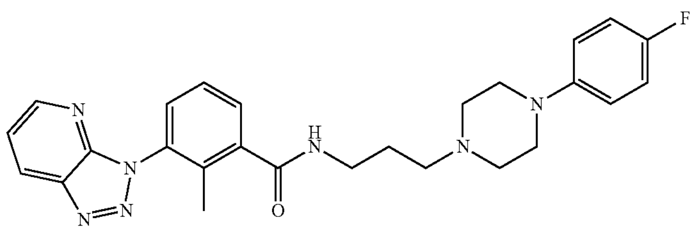 [SMILES: Cc1c(C(=O)NCCCN2CCN(c3ccc(F)cc3)CC2)cccc1-n1nnc2cccnc21] | − |
| 3CD | 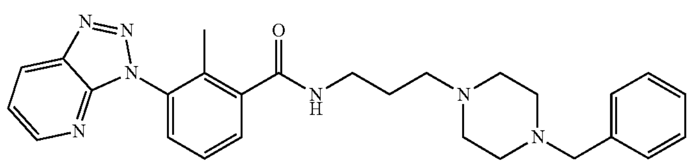 [SMILES: Cc1c(C(=O)NCCCN2CCN(Cc3ccccc3)CC2)cccc1-n1nnc2cccnc21] | − |
| 3CE | 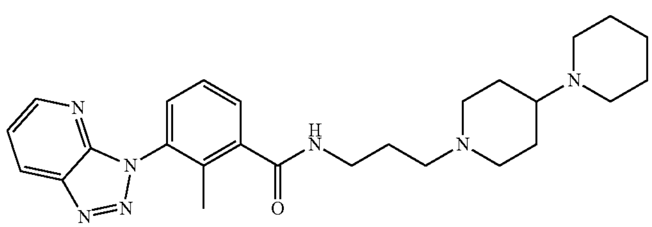 [SMILES: Cc1c(C(=O)NCCCN2CCC(N3CCCCC3)CC2)cccc1-n1nnc2cccnc21] | − |
| 3CF | 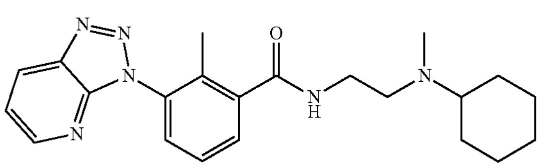 [SMILES: Cc1c(C(=O)NCCN(C)C2CCCCC2)cccc1-n1nnc2cccnc21] | − |
| 3CG | 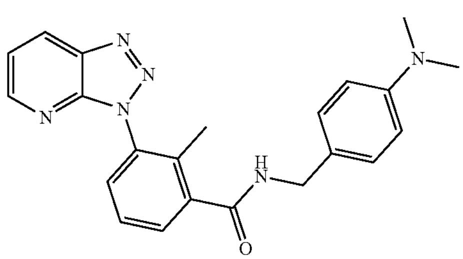 [SMILES: Cc1c(C(=O)NCc2ccc(N(C)C)cc2)cccc1-n1nnc2cccnc21] | − |

TABLE 3-continued

Inhibition of FOXC2-expressing HMLER cells by Formula III Compounds

| Compound No. | Structure | Activity Score |
|---|---|---|
| 3CH | 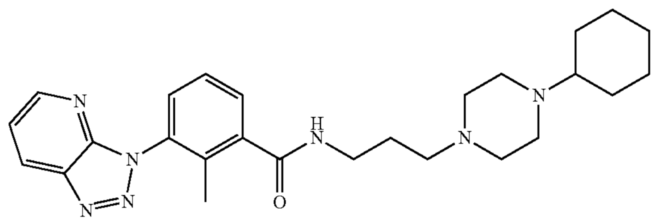 [SMILES: Cc1c(C(=O)NCCCN2CCN(C3CCCCC3)CC2)cccc1-n1nnc2cccnc21] | − |
| 3CI | 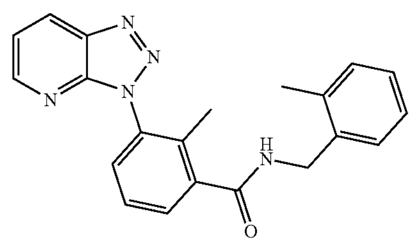 [SMILES: Cc1ccccc1CNC(=O)c1cccc(-n2nnc3cccnc32)c1C] | − |
| 3CJ | 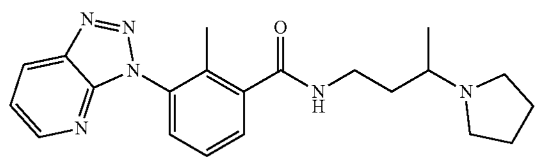 [SMILES: Cc1c(C(=O)NCCC(C)N2CCCC2)cccc1-n1nnc2cccnc21] | − |
| 3CK | 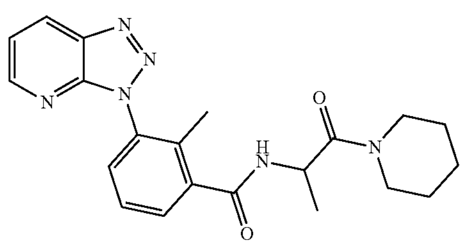 [SMILES: Cc1c(C(=O)NC(C)C(=O)N2CCCCC2)cccc1-n1nnc2cccnc21] | − |

TABLE 4

Inhibition of FOXC2-expressing HMLER cells by Formula IV Compounds

| Compound No. | Structures | Activity Score |
|---|---|---|
| 4A | 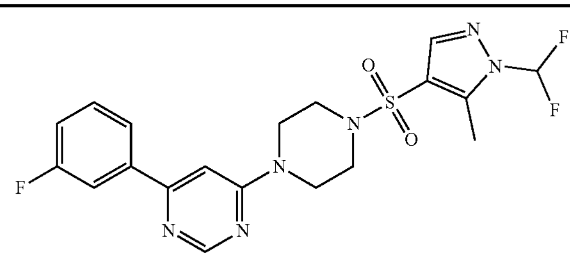 | +++ |

TABLE 4-continued

Inhibition of FOXC2-expressing HMLER cells by Formula IV Compounds

| Compound No. | Structures | Activity Score |
|---|---|---|
| 4B | 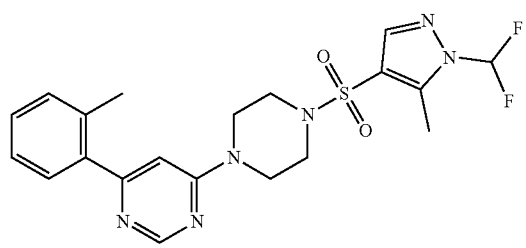 [SMILES: Cc1ccccc1-c1cc(N2CCN(S(=O)(=O)c3cnn(C(F)F)c3C)CC2)ncn1] | +++ |
| 4C | 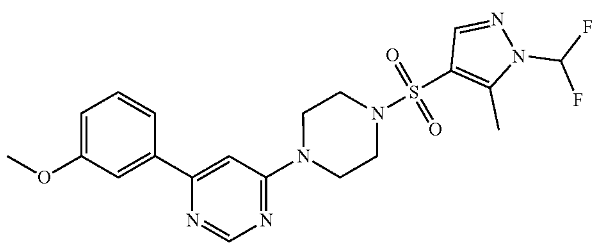 [SMILES: COc1cccc(-c2cc(N3CCN(S(=O)(=O)c4cnn(C(F)F)c4C)CC3)ncn2)c1] | +++ |
| 4D | 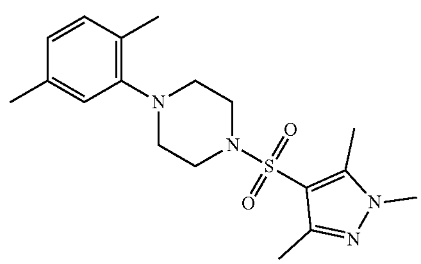 | ++ |
| 4E | 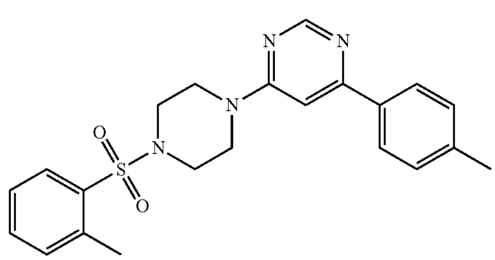 [SMILES: Cc1ccc(-c2cc(N3CCN(S(=O)(=O)c4ccccc4C)CC3)ncn2)cc1] | ++ |
| 4 | 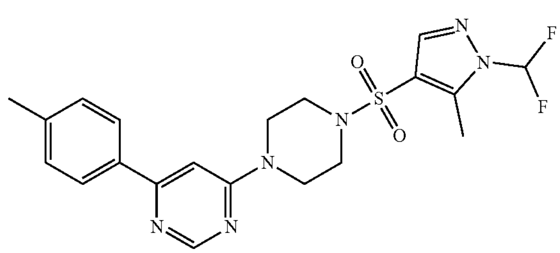 [SMILES: Cc1ccc(-c2cc(N3CCN(S(=O)(=O)c4cnn(C(F)F)c4C)CC3)ncn2)cc1] | ++ |

TABLE 4-continued

Inhibition of FOXC2-expressing HMLER cells by Formula IV Compounds

| Compound No. | Structures | Activity Score |
|---|---|---|
| 4F | 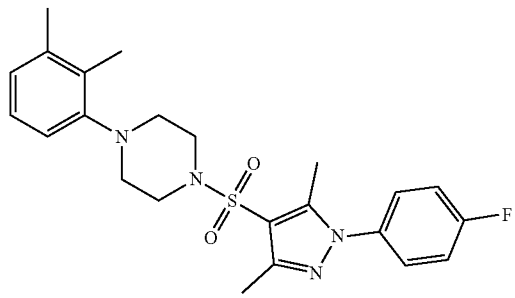 [SMILES: Cc1cccc(N2CCN(S(=O)(=O)c3c(C)nn(-c4ccc(F)cc4)c3C)CC2)c1C] | ++ |
| 4G | 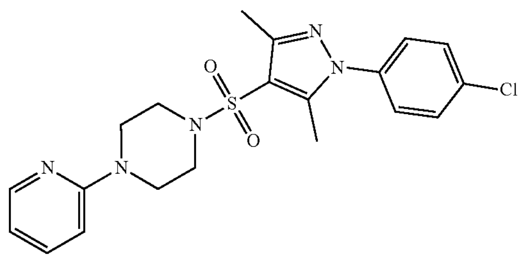 [SMILES: Cc1nn(-c2ccc(Cl)cc2)c(C)c1S(=O)(=O)N1CCN(c2ccccn2)CC1] | ++ |
| 4H | 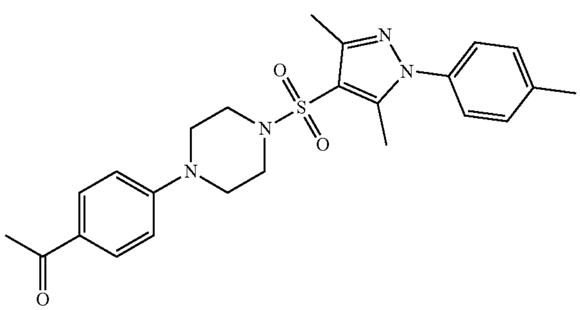 [SMILES: CC(=O)c1ccc(N2CCN(S(=O)(=O)c3c(C)nn(-c4ccc(C)cc4)c3C)CC2)cc1] | ++ |
| 4I | 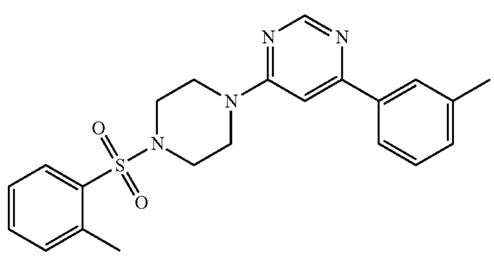 [SMILES: Cc1cccc(-c2cc(N3CCN(S(=O)(=O)c4ccccc4C)CC3)ncn2)c1] | + |
| 4J | 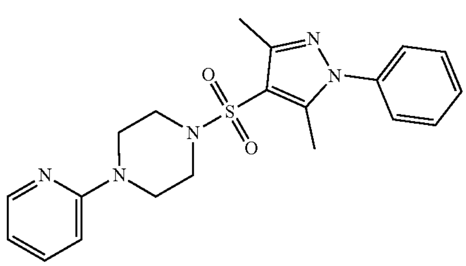 [SMILES: Cc1nn(-c2ccccc2)c(C)c1S(=O)(=O)N1CCN(c2ccccn2)CC1] | + |

TABLE 4-continued

Inhibition of FOXC2-expressing HMLER cells by Formula IV Compounds

| Compound No. | Structures | Activity Score |
|---|---|---|
| 4K | 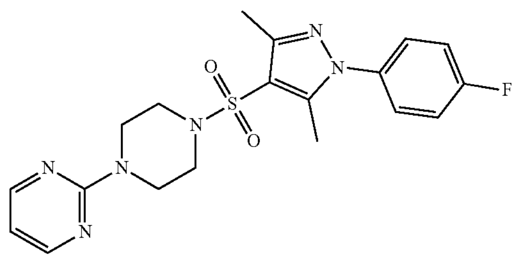 [SMILES: Cc1nn(-c2ccc(F)cc2)c(C)c1S(=O)(=O)N1CCN(c2ncccn2)CC1] | + |
| 4L | 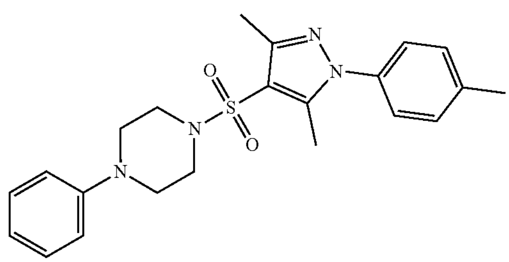 [SMILES: Cc1ccc(-n2nc(C)c(S(=O)(=O)N3CCN(c4ccccc4)CC3)c2C)cc1] | + |
| 4M | 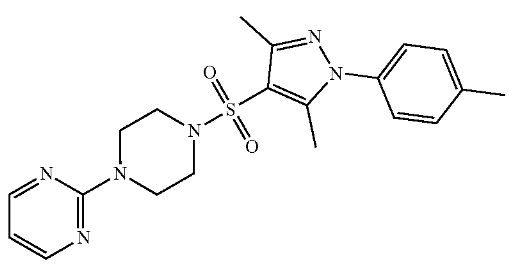 [SMILES: Cc1ccc(-n2nc(C)c(S(=O)(=O)N3CCN(c4ncccn4)CC3)c2C)cc1] | + |
| 4N | 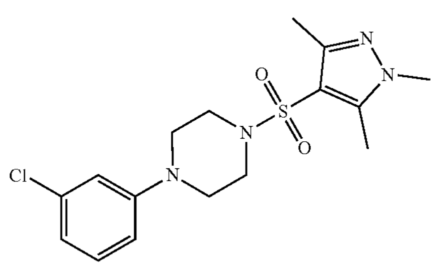 [SMILES: Cc1nn(C)c(C)c1S(=O)(=O)N1CCN(c2cccc(Cl)c2)CC1] | − |
| 4O | 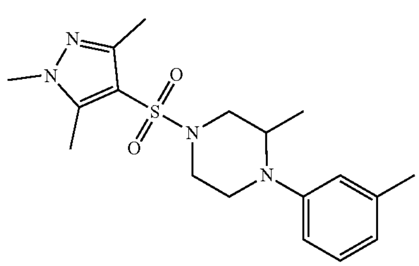 | − |

TABLE 4-continued

Inhibition of FOXC2-expressing HMLER cells by Formula IV Compounds

| Compound No. | Structures | Activity Score |
|---|---|---|
| 4P | 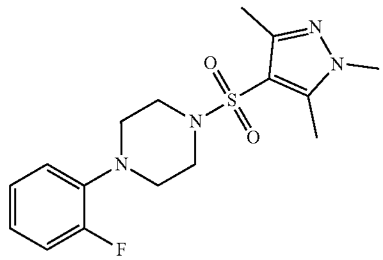 [SMILES: Cc1nn(C)c(C)c1S(=O)(=O)N1CCN(c2ccccc2F)CC1] | − |
| 4Q | 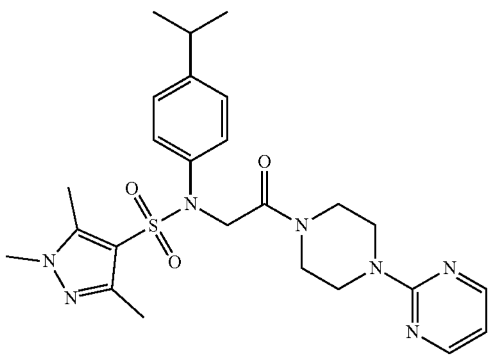 [SMILES: Cc1nn(C)c(C)c1S(=O)(=O)N(CC(=O)N1CCN(c2ncccn2)CC1)c1ccc(C(C)C)cc1] | − |
| 4R | 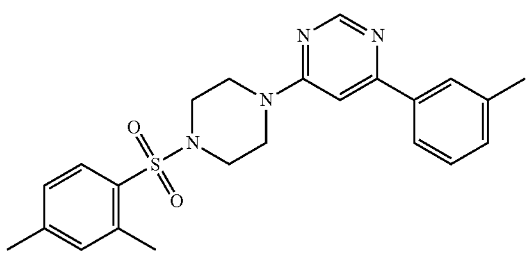 | − |
| 4S | 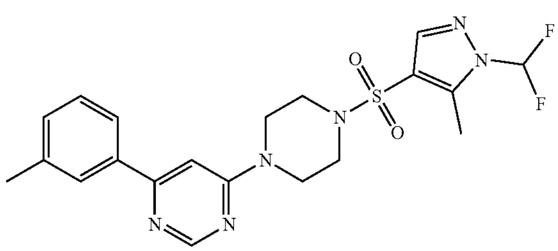 [SMILES: Cc1cccc(-c2cc(N3CCN(S(=O)(=O)c4cnn(C(F)F)c4C)CC3)ncn2)c1] | − |
| 4T | 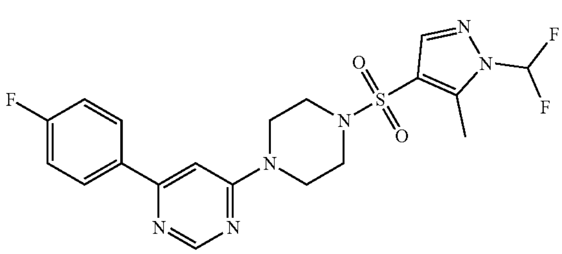 [SMILES: Cc1c(S(=O)(=O)N2CCN(c3cc(-c4ccc(F)cc4)ncn3)CC2)cnn1C(F)F] | − |

TABLE 4-continued
Inhibition of FOXC2-expressing HMLER cells by Formula IV Compounds
| Compound No. | Structures | Activity Score |
|---|---|---|
| 4U | 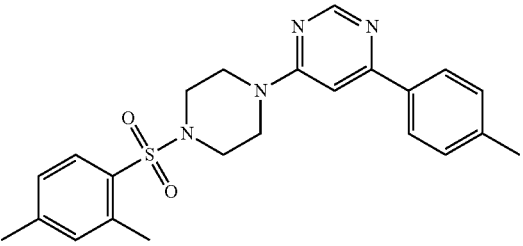 | – |
| 4V | 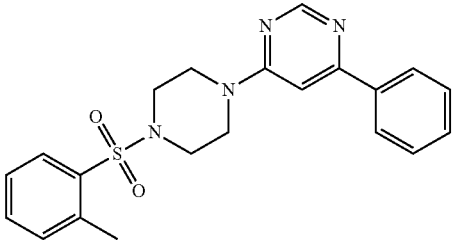 [SMILES: Cc1ccccc1S(=O)(=O)N1CCN(c2cc(-c3ccccc3)ncn2)CC1] | – |
| 4W | 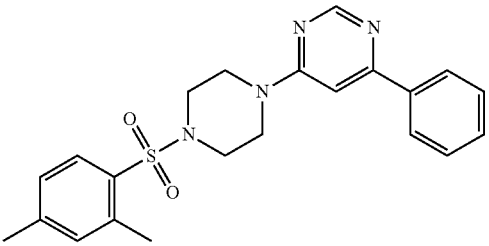 [SMILES: Cc1ccc(S(=O)(=O)N2CCN(c3cc(-c4ccccc4)ncn3)CC2)c(C)c1] | – |
| 4X | 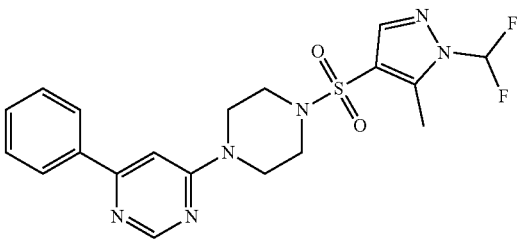 [SMILES: Cc1c(S(=O)(=O)N2CCN(c3cc(-c4ccccc4)ncn3)CC2)cnn1C(F)F] | – |
| 4Y | 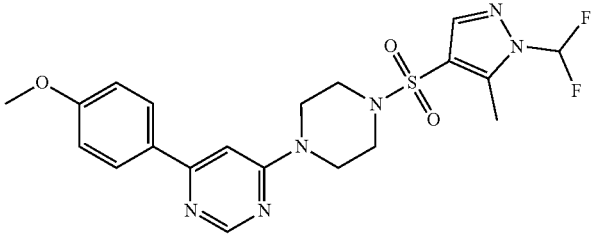 [SMILES: COc1ccc(-c2cc(N3CCN(S(=O)(=O)c4cnn(C(F)F)c4C)CC3)ncn2)cc1] | – |
| 4Z | 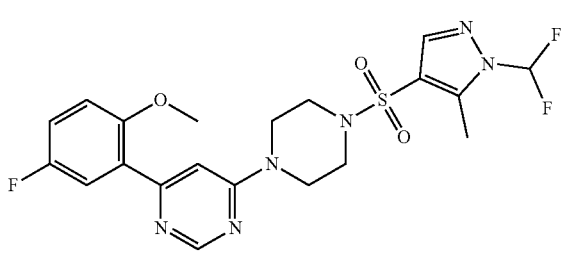 [SMILES: COc1ccc(F)cc1-c1cc(N2CCN(S(=O)(=O)c3cnn(C(F)F)c3C)CC2)ncn1] | – |

TABLE 4-continued

Inhibition of FOXC2-expressing HMLER cells by Formula IV Compounds

| Compound No. | Structures | Activity Score |
|---|---|---|
| 4AA | 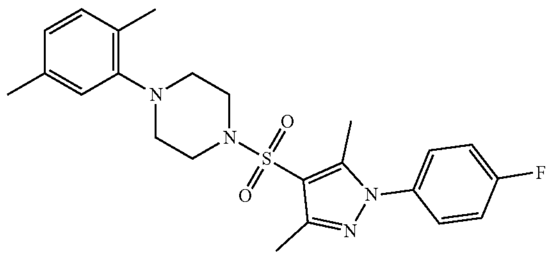 [SMILES: Cc1ccc(C)c(N2CCN(S(=O)(=O)c3c(C)nn(-c4ccc(F)cc4)c3C)CC2)c1] | − |
| 4AB | 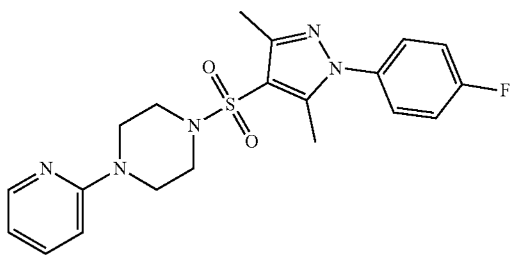 [SMILES: Cc1nn(-c2ccc(F)cc2)c(C)c1S(=O)(=O)N1CCN(c2ccccn2)CC1] | − |
| 4AC | 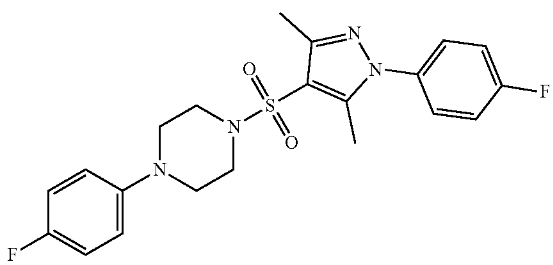 [SMILES: Cc1nn(-c2ccc(F)cc2)c(C)c1S(=O)(=O)N1CCN(c2ccc(F)cc2)CC1] | − |
| 4AD | 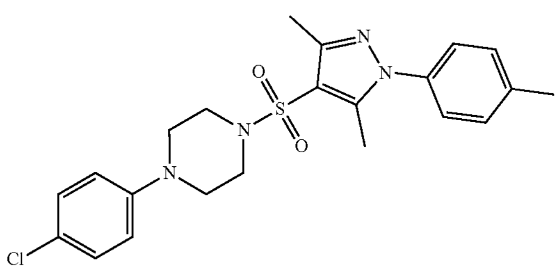 [SMILES: Cc1ccc(-n2nc(C)c(S(=O)(=O)N3CCN(c4ccc(Cl)cc4)CC3)c2C)cc1] | − |
| 4AE | 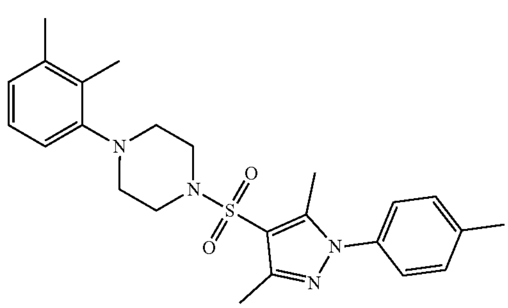 [SMILES: Cc1ccc(-n2nc(C)c(S(=O)(=O)N3CCN(c4cccc(C)c4C)CC3)c2C)cc1] | − |

TABLE 4-continued

Inhibition of FOXC2-expressing HMLER cells by Formula IV Compounds

| Compound No. | Structures | Activity Score |
|---|---|---|
| 4AF | 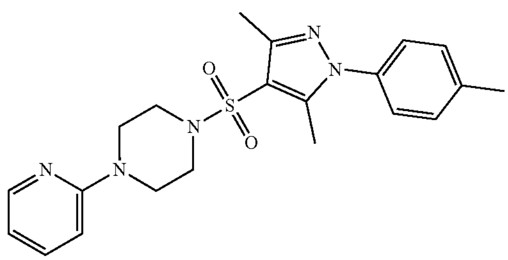 [SMILES: Cc1ccc(-n2nc(C)c(S(=O)(=O)N3CCN(c4ccccn4)CC3)c2C)cc1] | − |
| 4AG | 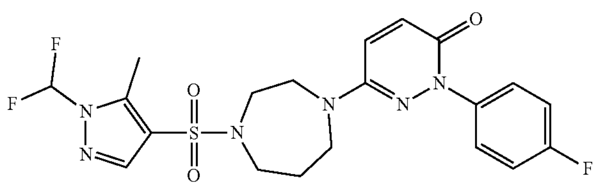 [SMILES: Cc1c(S(=O)(=O)N2CCCN(c3ccc(=O)n(-c4ccc(F)cc4)n3)CC2)cnn1C(F)F] | − |
| 4AH | 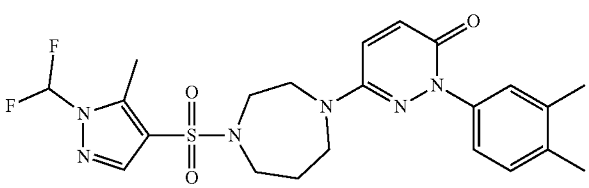 [SMILES: Cc1ccc(-n2nc(N3CCCN(S(=O)(=O)c4cnn(C(F)F)c4C)CC3)ccc2=O)cc1C] | − |
| 4AI | 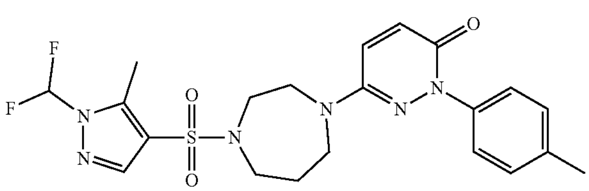 [SMILES: Cc1ccc(-n2nc(N3CCCN(S(=O)(=O)c4cnn(C(F)F)c4C)CC3)ccc2=O)cc1] | − |
| 4AJ | 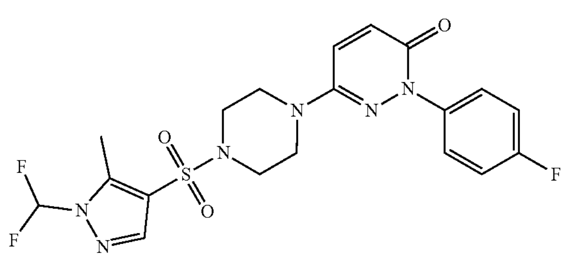 [SMILES: Cc1c(S(=O)(=O)N2CCN(c3ccc(=O)n(-c4ccc(F)cc4)n3)CC2)cnn1C(F)F] | − |
| 4AK | 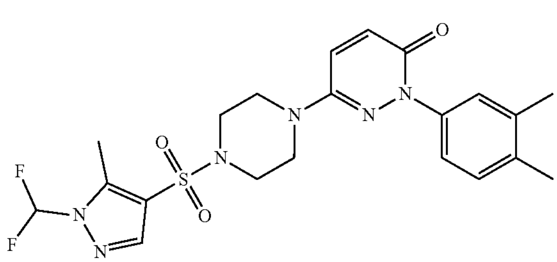 [SMILES: Cc1ccc(-n2nc(N3CCN(S(=O)(=O)c4cnn(C(F)F)c4C)CC3)ccc2=O)cc1C] | − |

TABLE 4-continued

Inhibition of FOXC2-expressing HMLER cells by Formula IV Compounds

| Compound No. | Structures | Activity Score |
|---|---|---|
| 4AL | 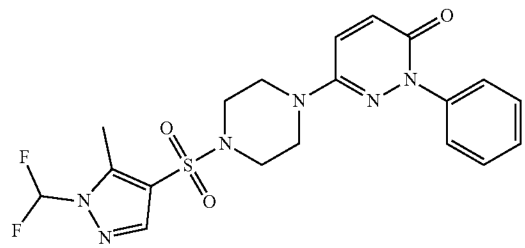 [SMILES: Cc1c(S(=O)(=O)N2CCN(c3ccc(=O)n(-c4ccccc4)n3)CC2)cnn1C(F)F] | – |
| 4AM | 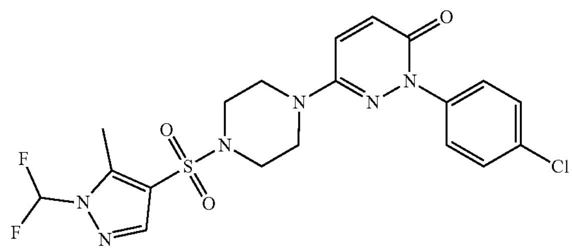 [SMILES: Cc1c(S(=O)(=O)N2CCN(c3ccc(=O)n(-c4ccc(Cl)cc4)n3)CC2)cnn1C(F)F] | – |
| 4AN | 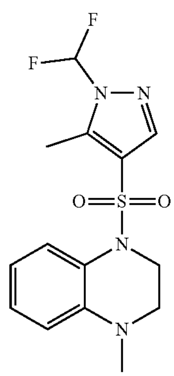 [SMILES: Cc1c(S(=O)(=O)N2CCN(C)c3ccccc32)cnn1C(F)F] | – |
| 4AO | 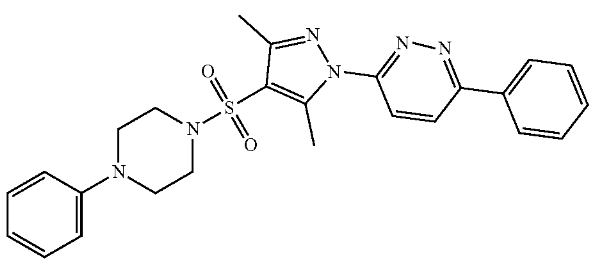 [SMILES: Cc1nn(-c2ccc(-c3ccccc3)nn2)c(C)c1S(=O)(=O)N1CCN(c2ccccc2)CC1] | – |
| 4AP | 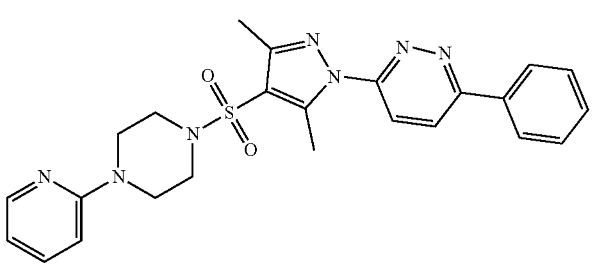 [SMILES: Cc1nn(-c2ccc(-c3ccccc3)nn2)c(C)c1S(=O)(=O)N1CCN(c2ccccn2)CC1] | – |

TABLE 4-continued

Inhibition of FOXC2-expressing HMLER cells by Formula IV Compounds

| Compound No. | Structures | Activity Score |
|---|---|---|
| 4AQ | 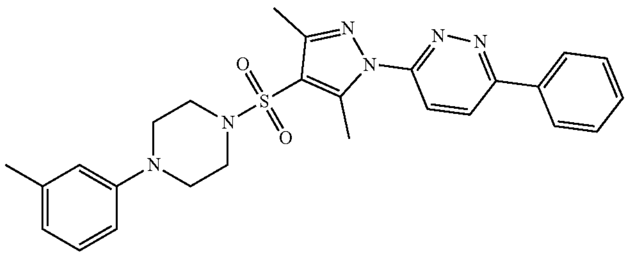 [SMILES: Cc1cccc(N2CCN(S(=O)(=O)c3c(C)nn(-c4ccc(-c5ccccc5)nn4)c3C)CC2)c1] | − |
| 4AR | 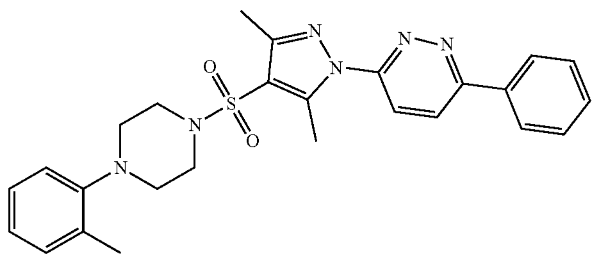 [SMILES: Cc1ccccc1N1CCN(S(=O)(=O)c2c(C)nn(-c3ccc(-c4ccccc4)nn3)c2C)CC1] | − |
| 4AS | 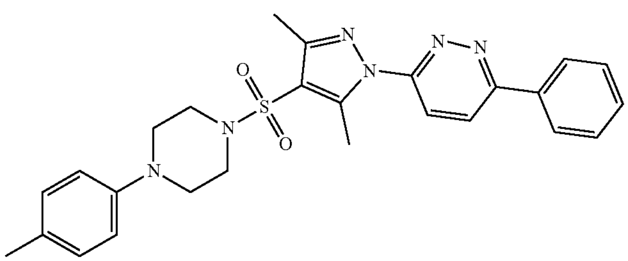 [SMILES: Cc1ccc(N2CCN(S(=O)(=O)c3c(C)nn(-c4ccc(-c5ccccc5)nn4)c3C)CC2)cc1] | − |
| 4AT | 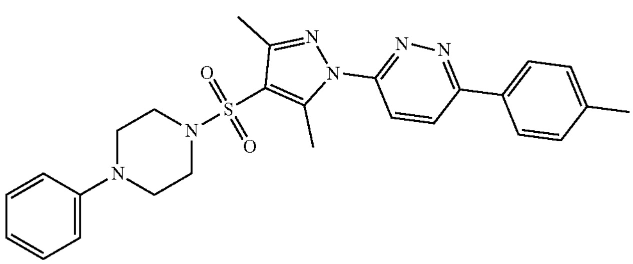 [SMILES: Cc1ccc(-c2ccc(-n3nc(C)c(S(=O)(=O)N4CCN(c5ccccc5)CC4)c3C)nn2)cc1] | − |
| 4AU | 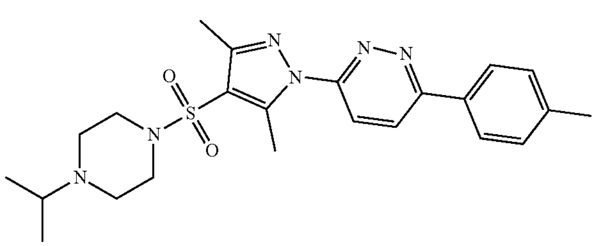 [SMILES: Cc1ccc(-c2ccc(-n3nc(C)c(S(=O)(=O)N4CCN(C(C)C)CC4)c3C)nn2)cc1] | − |

Example 2: Inhibition of Additional Breast Cancer Cell Lines

Compound 1 was chosen for further study because it exhibited selective cytotoxicity (FOXC2-HMLER IC$_{50}$ 234 nM; HMLER IC$_{50}$>20 μM). In particular, Compound 1 was found to inhibit the growth of three additional mesenchymal breast cancer cell lines, SNAIL-HMLE, MDA-MB-231, and SUM159, which express FOXC2 from its endogenous locus.

Example 3: Inhibition of Sarcoma Cell Lines

The anti-proliferative activity of Compound 1 was assessed against a selection of soft tissue sarcomas (STS), which collectively refers to a broad grouping of over 50 subtypes of connective tissue derived cancers for which targeted therapies are lacking (Zambo (2014)). STS tumors arise from tissues of mesenchymal origin and, by default, they express the intermediate filament and mesenchymal marker vimentin VIM irrespective of subtype (G. Lahat, G. et al. *PLoS One* 5 (2010) e10105).

A panel of 6 STS cell lines were evaluated, which cell lines included the histological subtypes of fibrosarcoma (HT 1080, SW684), rhabdomyosarcoma (RD), fibrous histiocytoma (GCT), liposarcoma (SW872), and synovial sarcoma (SW982). All STS cell lines were first confirmed to express vimentin (VIM) at similar levels to FOXC2-HMLER cells by Western blotting analysis.

Western blotting was performed essentially as described previously (M. J. Bollong et al. *ACS Chem. Biol.* 10 (2015) 2193-2198). Cells were collected by brief trypsinization and centrifugation at 500 g for 5 minutes. Cells were lysed by the addition of RIPA buffer with protease and phosphatase inhibitors (Roche). Lysates were incubated on ice for 30 minutes before eliminating insoluble protein content by centrifugation at 12,000 g for 5 minutes at 4° C. Protein concentrations were determined from absorbance values obtained by a Nanodrop instrument. Equal amounts of protein were then mixed with 2× loading buffer (100 mM TRIS-HCl, 1% SDS, 10% glycerol, 0.1% bromophenol blue 10%-mercaptoethanol) and exposed to 95° C. for 5 minutes. Protein was separated by SDS-PAGE using 4-12% Bis-Tris Gels (Invitrogen) and then transferred to PVDF membranes (Invitrogen) using semi-dry transfer. Membranes were blocked for 1 hour at room temperature in 5% non-fat dry milk in TBST (Tris buffered saline with 0.1% Tween 20). Membranes were incubated overnight with primary antibodies in blocking buffer overnight at the dilutions ranging from 1:500 to 1:2000. After 3 washes with TBST, membranes were then exposed to HRP-conjugated secondary antibodies (1:5000 in blocking buffer, Sigma) for one hour followed by one hour of additional washing with TBST. Relative protein content was visualized using film and SuperSignal West Dura Substrate. For VIM degradation blots, 20-60 μg of protein content was loaded per gel lane and the anti-VIM antibody V9 (ab8069) was used to blot for VIM protein content. Phospho-protein blots were performed as above with the exception that primary antibodies were incubated in 5% bovine serum albumin in TBST instead of milk.

Figure 2:
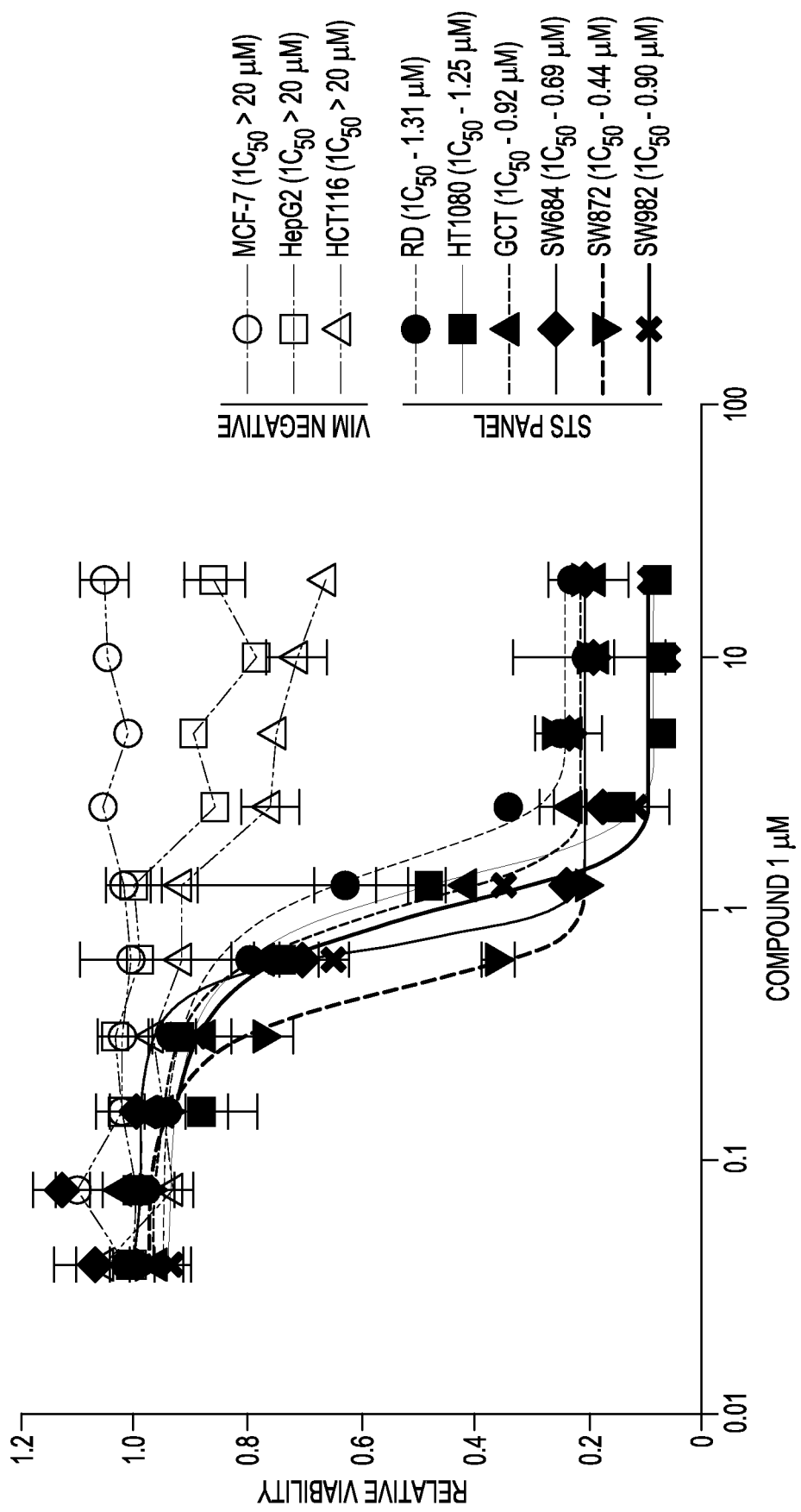
FIG. 2: Relative proliferation measurements of the indicated VIM negative and STS cell lines treated with a concentration response of Compound 1 (n=3, mean and s.e.m.).

Compound 1 was found to effectively inhibit the growth of all cell lines with similar IC$_{50}$ values (0.44-1.31 μM; see FIG. 2). Compound 1 additionally promoted a robust multinucleation phenotype in all STS cell lines over a 24-hour treatment period. In addition, SW872 cells, which is a liposarcoma cell line that displayed a significant degree of basal multinucleation, were most sensitive to Compound 1 treatment (IC$_{50}$ 0.44 μM), indicating that existing mutations promoting genomic instability are able to serve as predictive markers of sensitivity to compounds of this disclosure.

Example 4: Inhibition of Cancer Cell Stemness

Epithelial-mesenchymal transition (EMT) induction endows breast cancer cells with the ability to grow as mammospheres in culture (Mani (2008)). This assay principle is based on studies by Dontu demonstrating that only undifferentiated mammary stem cells can survive in suspension culture whereas differentiated mammary epithelium die as a consequence of anoikis (G. Dontu et al. *Genes Dev.* 17 (2003) 1253-1270).

Figure 3:
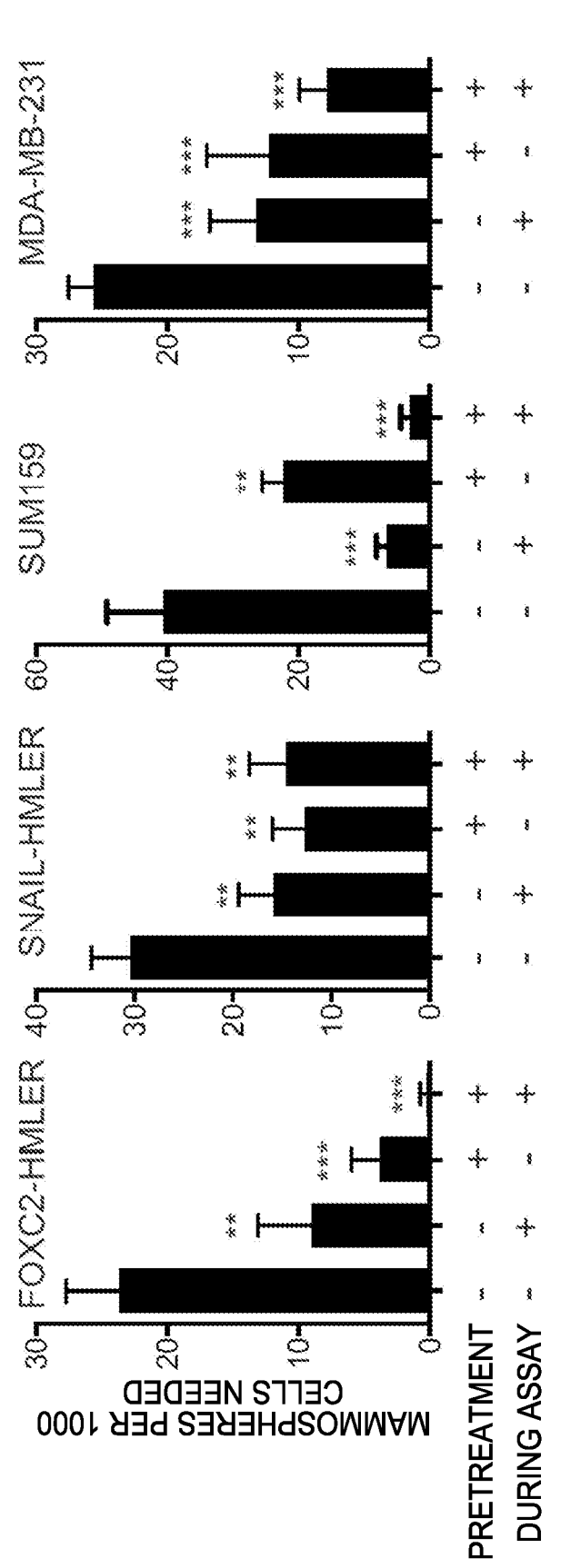
FIG. 3: Quantification of mammospheres from an in vitro mammosphere formation assay with the indicated cell types. Pretreatment indicates a 72-hour treatment with 1 μM Compound 1 before plating in mammosphere formation conditions. The expression "during assay" indicates 1 μM compound treatment during the mammosphere assay (14 days) (n=3, mean and s.d.).

Treatment with Compound 1 inhibited the ability of the FOXC2-expressing lines FOXC2-HMLER, SNAIL-HMLER, SUM159, and MDA-MB-231 cells to form mammospheres in culture (FIG. 3). In addition, pretreating these cell lines 72 h before plating resulted in similar levels of growth inhibition when compared to conditions in which Compound 1 was present throughout the duration of the assay (14 days), further confirming that Compound 1 irreversibly inhibits the stemness potential of these cell types (FIG. 3).

Example 5: Synthesis of Photo-Activatable Affinity Probe (PAP) Molecule

A photo-activatable affinity probe (PAP) molecule was synthesized for target identification experiments.

All non-aqueous reactions were carried out in oven-dried glassware under an atmosphere of nitrogen. All solvents, starting materials and reagents were purchased from commercial vendors and used without further purification. All reagent grade solvents used for chromatography were purchased from Fisher Scientific. A Biotage FLASH column chromatography system was used to purify mixtures and the flash column chromatography silica cartridges were obtained from Biotage. All NMR spectra were recorded on a Varian INOVA-400 spectrometer. Chemical shifts (δ) are reported in parts per million relative to the residual solvent peak, and coupling constants (J) are reported in hertz (Hz). HPLC Gradient conditions: solvent A (0.05% TFA in water) and solvent B (0.05% TFA in Acetonitrile): 0-2 min 95% A, 2-12 min 5-95% B (linear gradient), 12-15 min 100% B. Detection by UV-Vis (220-400 nm).

3-chloro-2-nitrobenzoyl chloride

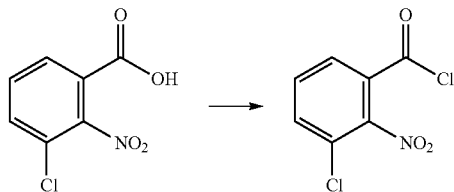 [SMILES: O=C(O)c1cccc(Cl)c1[N+](=O)[O-] ; O=C(Cl)c1cccc(Cl)c1[N+](=O)[O-]]

To a solution of 2-nitro-3-chlorobenzoic acid (10.08 g, 50 mmol) in dichloromethane (67 mL) was added thionyl chloride (18.2 mL, 250 mmol) followed by DMF (3 drops). The reaction was refluxed 2 hours and evaporated in vacuo to give the acid chloride (10.34 g, 94%). 1H-NMR (400 MHz; DMSO-d6): δ 8.01-7.97 (m, 2H), 7.71 (t, J=8.0 Hz, 1H).

1-(3-chloro-2-nitrophenyl)ethan-1-one

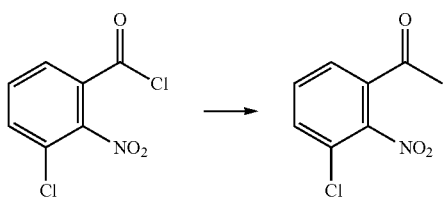

To a suspension of magnesium (10 g, 0.41 mol) in dry THF (750 mL) at 50° C. was added ethanol (40.1 mL) and carbon tetrachloride (1 mL). After 30 min. a solution of diethyl malonate (62.5 mL, 0.41 mol) in ethanol (28 mL, 0.69 mol) was added and the reaction was allowed to stir at 60° C. for 2 hrs. Quench with 10% sulfuric acid (250 mL). Separate and evaporate the organic layer to give a yellow oil. To the oil was added acetic acid (365 mL), sulfuric acid (49 mL) and water (248 mL). This mixture was refluxed 10 hours and the product was extracted with ethyl acetate. The combined extracts were washed with water followed by brine and dried over sodium sulfate and evaporated in vacuo to give the product 65 g, 79%). 1H-NMR (400 MHz; CDCl3): δ 7.76 (d, J=7.8 Hz, 1H), 7.70 (d, J=8.1 Hz, 1H), 7.56 (t, J=8.0 Hz, 1H), 2.61 (s, 3H).

1-(2-amino-3-chlorophenyl)ethan-1-one

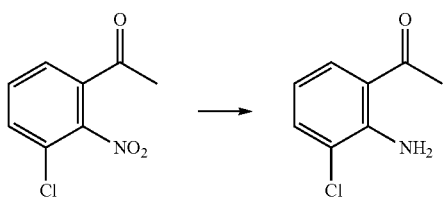

To a solution of 1-(3-chloro-2-nitrophenyl)ethan-1-one (65 g, 0.33 mol) in glacial acetic acid (500 mL) was added iron powder (55 g, 0.98 mol). Shake the slurry until it thick. Use cooling to prevent a reflux. Let the mixture sit for 1 hr at 80° C. shaking ever hour to make sure it is mixed. Cool and quench with 10% sodium hydroxide. Extract product by shaking with ethyl acetate and then separating the emulsion by centrifugation followed by decanting the organic layer. Repeat 3 times. Filter through celite, dry over sodium sulfate and evaporate in vacuo to give the aniline (44.1 g, 80%). 1H-NMR (400 MHz; CDCl3): δ 7.76 (d, J=7.8 Hz, 1H), 7.70 (d, J=8.1 Hz, 1H), 7.56 (t, J=8.0 Hz, 1H), 2.61 (s, 3H).

8-chlorocinnolin-4-ol

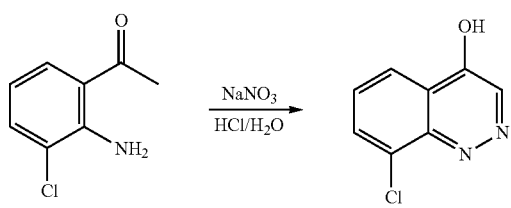

To a suspension of 1-(2-amino-3-chlorophenyl)ethan-1-one (5 g, 29.5 mmol) in water (29 mL) at 0° C. was added conc. HCl (205 mL). A solution of sodium nitrite (2.05 g, 29.7 mmol) in water (7.5 mL) was added dropwise. The reaction was stirred for 1 hr. at 0° C. then heated at 65° C. for 4 hr. After cooling, the product was collected by filtration. The product was triturated with acetone and recrystallized from boiling 6M HCl to give the product as pink needles (2.81 g, 15.7 mmol). 1H-NMR (400 MHz; CDCl3): δ 10.32 (s, 1H), 8.19 (dd, J=8.2, 0.6 Hz, 1H), 7.89 (s, 1H), 7.77 (dd, J=7.7, 1.3 Hz, 1H), 7.35 (t, J=7.9 Hz, 1H).

4-bromo-8-chlorocinnoline

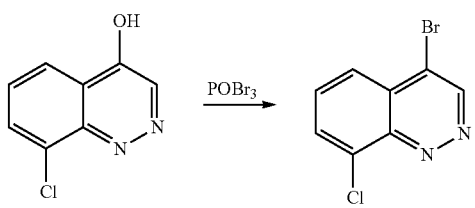

A bottle of phosphorus oxybromide (25 g, 87.2 mmol) was melted with a heat gun and poured into chloroform (150 mL). To this solution was added 8-chlorocinnolin-4-ol (2.8 g, 15.5 mmol) and was stirred until a thick slurry was obtained (~20 min). The reaction was refluxed 2 hr. and then basified with 10% sodium carbonate. The mixture was filtered through celite and extracted with chloroform. The combined organic layers were dried over sodium sulfate and evaporated to give the product (3.5 g, 92%) as a green-brown solid. 1H-NMR (400 MHz; DMSO-d6): δ 9.81 (s, 1H), 8.23 (d, J=7.5 Hz, 1H), 8.11 (d, J=8.5 Hz, 1H), 7.98 (t, J=8.0 Hz, 1H).

4-chloro-8-chlorocinnoline

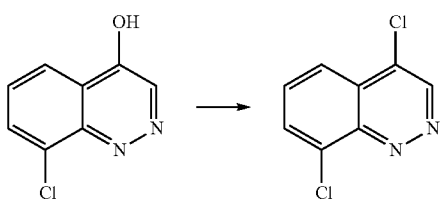 [SMILES: Oc1cnnc2c(Cl)cccc12 ; Clc1cnnc2c(Cl)cccc12]

To a flask containing 8-chlorocinnolin-4-ol (4.67 g, 25.9 mmol) was added thionyl chloride (100 mL) the mixture was refluxed for 2 hr. and evaporated in vacuo to give the product (5.15 g, 100%). 1H-NMR (400 MHz, CDCl3): δ 9.47 (s, 1H), 8.16 (d, J=8.4 Hz, 1H), 8.03 (d, J=7.2 Hz, 1H), 7.81 (t, J=8.0 Hz, 1H).

193

8-chloro-4-(4-(3-chlorophenyl)piperazin-1-yl)cinnoline

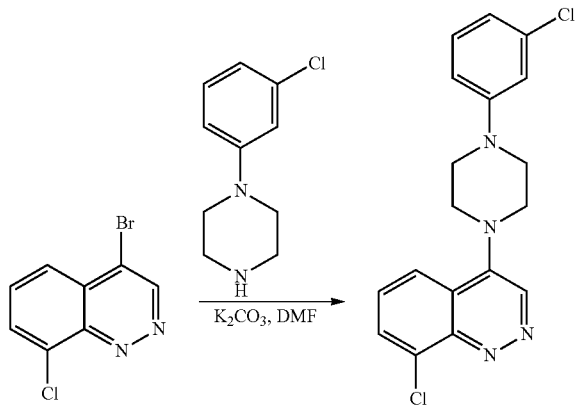

To a solution of 4-bromo-8-chlorocinnoline (25 mg, 0.10 mmol) and 1-(3-chlorophenyl)piperazine HCl (23.9 g, 0.10 mmol) in dimethylformamide (1 mL) was added potassium carbonate (42.6 mg, 0.31 mmol). The reaction was stirred at 60° C. overnight. Water was added to the mixture to precipitate the product, which was collected by filtration or centrifugation. The product was washed with methanol and dried in vacuo to give the product (28 mg, 75%). Mass calculated for $C_{18}H_{16}Cl_2N_4$ 358.0751; Mass observed by HR-MS (ESI+) 359.0825 (M+H). 1H-NMR (400 MHz; CDCl3): δ 9.07 (s, 1H), 7.93 (dd, J=8.5, 1.0 Hz, 1H), 7.89 (dd, J=7.4, 1.0 Hz, 1H), 7.60 (dd, J=8.4, 7.5 Hz, 1H), 7.23 (d, J=8.1 Hz, 1H), 6.97 (t, J=2.1 Hz, 1H), 6.92-6.86 (m, 2H), 3.54 (dd, J=6.8, 3.1 Hz, 4H), 3.49 (dd, J=6.8, 2.9 Hz, 4H).

2-(2-(2-aminoethoxy)ethoxy)ethan-1-ol

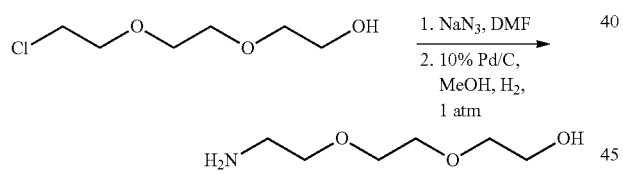

A solution of 2-(2-(2-chloroethoxy)ethoxy)ethan-1-ol (12.5 g, 74.1 mmol) and sodium azide (7.25 g, 111.5 mmol) in DMF (125 mL) was allowed to stir at 100° C. overnight. The mixture was filtered and evaporated to give 2-(2-(2-azidoethoxy)ethoxy)ethan-1-ol. A solution of the crude material and 10% Pd/C (1.12 g) in methanol (100 mL) was hydrogenated (1 atm) overnight. The mixture was filtered, evaporated and purified via flash chromatography (0-20% MeOH/DCM) to give the amine (3.53 g, 32% over 2 steps) 1H-NMR (400 MHz; CDCl3): δ 3.75-3.71 (dd, 2H), 3.69-3.64 (m, 2H), 3.64-3.61 (m, 2H), 3.59-3.53 (m, 2H), 3.48-3.45 (m, 2H), 2.88 (t, J=5.1 Hz, 2H).

benzyl (2-(2-(2-hydroxyethoxy)ethoxy)ethyl)carbamate

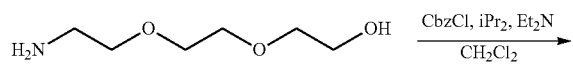

194

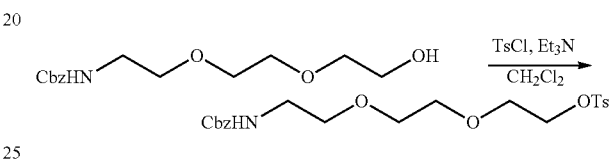

To a solution of 2-(2-(2-aminoethoxy)ethoxy)ethan-1-ol (3.53 g, 23.7 mmol) and diisopropylethylamine (8.2 mL, 47.3 mmol) in dichloromethane (75 mL) at 0° C. was added benzyl chloroformate (5 mL, 35.5). The solution was allowed warm to room temperature and stirred for 2 hours. The mixture was evaporated and purified by flash chromatography (20-100% EtOAc/hexanes) to give the benzyl carbamate (3 g, 45%). 1H-NMR (400 MHz; CDCl3): δ 7.37-7.31 (m, 5H), 5.37 (s, 1H), 5.14-5.09 (s, 2H), 3.72-3.71 (m, 2H), 3.64-3.59 (m, 8H), 3.40 (q, J=5.2 Hz, 2H).

3-oxo-1-phenyl-2,7,10-trioxa-4-azadodecan-12-yl-4-methylbenzenesulfonate

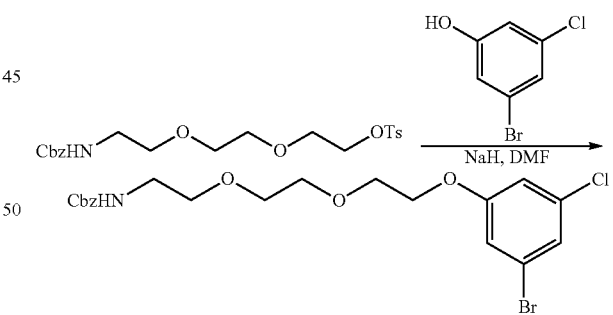

To a solution of benzyl (2-(2-(2-hydroxyethoxy)ethoxy)ethyl)carbamate (3 g, 10.6 mmol) and triethylamine (3 mL, 2 eq.) in dichloromethane (50 mL) was added tosyl chloride (2.4 g, 12.7 mmol). The solution was allowed to stir overnight, was evaporated and purified by flash chromatography (20-100% EtOAc/hexanes) to give the tosylate (2.85 g, 62%). 1H-NMR (400 MHz; CDCl3): δ 7.80 (s, 1H), 7.78 (s, 1H), 7.36 (m, 5H), 7.33 (s, 1H), 7.31 (s, 1H), 5.20 (s, 1H), 5.09 (s, 2H), 4.15 (t, J=4.7 Hz, 2H), 3.67 (t, J=4.8 Hz, 2H), 3.56 (d, J=2.3 Hz, 2H), 3.52 (t, J=5.0 Hz, 2H), 3.37 (q, J=5.3 Hz, 2H), 2.43 (s, 3H).

benzyl (2-(2-(2-(3-bromo-5-chlorophenoxy)ethoxy)ethoxy)ethyl)carbamate

To a solution of 3-bromo-5-chlorophenol (2.85 g, 6.5 mmol) in DMF (30 mL) at 0° C. was added sodium hydride (348 mg, 13 mmol). After stirring for 10 minutes 3-oxo-1-phenyl-2,7,10-trioxa-4-azadodecan-12-yl 4-methylbenzenesulfonate (3.01 g, 6.5 mmol) was added. The mixture was allowed to stir overnight at room temperature. The mixture was evaporated in vacuo and purified by flash chromatography to give the product (1.67 g, 84% brsm) 1H-NMR (400 MHz; CDCl3): δ 7.35-7.30 (m, 4H), 7.10 (s, 1H), 6.96 (s, 1H), 6.84 (s, 1H), 5.25 (s, 1H), 5.09 (s, 2H), 4.07 (t, J=4.4 Hz, 2H), 3.81 (t, J=4.7 Hz, 2H), 3.69-3.66 (m, 2H), 3.64-3.62 (m, 2H), 3.57 (t, J=5.1 Hz, 2H), 3.40 (q, J=5.0 Hz, 2H).

tert-butyl 4-(3-(2-(2-(2-aminoethoxy)ethoxy)ethoxy)-5-chlorophenyl)piperazine-1-carboxylate

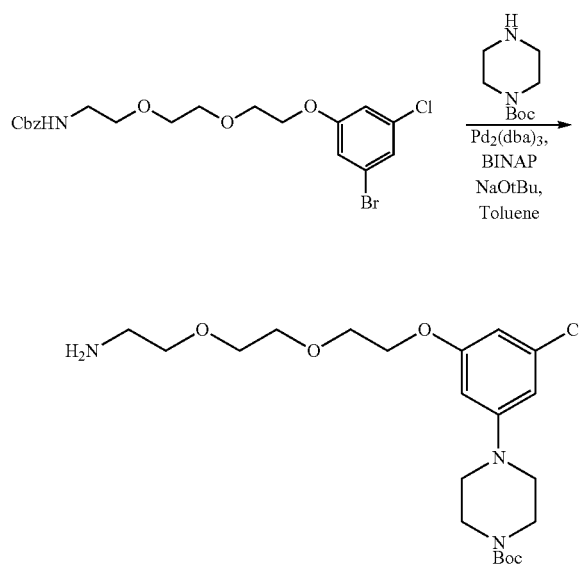

A solution of benzyl (2-(2-(2-(3-bromo-5-chlorophenoxy)ethoxy)ethoxy)ethyl)carbamate (1.67 g, 3.5 mmol), tert-butyl piperazine-1-carboxylate (658 mg, 1 eq.), Tris(dibenzylideneacetone)dipalladium (97 mg, 3 mol %), Bis(diphenylphosphino)-1,1'-binaphthalene (198 mg, 9 mol %), sodium tert-butoxide (679 mg, 7.1 mmol) in toluene (30 mL) was allowed to stir at 90° C. overnight. The mixture was purified by flash chromatography (400/o EtOAc/hexanes then 10% MeOH/DCM) to give the product (1.31 g, 84%). 1H-NMR (400 MHz; CDCl3): δ 6.48 (s, 1H), 6.40 (s, 1H), 6.34 (s, 1H), 4.08 (t, J=4.7 Hz, 2H), 3.81 (t, J=4.8 Hz, 2H), 3.70-3.68 (m, 2H), 3.65-3.62 (m, 2H), 3.56 (t, J=5.1 Hz, 2H), 3.52 (t, J=5.2 Hz, 2H), 3.42 (t, J=5.1 Hz, 2H), 3.10 (t, J=5.0 Hz, 2H), 2.92 (t, J=5.3 Hz, 2H), 2.83 (t, J=5.0 Hz, 2H), 2.14 (s, 2H), 1.44 (s, 9H).

benzyl tert-butyl 4-(3-chloro-5-((3-oxo-1-phenyl-2,7,10-trioxa-4-azadodecan-12-yl)oxy)phenyl)piperazine-1-carboxylate

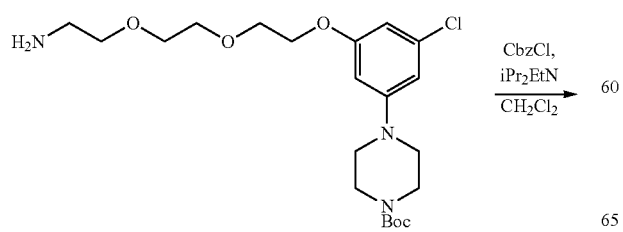

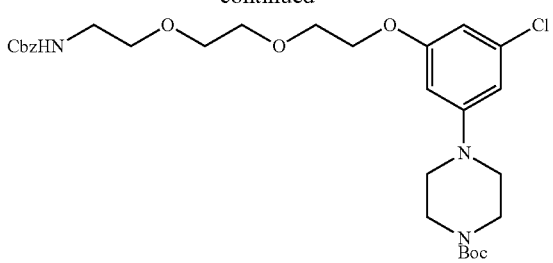

To a solution of tert-butyl 4-(3-(2-(2-(2-aminoethoxy)ethoxy)ethoxy)-5-chlorophenyl)piperazine-1-carboxylate (1.31 g crude, 3 mmol) and diisopropylethylamine (1 mL, 5.9 mmol) in dichloromethane (29 mL) at 0° C. was added benzyl chloroformate (0.62 mL, 4.4 mmol). The solution was allowed warm to room temperature and stirred for 2 hours. The mixture was evaporated and purified by flash chromatography to give the benzyl carbamate (1.0 g, 59%). 1H-NMR (400 MHz; CDCl3): δ 7.37-7.32 (m, 5H), 6.50 (s, 1H), 6.40 (s, 1H), 6.33 (s, 1H), 5.26 (s, 1H), 5.09 (s, 2H), 4.07 (t, J=4.3 Hz, 2H), 3.81 (t, 1=4.8 Hz, 2H), 3.70-3.67 (m, 2H), 3.65-3.62 (m, 2H), 3.59-3.51 (m, 4H), 3.39 (q, J=5.5 Hz, 2H), 3.11 (t, J=5.0 Hz, 3H), 1.48 (s, 9H).

benzyl (2-(2-(2-(3-chloro-5-(piperazin-1-yl)phenoxy)ethoxy)ethoxy)ethyl)carbamate To a solution of tert-butyl 4-(3-chloro-5-((3-oxo-1-phenyl-2,7,10-trioxa-4-azadodecan-12-yl)oxy)phenyl)piperazine-1-carboxylate (1 g, 1.7 mmol) at 0° C. in dichloromethane (25 mL) was added trifluoroacetic acid (5 mL). The mixture was stirred for an hour and was evaporated to give the amine (1.39 g) as the TFA salt and was taken on crude.

benzyl (2-(2-(2-(3-chloro-5-(4-(8-chlorocinnolin-4-yl)piperazin-1-yl)phenoxy)ethoxy)ethoxy)ethyl)carbamate

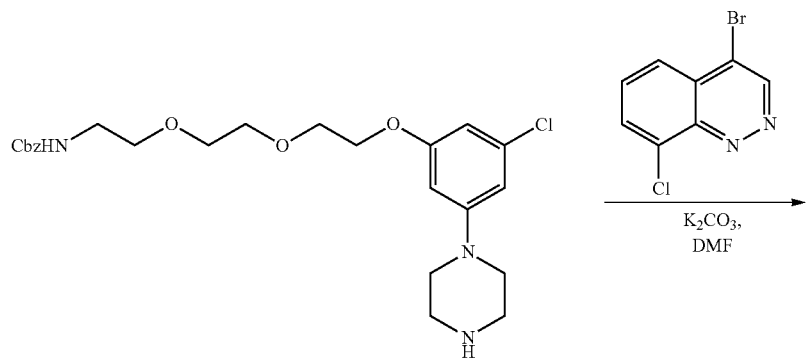

To a solution of crude (2-(2-(2-(3-chloro-5-(piperazin-1-yl)phenoxy)ethoxy)ethoxy)ethyl)carbamate (1.08 g, 2.3 mmol) in DMF (20 mL) was added potassium carbonate (1.26 g, 6.8 mmol) and 4-bromo-8-chlorocinnoline (666 mg, 2.7 mmol). The mixture was allowed to stir at 60° C. overnight and was then filtered and evaporated in vacuo at 60° C. The crude material was purified via flash chromatography (50-100% EtOAc/Hexanes) to give the product (561 mg, 38%) as a white solid. 1H-NMR (400 MHz; CDCl3): δ 9.02 (s, 1H), 7.88 (dd, J=12.1, 8.0 Hz, 2H), 7.57 (t, J=7.9 Hz, 1H), 7.32-7.27 (m, 5H), 6.57 (s, 1H), 6.45 (s, 1H), 6.41 (s, 1H), 5.27 (s, 1H), 5.07 (s, 2H), 4.08 (t, J=4.8 Hz, 2H), 3.81 (t, J=4.7 Hz, 2H), 3.68 (dd, J=6.0, 3.1 Hz, 2H), 3.63 (dd, J=5.7, 3.1 Hz, 2H), 3.56 (t, J=5.0 Hz, 2H), 3.50-3.46 (m, 4H), 3.44-3.41 (m, 4H), 3.39-3.36 (m, 2H).

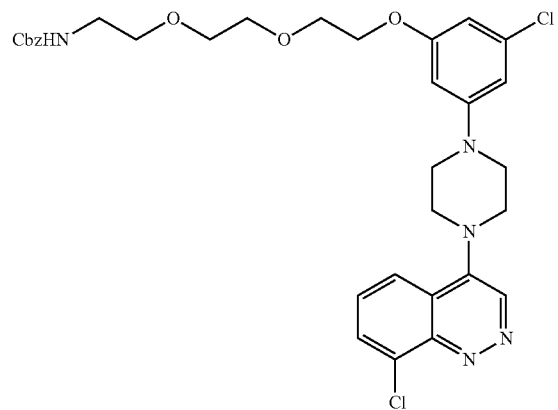

2-(2-(2-(3-chloro-5-(4-(8-chlorocinnolin-4-yl)piperazin-1-yl)phenoxy)ethoxy)ethoxy)ethan-1-amine

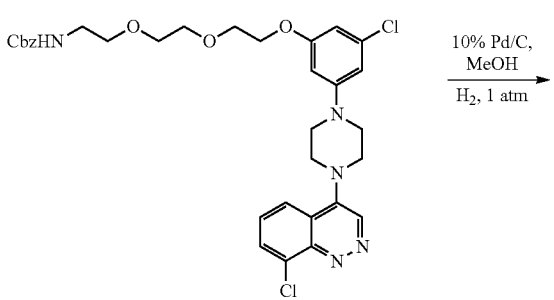

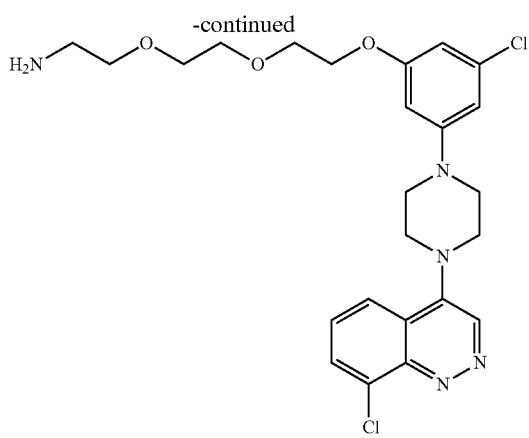

To a solution of benzyl (2-(2-(2-(3-chloro-5-(4-(8-chlorocinnolin-4-yl)piperazin-1-yl)phenoxy)ethoxy)ethoxy)ethyl) carbamate (80 mg, 0.12 mmol) in MeOH (10 mL) was added 10% Pd/C (40 mg). The mixture was allowed to stir under hydrogen at 1 atm until complete by TLC (~30 min). The mixture was filtered an then evaporated and purified by HPLC to give the product (58 mg, 92%). Mass calculated for $C_{24}H_{29}Cl_2N_5O_3$ 505.1647; Mass observed by HR-MS (ESI+) 506.1721 (M+H). 1H-NMR (400 MHz; CD3OD): δ 9.03 (s, 1H), 8.08 (d, J=8.5 Hz, 1H), 7.96 (d, J=7.5 Hz, 1H), 7.68 (t, J=8.0 Hz, 1H), 6.64 (s, 1H), 6.51 (s, 1H), 6.47 (s, 1H), 4.11 (t, =4.6 Hz, 2H), 3.82 (t, J=4.5 Hz, 2H), 3.70 (dd, J=5.6, 3.3 Hz, 2H), 3.65-3.63 (m, 2H), 3.62-3.60 (m, 4H), 3.48-3.46 (m, 4H), 2.80 (t, J=5.3 Hz, 2H).

N—((S)-1-(3-chloro-5-(4-(8-chlorocinnolin-4-yl)piperazin-1-yl)phenoxy)-11-(2-(3-methyl-3H-diazirin-3-yl)ethyl)-10,13-dioxo-3,6,16,19-tetraoxa-9,12-diazahenicosan-21-yl)-5-((3aS,4S,6aR)-2-oxohexahydro-1H-thieno[3,4-d]imidazol-4-yl)pentanamide (1-PAP)

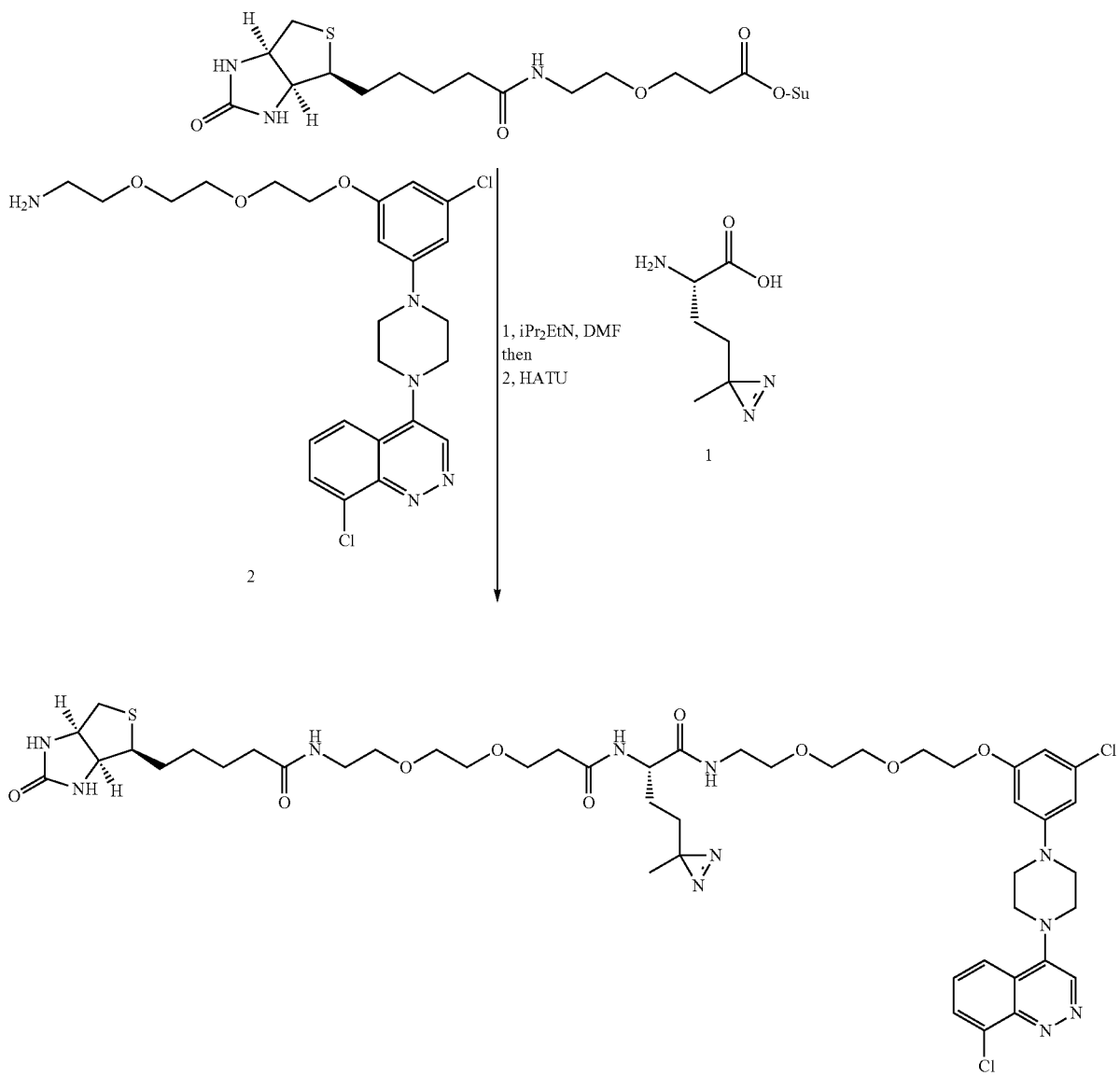

To a solution of biotin-PEG2-NHS (19.8 mg, 0.043 mmol) in DMF (2 mL) was added (S)-2-amino-4-(3-methyl-3H-diazirin-3-yl)butanoic acid (1 (photo-methionine), 6.2 mg, 0.039). The mixture was allowed to stir for 1 hour in a dark foil wrapped vial (or until complete by HPLC) and 2-(2-(2-(3-chloro-5-(4-(8-chlorocinnolin-4-yl)piperazin-1-yl)phenoxy)ethoxy)ethoxy)ethan-1-amine (2, 20 mg, 0.039 mmol) and HATU (22.5 mg, 0.059 mmol) were added. The mixture was allowed to stir overnight and was purified by HPLC to give the product (5 mg, 12%). Mass calculated for $C_{47}H_{65}Cl_2N_{11}O_9S$ 1029.4064, Mass observed by HR-MS (ESI+) 1030.4139 (M+H). 1H-NMR (400 MHz; DMSO-d6): δ 9.11 (s, 1H), 8.04 (d, J=8.8 Hz, 1H), 8.02 (d, J=7.4 Hz, 1H), 7.94 (d, J=8.3 Hz, 1H), 7.90 (t, J=5.8 Hz, 1H), 7.79 (t, J=5.7 Hz, 1H), 7.70 (t, J=8.1 Hz, 1H), 6.63 (s, 1H), 6.49 (s, 1H), 6.45 (s, 1H), 6.38 (s, 1H), 6.32 (s, 1H), 4.28 (t, J=3.6 Hz, 1H), 4.19-4.14 (m, 1H), 4.11-4.06 (m, 3H), 3.70 (t, J=4.3 Hz, 2H), 3.61-3.11 (m, 27H), 3.08-3.02 (m, 1H), 2.79 (dd, J=12.6, 5.0 Hz, 1H), 2.03 (t, J=7.2 Hz, 2H), 1.50-1.40 (m, 2H), 1.25-1.21 (m, 6H), 0.93 (s, 3H), 0.83 (t, J=6.1 Hz, 2H).

Example 6: Binding to Vimentin

To identify the relevant cellular target of Compound 1, we incubated live FOXC2-HMLER cells with 2.5 µM 1-PAP, as prepared in Example 5, for 15 minutes and subjected these cells to UV irradiation. A sample containing both 1-PAP and a 20-fold molar excess of free Compound 1 was used to distinguish specific labeling events. Surprisingly, ammonium sulfate fractionation of the labeled lysate followed by Western blotting for biotin revealed an abundant band in the 20% fraction whose intensity was dramatically increased in the presence of Compound 1 competition.

We then showed that 1-PAP labels recombinant full length VIM in vitro. VIM consists of a long rod domain, which forms a coiled coil in the presence of other VIM molecules, as well as head and tail domains. To identify which portion of the protein was the relevant site of 1-PAP labeling, we expressed these domains as GST fusion proteins. In vitro labeling experiments indicated that 1-PAP binds specifically and potently to the rod domain of VIM. VIM is one of four type III intermediate filament proteins, whose members additionally include Peripherin, glial fibrillary acidic protein (GFAP), and Desmin, which share 59%, 61%, and 62% sequence similarity to VIM respectively (SIM alignment, ExPASy) (E. Fuchs et al., Annu. Rev. Biochem. 63 (1994) 345-382). In vitro labeling experiments with recombinant preparations of these proteins revealed 1-PAP labeled VIM exclusively, indicating the specificity of this interaction relative to closely related filamentous proteins.

Withaferin A (WIF-A), a steroidal lactone natural product derived from *Withania somnifera*, was previously reported as a potent inhibitor of cancer growth (G. Lahat et al., *PLoS One* 5 (2010) e10105; B. Grin, *PLoS One* 7 (2012) e39065). Early mechanism of action studies suggested that WIF-A inhibits the activities of VIM through covalent modification of the single cysteine residue present on the rod domain of the protein (P. Bargagna-Mohan, et al., *Chem. Biol.* 14 (2007) 623-634). WIF-A treatment was found to be selectively cytotoxic to FOXC2-HMLER cells with an ~10-fold cytotoxic index relative to control cells, confirming the notion that targeting VIM is lethal to mesenchymally transformed cells. We reasoned that toxicity to both cell lines at doses above 200 nM might be explained by WIF-A's reported off target inhibitory activities which include the covalent modification of GFAP, β-Tubulin, NF-κB, and Sp1 (P. Bargagna-Mohan et al., *J. Biol. Chem.* 285 (2010) 7657-7669; M. L. Antony et al., *J. Biol. Chem.* 289 (2014) 1852-1865; K. Heyninck et al., *Biochem. Pharmacol.* 91 (2014) 501-509). Although these off target interactions indicate WIF-A is unsuitable as a selective chemical probe of VIM, we nevertheless used it as a positive control in certain assays for which WIF-A has been previously reported to inhibit VIM function.

WIF-A is thought to induce cell death of VIM-expressing cancer cells, at least in part, by inducing filamentous network collapse and degradation of VIM (B. Grin (2012) and G. Lahat (2010, supra). To monitor the assembly status of the VIM filamentous architecture, we performed immunofluorescent analyses of human umbilical endothelial cells (HUVECs) that were treated with Compound 1 and WIF-A, which have been shown to display a high elaborated VIM architecture sensitive to WIF-A treatment (P. Bargagna (2007), supra).

These studies revealed that one-hour treatment with Compound 1 and WIF-A promoted the destruction of fine VIM-containing filamentous structures and the contraction of the VIM apparatus relative to the boundary of the cell. Additionally, WIF-A and Compound 1 induced rapid morphological changes in the appearance of FOXC2-HMLER cells as determined by immunofluorescent analysis for VIM staining, a result consistent with the idea that the previously described morphological changes are due to VIM reorganization.

Further, treatment of FOXC2-HMLER cells with Compound 1 dramatically reduced the appearance of dibromobimane-crosslinked dimeric VIM protein content, as shown by Western blotting, by procedures previously used to monitor the filamentous status of VIM in cells and in solution (D. Perez-Sala, et al. *Nat. Commun.* 6 (2015) 7287. Additionally, treatment of FOXC2-HMLER cells with Compound 1 or WIF-A induced the dose-dependent accumulation of lower molecular weight VIM degradation products as visualized by Western blotting.

WIF-A has also been reported to induce the degradation of VIM protein by a ubiquitin proteasome mediated mechanism (P. Bargagna-Mohan (2007), supra). Analyzing the protein content of FLAG-immunoprecipitated VIM from HEK293T cells, we observed a clear accumulation of high molecular weight ubiquitinated VIM species. This result is consistent with the idea that both compounds trigger the degradation of VIM through a ubiquitin mediated mechanism.

Example 7: Modulation of Phosphorylation State of Vimentin

Figure 4:
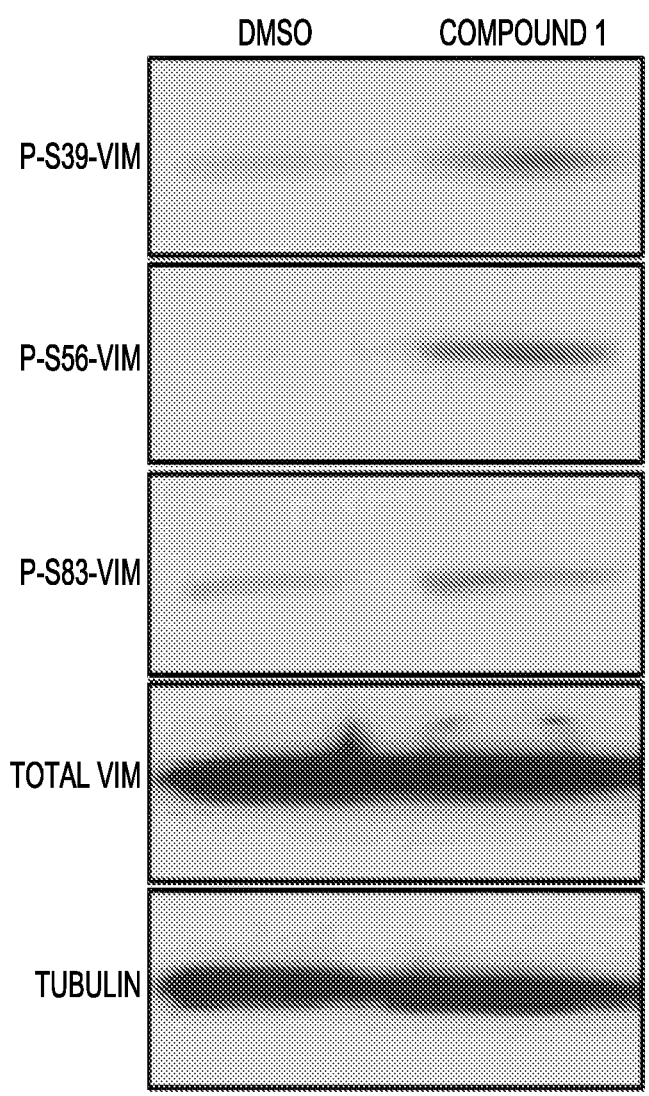
FIG. 4: Western blotting analysis of phosphorylated VIM protein content from FOXC2-HMLER cells treated for 24 hours with Compound 1 (500 nM).

We performed Western blotting analysis of FOXC2-HMLER cells treated for 24 hours with Compound 1 with commercially available antibodies targeting specific phosphorylated VIM species (P-S39, P-S56, P-S83). Treatment by Compound 1 induced a modest increase in P-S39- and P-S83-VIM protein content but led to a marked increase in the steady state levels of P-S56-VIM (FIG. 4).

Figure 5:
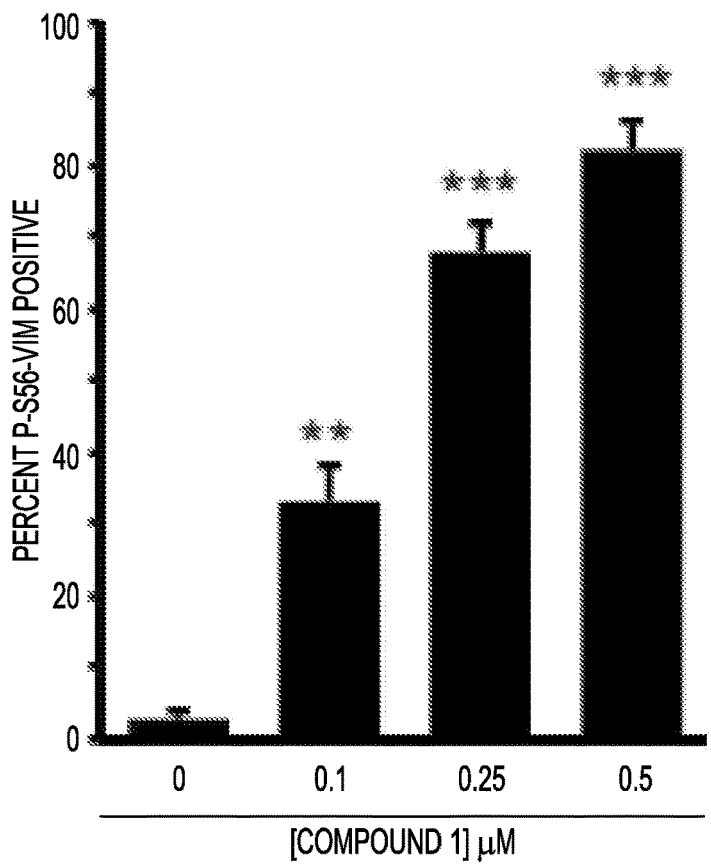
FIG. 5: Quantification of immunofluorescent staining for P-S56-VIM from FOXC2-HMLER cells treated with the indicated doses of Compound 1 (n=3, mean and s.d.; P<0.005, *P<0.0005; t-test)
Figure 6:
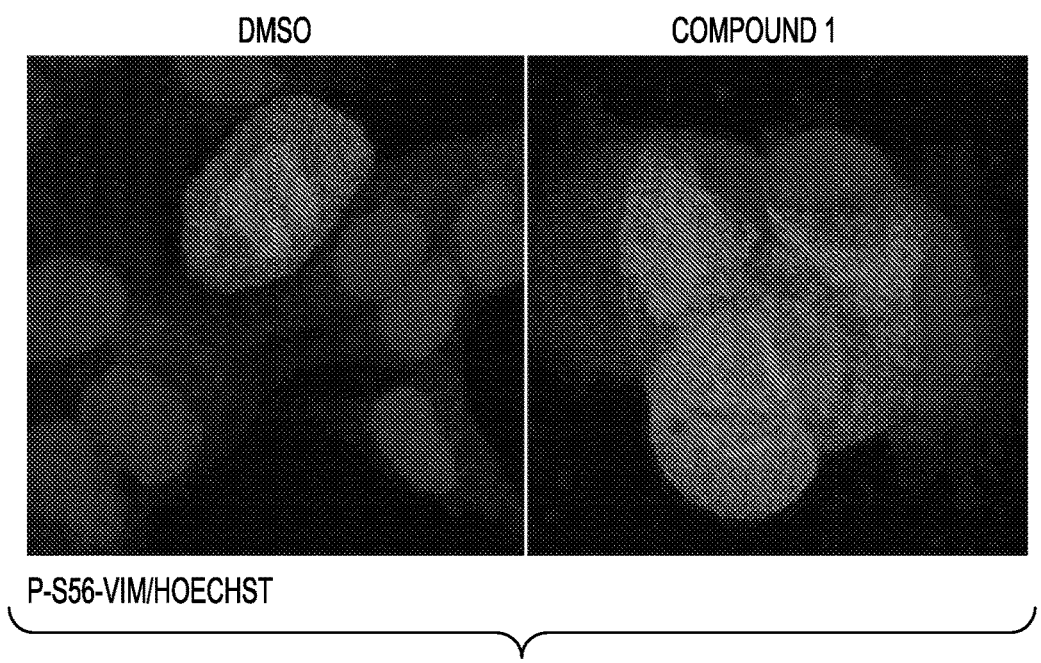
FIG. 6: Representative images of immunofluorescent staining for P-S56-VIM from FOXC2-HMLER cells treated with Compound 1.

Immunofluorescent staining experiments for P-S56-VIM corroborated this observation, with Compound 1 treatment resulting in a concentration dependent increase in P-S56-VIM positive FOXC2-HMLER cells (FIG. 5). In contrast, only a small fraction of cells undergoing mitosis stained positive for P-S56-VIM in DMSO-treated controls, consistent with previous reports identifying phosphorylation at S56 as a modification catalyzed by cyclin dependent kinase 1 (CDK1; FIG. 6) (T. Yamaguchi, T. et al., *J. Cell Biol.* 171 (2005) 431-436.

To determine if this increase in P-S56-VIM protein content might be responsible for FiVe1's ability to induce multinucleation, we performed transient overexpression experiments with vectors encoding FLAG-tagged wild type VIM (VIM-wt-FLAG) or a phospho-mimetic mutant of VIM at S56 (VIM-S56E-FLAG) in FOXC2-HMLER and HEK293T cells. 72-hour expression of the VIM-S56E-FLAG transgene was found to induce multinucleation in both cell lines. We additionally overexpressed these transgenes by stable lentiviral delivery in FOXC2-HMLER cells. Whereas VIM-wt-FLAG expressing cells grew similarly to dTomato-expressing control cells over 7 days, VIM-S56E-FLAG cells were found to be replication incompetent over this period. Together, these results suggest that a specific, sustained phosphorylation modification on VIM is sufficient to recapitulate the activity of Compound 1.

Because Compound 1 induces a hyper-phosphorylated VIM phenotype, we sought to determine if Compound 1's engagement of VIM might interfere at an alternative stage of mitosis. We therefore performed time course confocal imaging studies of Compound 1 treated FOXC2-HMLER cells after their release from thymidine blocking-based cell cycle synchronization. While Compound 1 treated cells were found to condense their chromosomes during anaphase normally, Compound 1 treated cells exhibited a number of altered phenotypes during metaphase.

Figure 7:
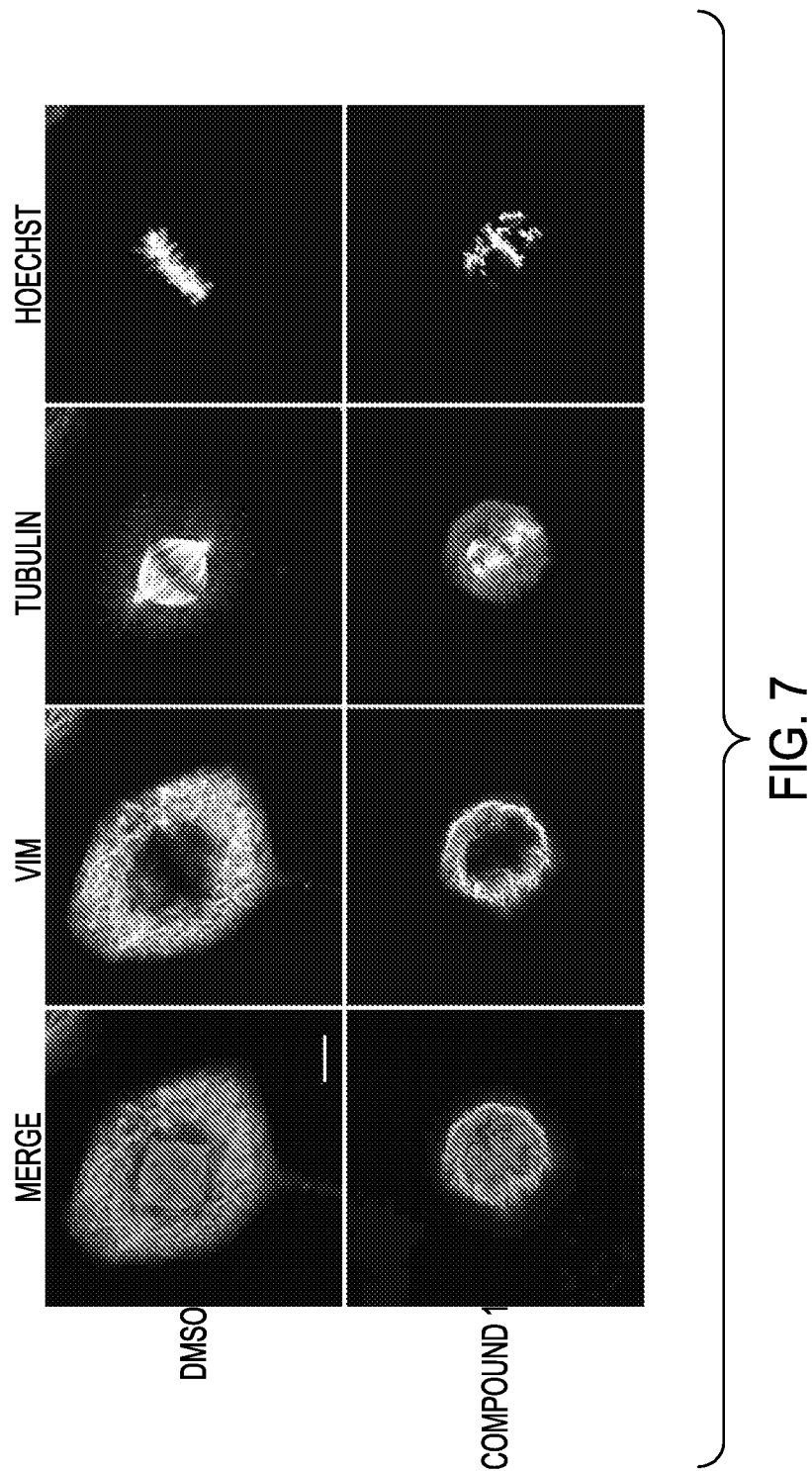
FIG. 7: Representative confocal images of thymidine synced FOXC2-HMLER cells at metaphase immunostained for VIM and β-tubulin (TUB).

Compound 1 treatment resulted in a collapsed VIM filamentous structure, which appeared more closely associated to mitotic spindle poles when compared to DMSO treated controls (FIG. 7). Additionally, we observed that Compound 1 treatment inhibited the ability of chromosomes to align to the metaphase plate, frequently occupying regions distal to the spindle pole.

Compound 1 treatment also disrupted the ability of β-tubulin to faithfully form the fine spindle microtubules of the mitotic spindle, instead resulting in a compressed phenotype with radiating projections connecting unaligned chromosomes. To assess the uniqueness of this phenotype, we evaluated the metaphase phenotypes of other chemical inhibitors which have shown to alter mitotic progression. These included inhibitors of centromere-associated protein E (CENP-E, also called kinesin-7, GSK92395), kinesin spindle protein (KSP, also called Eg5, Ispinesib), polo like kinases (PLK1/2/3, BI2536), and aurora kinases (AURKA/B/C, VX-680). Treating thymidine-synced FOXC2-HMLER cells with these inhibitors revealed that the majority of these compounds did not induce phenotypes similar to Compound 1, with the exception of GSK92395, which also demonstrated an unaligned chromosome phenotype in line with CENP-E's reported function of aligning chromosomes to the metaphase plate (K. W. Wood et al., *Proc. Natl. Acad. Sci. USA* 107 (2010) 5839-5844). However, GSK92395 treatment did not induce VIM filamentous collapse or alter the morphology of spindle tubulin. Taken together, these results suggest that Compound 1 induces mitotic failure and eventual multinucleation through a novel mechanism which involves interfering with the metaphase organization of chromosomes and the spindle apparatus.

WIF-A induced a significant increase in multinucleated FOXC2-HMLER cells at concentrations (250-500 nM) below those at which it induced an apoptotic, non-adherent phenotype during this treatment period (24 hours). Additionally, treating thymidine synched FOXC2-HMLER cells with WIF-A resulted in the characteristic appearance of unaligned chromosomes during metaphase, although not all metaphase plates displayed an unaligned phenotype as observed with a maximally efficacious dose of Compound 1. While differences in target engagement or off-target modification might explain this difference, together these data identifies the chemical targeting of VIM as a generalizable path for interfering with mitotic progression.

The invention claimed is:

1. A method for treating a patient suffering from a mesenchymally-derived or mesenchymally-transformed cancer, comprising administering to the subject a therapeutically effective amount of a compound or a pharmaceutically acceptable salt thereof is one selected from the following table:

| | |
|---|---|
| 1 | 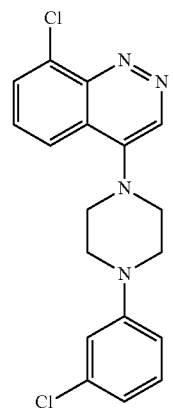 [SMILES: Clc1cccc(N2CCN(c3cnnc4c(Cl)cccc34)CC2)c1] |
| 1A | 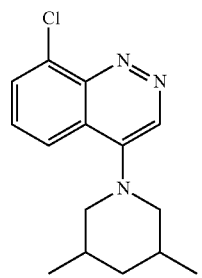 [SMILES: CC1CC(C)CN(c2cnnc3c(Cl)cccc23)C1] |
| 1B | 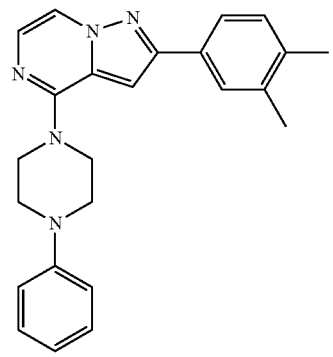 [SMILES: Cc1ccc(-c2cc3c(N4CCN(c5ccccc5)CC4)nccn3n2)cc1C] |

| | |
|---|---|
| 1C | 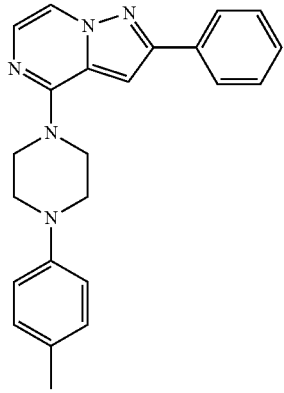 [SMILES: Cc1ccc(N2CCN(c3nccn4nc(-c5ccccc5)cc34)CC2)cc1] |
| 1D | 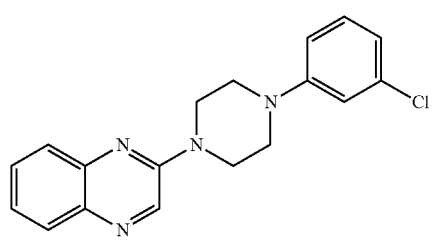 [SMILES: Clc1cccc(N2CCN(c3cnc4ccccc4n3)CC2)c1] |
| 1SRH | 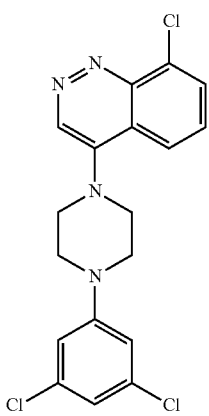 |
| 1SRI | 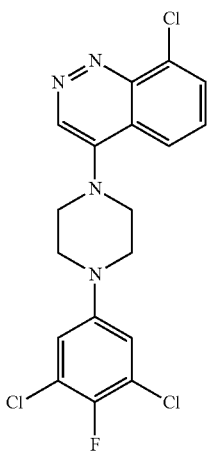 |
| 1SRJ | 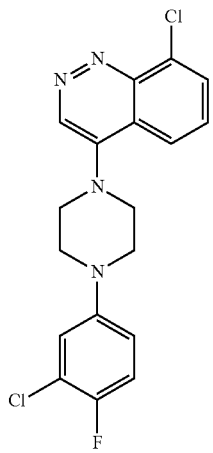 [SMILES: Fc1ccc(N2CCN(c3cnnc4c(Cl)cccc34)CC2)cc1Cl] |
| 1SRK | 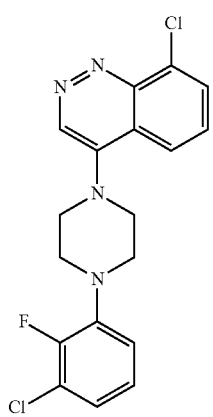 [SMILES: Fc1c(Cl)cccc1N1CCN(c2cnnc3c(Cl)cccc23)CC1] |
| 1SRL | 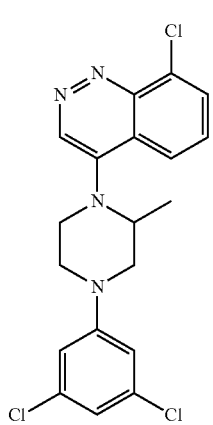 [SMILES: CC1CN(c2cc(Cl)cc(Cl)c2)CCN1c1cnnc2c(Cl)cccc12] |

| | | | |
|---|---|---|---|
| 1SRM | 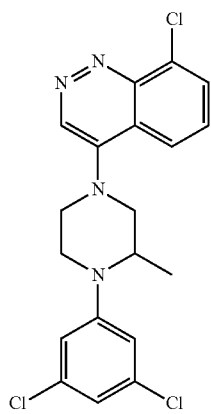 | 1SRQ | 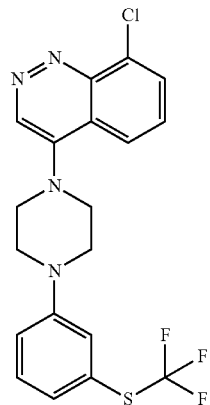 |
| 1SRN | 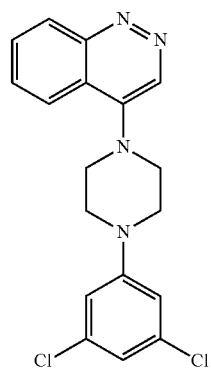 [SMILES: Clc1cc(Cl)cc(N2CCN(c3cnnc4ccccc34)CC2)c1] | | |
| 1SRO | 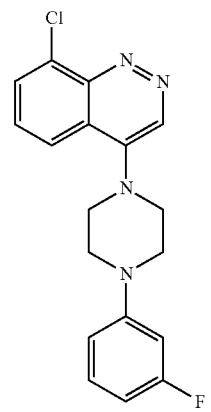 [SMILES: Fc1cccc(N2CCN(c3cnnc4c(Cl)cccc34)CC2)c1] | 1SRU | 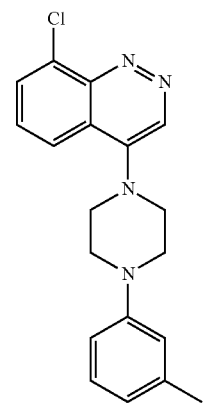 |
| 1SRP | 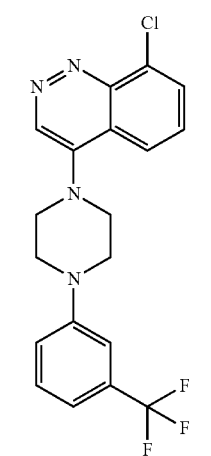 [SMILES: FC(F)(F)c1cccc(N2CCN(c3cnnc4c(Cl)cccc34)CC2)c1] | 1SRT | 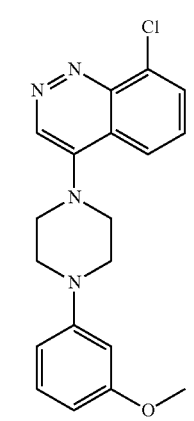 |

1SRU
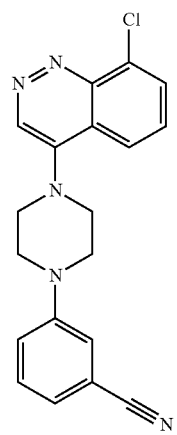 [SMILES: N#Cc1cccc(N2CCN(c3cnnc4c(Cl)cccc34)CC2)c1]
1SRAA
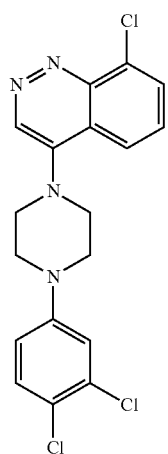
1SRV
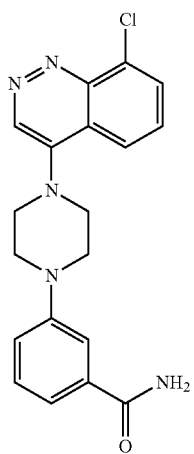 [SMILES: NC(=O)c1cccc(N2CCN(c3cnnc4c(Cl)cccc34)CC2)c1]
1SRAB
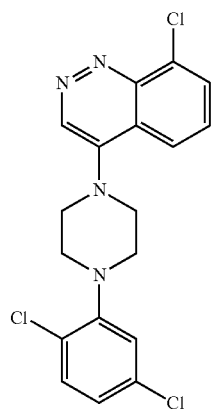
1SRW
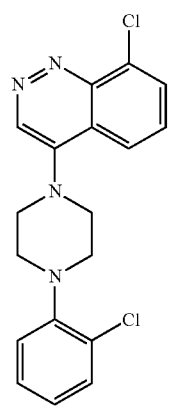 [SMILES: Clc1ccccc1N1CCN(c2cnnc3c(Cl)cccc23)CC1]
1SRAC
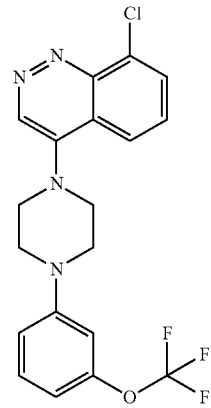

| | |
|---|---|
| 1SRAD | 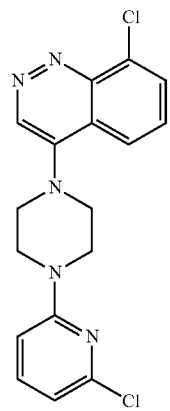 [SMILES: Clc1cccc(N2CCN(c3cnnc4c(Cl)cccc34)CC2)n1] |
| 1SRAG | 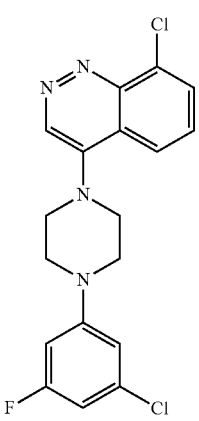 [SMILES: Fc1cc(Cl)cc(N2CCN(c3cnnc4c(Cl)cccc34)CC2)c1] |
| 1SRAH | 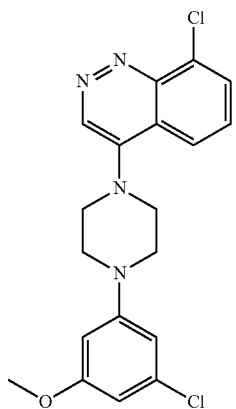 [SMILES: COc1cc(Cl)cc(N2CCN(c3cnnc4c(Cl)cccc34)CC2)c1] |
| 1SRAI | 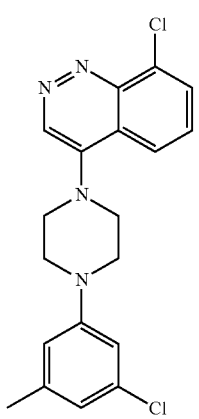 [SMILES: Cc1cc(Cl)cc(N2CCN(c3cnnc4c(Cl)cccc34)CC2)c1] |
| 1SRAJ | 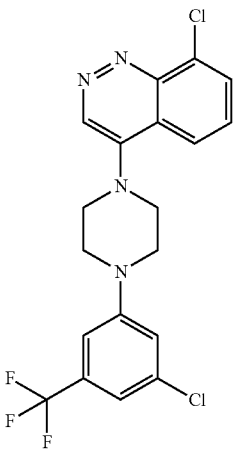 [SMILES: FC(F)(F)c1cc(Cl)cc(N2CCN(c3cnnc4c(Cl)cccc34)CC2)c1] |
| 1SRAK | 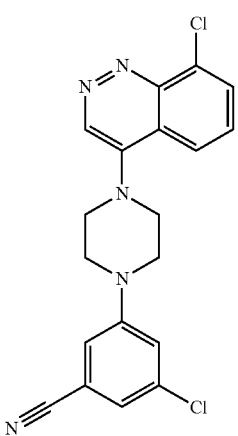 [SMILES: N#Cc1cc(Cl)cc(N2CCN(c3cnnc4c(Cl)cccc34)CC2)c1] |
| 1SRAL | 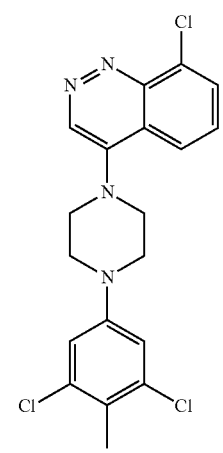 [SMILES: Cc1c(Cl)cc(N2CCN(c3cnnc4c(Cl)cccc34)CC2)cc1Cl] |

-continued
1SRAN
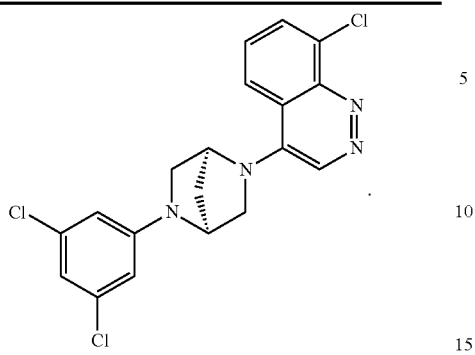
* * * * *